(12) United States Patent
Chan et al.

(10) Patent No.: US 6,762,059 B2
(45) Date of Patent: Jul. 13, 2004

(54) METHODS AND APPARATUSES FOR CHARACTERIZATION OF SINGLE POLYMERS

(75) Inventors: Eugene Y. Chan, Brookline, MA (US); Lance C. Gleich, Somerville, MA (US); Parris S. Wellman, Hillsborough, NJ (US)

(73) Assignee: U.S. Genomics, Inc., Woburn, MA (US)

( * ) Notice: Subject to any disclaimer, the term of this patent is extended or adjusted under 35 U.S.C. 154(b) by 248 days.

(21) Appl. No.: 09/783,472

(22) Filed: Feb. 14, 2001

(65) Prior Publication Data

US 2002/0081744 A1 Jun. 27, 2002

Related U.S. Application Data

(63) Continuation-in-part of application No. 09/636,793, filed on Aug. 11, 2000.
(60) Provisional application No. 60/149,020, filed on Aug. 13, 1999.

(51) Int. Cl.[7] .............................................. G01N 21/01
(52) U.S. Cl. ........................... 436/164; 436/86; 436/94; 436/172; 435/6
(58) Field of Search .......................... 436/94, 164, 172, 436/86; 435/6

(56) References Cited

U.S. PATENT DOCUMENTS

| | | | |
|---|---|---|---|
| 5,079,169 A | | 1/1992 | Chu et al. |
| 5,356,776 A | * | 10/1994 | Kambara et al. ............... 435/6 |
| 5,427,663 A | | 6/1995 | Austin et al. |
| 5,538,898 A | | 7/1996 | Wickramasinghe et al. |
| 5,599,664 A | | 2/1997 | Schwartz |
| 5,707,797 A | * | 1/1998 | Windle .......................... 435/6 |
| 5,795,782 A | | 8/1998 | Church et al. |
| 5,837,115 A | | 11/1998 | Austin et al. |
| 5,840,862 A | | 11/1998 | Bensimon et al. |
| 5,846,724 A | | 12/1998 | Bensimon et al. |
| 5,846,832 A | | 12/1998 | Oefner et al. |
| 5,851,769 A | | 12/1998 | Gray et al. |
| 6,210,896 B1 | | 4/2001 | Chan |
| 6,263,286 B1 | * | 7/2001 | Gilmanshin et al. ............ 702/19 |
| 6,355,420 B1 | | 3/2002 | Chan |
| 6,403,311 B1 | | 6/2002 | Chan |

FOREIGN PATENT DOCUMENTS

| | | |
|---|---|---|
| EP | 0391674 | 10/1990 |
| WO | WO 93/22463 | 11/1993 |
| WO | WO 97/06278 | 2/1997 |
| WO | WO-98/10097 A2 * | 3/1998 |
| WO | WO 98/35012 | 8/1998 |
| WO | WO 00/09757 | 2/2000 |
| WO | WO-00/09757 A1 * | 2/2000 |

OTHER PUBLICATIONS

Fisher88, Fisher Scientific catalog (1988), p. 861.*
Shortreed et al., Anal. Chem. (2000), vol. 72, No. 13, pp. 2879–2885.*
Castro et al., SPIE (1995), vol. 2386, pp. 79–85.*
Ekstrom et al., BioTechniques (2000), vol. 29, No. 3, pp. 582, 584, 586–589.*

(List continued on next page.)

*Primary Examiner*—Jan Ludlow
(74) *Attorney, Agent, or Firm*—Wolf, Greenfield & Sacks, P.C.

(57) ABSTRACT

The present invention relates to methods and apparatuses for characterization of single polymers. In particular, the invention relates to methods and apparatuses for determination of the velocities of single elongated polymers. Center-of-mass velocity, center-to-center velocity, end-to-end velocity and rise-time velocity are determined using time-correlated measurements of single elongated polymers in two or more detection zones. The invention also relates to methods of determinating lengths and molecular masses of single polymers and to methods of determining the distance between landmarks on a single polymers based on their velocities. The invention further relates to methods of single-molecule DNA restriction fragment analysis.

9 Claims, 46 Drawing Sheets

OTHER PUBLICATIONS

Austin et al., 1997, "Stretch Genes", Physics Today 50:32–38.

Austin and Volkmuth, 1993, "Electrophoresis and microlithography", Analusis 21:235–238.

Bakajin et al., 1998, "Electrohydrodynamic stretching of DNA in confined environments", Phys. Rev. Lett. 80:2737–2740.

Bensimon et al., 1995, "Stretching DNA with a receding meniscus: experiments and models", Phys. Rev. Lett. 74:4754–4757.

Bensimon et al., 1994, "Alignment and sensitive d t ction of DNA by a moving interfac ", Science 265:2096–2098.

Bustamante et al., 1994, "Entropic elasticity of lambda–phage DNA", Science 265:1599–1600.

Chou et al., 1999, "A microfabricated device for sizing and sorting DNA molecules", Proc. Natl. Acad. Sci. USA 96:11–13.

Chu, 1991, "Laser manipulation of atoms and particles", Science 253:861–866.

Cluzel et al., 1996, "DNA: an extensible molecule", Science 271:792–794.

Deen, 1998, *Analysis of Transport Phenomena,* Oxford University Press, NY, pp. 275–278.

Duke and Austin, 1998, "Microfabricated sieve for the continuous sorting of macromolecules", Phys. Rev. Lett. 80:1552–1555.

Ertas, 1998, "Lateral separation of macromolecules and polyelectrolytes in microlithographic arrays", Phys. Rev. Lett. 80:1548–1551.

Grandbois et al., 1999, "How strong is a covalent bond?", Science 283:1727–1730.

Harrison et al., 1992, "Capillary electrophoresis and sample injection systems integrated on a planar glass chip", Anal. Chem. 64:1926–1932.

Hatfield and Quake, 1999, "Dynamic properties of an extended polymer in solution", Phys. Rev. Lett. 82:3548–3551.

Houseal et al., 1989, "Real–time imaging of single DNA molecules with fluorescence microscopy", Biophys. J. 56:507–516.

Jacobson et al., 1995, "Fused quartz substrates for microchip electrophoresis", Anal. Chem. 67:2059–2063.

Kabata et al., 1993, "Visualization of single molecules of RNA polymerase sliding along DNA", Science 262:1561–1563.

Kim and Baldwin, 1990, "Intermediates in the folding reactions of small proteins", Annu. Rev. Biochem. 59:631–660.

Lyon and Nie, 1997, "Confinement and detection of single molecules in submicrometer channels", Anal. Chem. 69:3400–3405.

Marko, 1998, "DNA under high tension: overstretching, undertwisting, and relaxation dynamics", Physical Rev. E 27:2134–2149.

Marko and Siggia, 1995, "Stretching DNA", Macromolecules 28:8759–8770.

Parra and Windle, 1993, "High resolution visual mapping of stretched DNA by fluorescent hybridization", Nature Genet. 5:17–21.

Perkins et al., 1994, "Direct observation of tube–like motion of a single polymer chain", Science 264:819–822.

Schmalzing et al., 1998, "DNA sequencing on microfabricated electrophorectic devices", Anal. Chem. 70:2303–2310.

Schmalzing et al., 1997, "DNA typing in thirty seconds with a microfabricated device", Proc. Natl. Acad. Sci. USA 94:10273–10278.

Schwartz et al., 1993, "Ordered restriction maps of *Saccharomyces cerevisiae* chromosomes constructed by optical mapping", Science 262:110–114.

Schwartz and Koval, 1989, "Conformational dynamics of individual DNA mol cules during gel electrophoresis", Natur 338:520–522.

Seiler et al., 1993, "Planar glass chips for capillary electrophoresis: repetitive sample injection, quantitation and separation fficiency", Anal. Chem. 65:1481–1488.

Smith et al., 1999, "Single–polymer dynamics in steady shear flow", Science 283:1724–1727.

Smith and Chu, 1998, "Response of flexible polymers to a sudden elongational flow", Scienc 281:1335–1340.

Smith et al., 1992, "Direct mechanical measurements of the elasticity of single DNA molecules by using magnetic beads", Science 258:1122–1126.

Smith et al., 1989, "Observation of individual DNA molecules undergoing gel electrophoresis", Science 243:203–206.

Tan and Kopelman, 1996, "Nanoscale Imaging and Sensing by Near–Field Optics", in: *Fluorescence Imaging; Spectroscopy and Microscopy,* Wang and Herman, eds., Chemical Analysis Series 137:407–475.

Volkmuth et al., 1994, "DNA electrodiffusion in a 2D array of posts", Phys. Rev. Lett. 72:2117–2120.

Volkmuth and Austin, 1992, "DNA electrophoresis in microlithographic arrays", Nature 358:600–602.

Washizu et al., 1995, "Applications of electrostatic stretch–and–positioning of DNA", IEEE Trans. Industry Applications 31:447–456.

Washizu and Kurosawa, 1990, "Electrostatic manipulation of DNA in microfabricated structures", IEEE Trans. Industry Applications 26:1165–1172.

Woolley and Mathies, 1994, "Ultra–high speed DNA fragment separations using microfabricated capillary array electrophoresis chips", Proc. Natl. Acad. Sci. USA 91:11348–11352.

Zimmerman and Cox, 1994, "DNA stretching on functionalized gold surfaces", Nucl. Acids Res. 22:492–497.

Austin et al., 1997, "Stretch Genes", Physics Today 50:32–38.

Austin and Volkmuth, 1993, "Electrophoresis and microlithography", Analysis 21:235–238.

Bakajin et al., 1998, "Electrohydrodynamic stretching of DNA in confined environments", Phys. Rev. Lett. 80:2737–2740.

Bensimon et al., 1995, "Stretching DNA with a receding meniscus: experiments and models", Phys. Rev. Lett. 74:4754–4757.

Bensimon et al., 1994, "Alignment and sensitive direction of DNA by a moving interface ", Science 265:2096–2098.

Bustamante et al., 1994, "Entropic elasticity of lambda–phage DNA", Science 265:1599–1600.

Chou et al., 1999, "A microfabricated device for sizing and sorting DNA molecules", Proc. Natl. Acad. Sci. USA 96:11–13.

Chu, 1991, "Laser manipulation of atoms and particles", Science 253:861–866.

Cluzel et al., 1996, "DNA: an extensible molecule", Science 271:792.

Deen, 1998, *Analysis of Transport Phenomena,* Oxford University Press, NY, pp. 275–278.

Duke et al., 1998, "Microfabricated sieve for the continuous sorting of macromolecules", Phys. Rev. Lett. 80:1552–1555.

Ertas, 1998, "Lateral separation of macromolecules and polyelectrolytes in microlithographic arrays", Phys. Rev. Lett. 80:1548–1551.

Grandbois et al., 1999, "How strong is a covalent bond?" Science 283:1727–1730.

Harrison et al., 1992, "Capillary electrophoresis and sample injection systems integrated on a planar glass chip", Anal. Chem. 64:1926–1932.

Hatfield and Quake, 1999, "Dynamic properties of an extended polymer in solution", Phys. Rev. Lett. 82:3548–3551.

Houseal et al., 1989, "Real–time imaging of single DNA molecules with fluorescence microscopy", Biophys. J. 56:507–516.

Jacobson et al., 1995, "Fused quartz substrates for microchip electrophoresis", Anal. Chem. 67:2059–2063.

Kabata et al., 1993, "Visualization of single molecules of RNA polymerase sliding along DNA", Science 262:1561–1563.

Kim et al., 1990, "Intermediates in the folding reactions of small proteins", Annu. Rev. Biochem. 59:631–660.

Lyon et al., 1997, "Confinement and detection of single molecules in submicrometer channels", Anal. Chem. 69:3400–3405.

Marko, 1998, "DNA under high tension: overstretching, undertwisting, and relaxation dynamics", Physical Rev. E 27:2134–2149.

Marko et al., 1995, "Stretching DNA", Macromolecules 28:8759–8770.

Parra et al., 1993, "High resolution visual mapping of stretched DNA by fluorescent hybridization", Nature Genet. 5:17–21.

Perkins et al., 1994, "Direct observation of tube–like motion of a single polymer chain", Science 264:819–822.

Schmalzing et al., 1998, "DNA sequencing on microfabricated electrophorectic devices", Anal. Chem. 70:2303–2310.

Schmalzing et al., 1997, "DNA typing in thirty seconds with a microfabricated device", Proc. Natl. Acad. Sci. USA 94:10273–10278.

Schwartz et al., 1993, "Ordered restriction maps of *Saccharomyces cerevisiae* chromosomes constructed by optical mapping", Science 262:110–114.

Schwartz et al., 1989, "Conformational dynamics of individual DNA mol cules during gel electrophoresis", Nature 338:520–522.

Seiler et al., 1993, "Planar glass chips for capillary electrophoresis: repetitive sample injection, quantitation and separation fficiency", Anal. Chem. 65:1481–1488.

Smith et al., 1999, "Single–polymer dynamics in steady shear flow", Science 283:1724–1727.

Smith et al., 1998, "Response of flexible polymers to a sudden elongational flow", Science 281:1335–1340.

Smith et al., 1992, "Direct mechanical measurements of the elasticity of single DNA molecules by using magnetic beads", Science 258:1122–1126.

Smith et al., 1989, "Observation of individual DNA molecules undergoing gel electrophoresis", Science 243:203–206.

Tan et al., 1996, "Nanoscale Imaging and Sensing by Near–Field Optics", in : *Fluorescence Imaging; Spectroscopy and Microscopy,* Wang and Herman, eds., Chemical Analysis Series 137:407–475.

Volkmuth et al., 1994, "DNA electrodiffusion in a 2D array of posts", Phys. Rev. Lett. 72:2117–2120.

Volkmuth et al., 1992, "DNA electrophoresis in microlithographic arrays", Nature 358:600–652.

Washizu et al., 1995, "Applications of electrostatic stretch–and–positioning of DNA", IEEE Trans. Industry Applications 31:447–456.

Washizu et al., 1990, "Electrostatic manipulation of DNA in microfabricated structures", IEEE Trans. Industry Applications 26:1165–1172.

Woolley et al., PNAS 91:11348–11352.

Zimmerman et al., 1994, "DNA stretching on functionalized gold surfaces", Nucl. Acids Res. 22:492–497.

Fisher88, Fisher Scientific Catalog (1988), p. 861.

\* cited by examiner

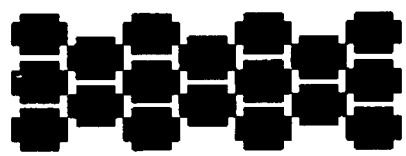
xiv
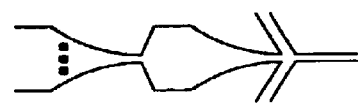
xvix
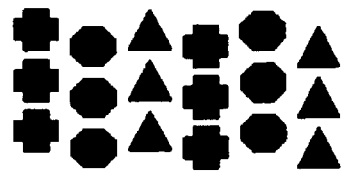
xv
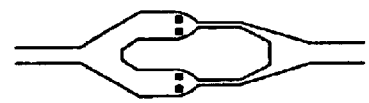
xx
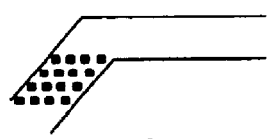
xvi
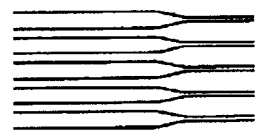
xxi
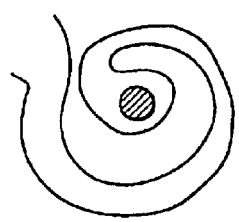
xvii
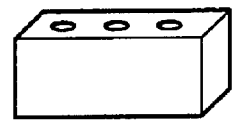
xxii
xviii
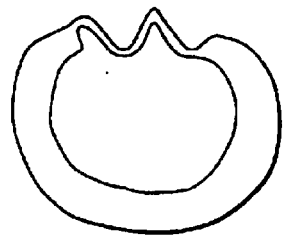
xxiii
FIG.3B

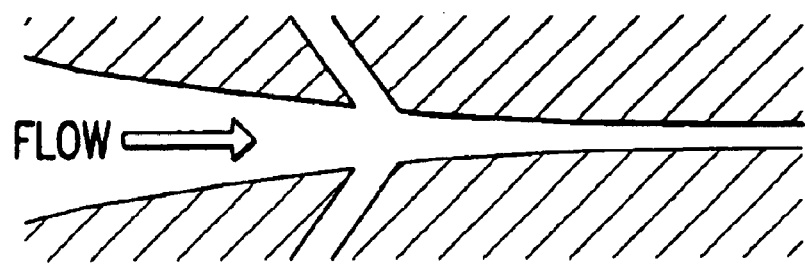
FIG.9
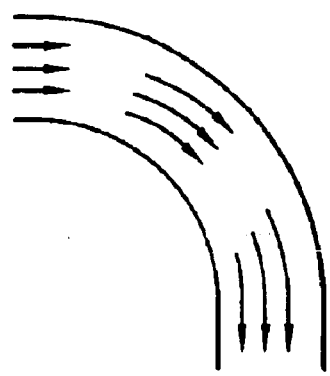
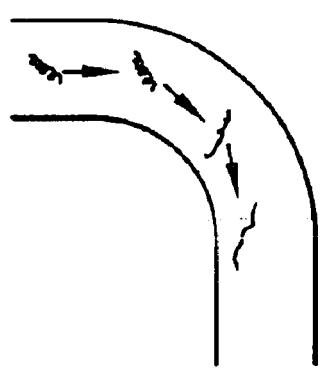
FIG.10A  FIG.10B

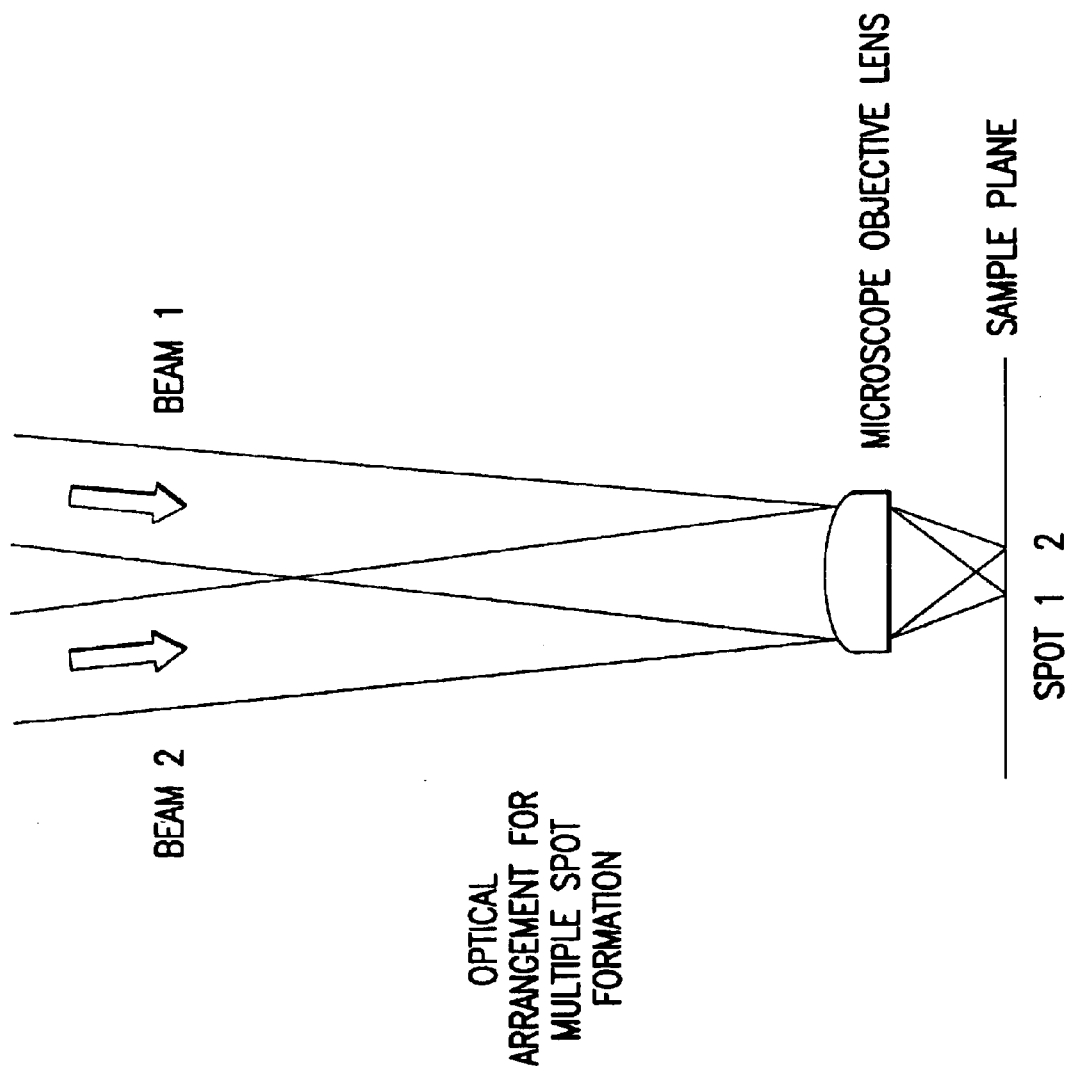

METHODS AND APPARATUSES FOR CHARACTERIZATION OF SINGLE POLYMERS

This application is a continuation-in-part of co-pending U.S. patent application Ser. No. 09/636,793, filed Aug. 11, 2000, which claims the benefit of U.S. Provisional Application Serial No. 60/149,020, filed Aug. 13, 1999, each of which is incorporated herein by reference in its entirety.

1. FIELD OF THE INVENTION

The present invention relates to methods and apparatuses for characterization of single polymers. In particular, the invention relates to methods and apparatuses for determination of the velocities of single elongated polymers. The invention also relates to methods for determination of the length and molecular mass of single polymers. The invention further relates to methods of determining the distance between landmarks on single polymers.

2. BACKGROUND OF THE INVENTION

Analysis of the structure and dynamics of single macromolecules in a fluid sample has attracted considerable interest due in part to the rapid development of methodologies for the manipulation and detection of single macromolecules. For example, recent developments in experimental techniques and available hardware have increased dramatically the sensitivity of detection so that optical detection can be made of single dye molecules in a sample. Single dye detection can be done in aqueous solution, at room temperature (see, e.g., Weiss, 1999, Science 283: 1676–1683), and in very small volumes to reduce background. Such single-molecule based analytical methods are especially useful in the analysis of biological macromolecules, such as nucleic acid molecules and proteins. Single-molecule analytical methods require small amounts of sample, thereby alleviating tedious efforts in generating large amounts of sample material. For example, single-molecule analytical methods may allow analysis of the structure of nucleic acid molecules without amplification, e.g., by polymerase-chain reaction (PCR). Single-molecule analytical methods also allow analysis of individual molecules, and are thus particularly useful in the identification of structural and/or dynamical features without the effect of averaging over a heterogeneous population.

A single-molecule electrophoresis (SME) method which combines single molecule detection and electrophoresis has been reported for the detection and identification of single molecules in solution (Castro and Shera, 1995, Anal. Chem. 67: 3181–3186). In SME, sizing of single molecules is accomplished through determination of electrophoretic velocities by measuring the time required for individual molecules to travel a fixed distance between two laser beams. This method has been applied to DNA, to fluorescent proteins and to simple organic fluorophores. For example, SME offers a single-molecule method for sizing of DNA restriction fragments. However, SME detects only the presence or absence of a molecule. The method does not provide information regarding the internal structure of a molecule.

A single-molecule DNA sizing method using a microfabricated device has also been reported (Chou et al., 1999, Proc. Natl. Acad. Sci. USA 96:11–13). The method makes use of the fact that the amount of intercalated dye is proportional to the length of the molecule, and determines the lengths of single DNA molecules by measuring the total fluorescence intensity of DNA stained with intercalating dye molecules. Thus, the method does not use electrophoretic mobilities to determine sizes of molecules. This method also does not provide information regarding the internal structure of a molecule.

PCT Publication No. WO 98/10097 discloses a method and apparatus for detection of single molecules emitting two-color fluorescence and determination of molecular weight and concentration of the molecules. The method involves labeling of individual molecules with at least two fluorescent probes of different emission spectrum. Simultaneous detection of the two labels indicates the presence of the molecule. The velocity of the molecule is determined by measuring the time required for the molecules to travel a fixed distance between two laser beams. Comparison of the molecule's velocity with that of standard species permits determination of the molecular weight of the molecule, which may be present in a concentration as small as one femtomolar.

Other techniques for characterizing single macromolecules include a method described in U.S. Pat. No. 5,807,677 for direct identification of a specific target nucleic acid sequence having a low copy number in a test solution. This method involves the preparation of a reference solution of a mixture of different short oligonucleotides. Each oligonucleotide includes a sequence complementary to a section of the target sequence and is labeled with one or more fluorescent dye molecules. The reference solution is incubated with the test solution under conditions favorable to hybridization of the short oligonucleotides with the nucleic acid target. The target sequence is identified in the solution by detection of the nucleic acid strands to which one or more of the labeled oligonucleotides are hybridized. To amplify the fluorescence signal, a "cocktail" of different oligonucleotides are used which are capable of hybridizing with sequences adjacent to but not overlapping with the target sequence. The disadvantage of this method is that, in order to design probes of the proper sequence, the exact sequence of the target nucleic acid and surrounding sequences must be known. A method described in U.S. Pat. No. 5,599,664 and European Patent No. EP 0391674 allows sizing of DNA molecules by first subjecting a DNA molecule to a force such that the DNA molecule is elongated and then measuring the conformational relaxation dynamics. In another method (Schmalzing et al., 1998, Analytical Chemistry 70:2303–2310; Schmalzing et al, 1997, Proc. Natl. Acad. Sci. USA 94:10273–10278), microfabricated devices for DNA analysis were developed, including sequencing, which employ small-scale versions of traditional techniques, such as electrophoresis.

None of these single molecule analytical methods allows the determination of the internal structure of the molecule. A challenge to the characterization of the internal structure, e.g., the linear sequence of monomers, in a single polymer chain is from the natural tendency of polymers in most media to adopt coiled conformations. The average degree of such coiling is dependent on, inter alia, the interaction of the polymer with the surrounding solution, the rigidity of the polymer, and the energy of interaction of the polymer with itself. In most cases, the coiling is quite significant. For example, a λ-phage DNA, with a B-form contour length of about 16 $\mu$m long, has a random coil diameter of approximately 1 $\mu$m in water (Smith et al., 1989, Science 243:203–206).

Methods of elongating DNA molecules by fluid flow have been reported (Perkins et al. Science 276:2016–2021; Smith et al., Science 283:1724–1727). In one method, DNA molecules are stretched by an elongational flow. The probability distribution of molecular extension was determined as a function of time and strain rate. Detailed dynamics of elongated DNA molecules in elongational flow has also been observed. In another method DNA molecules are stretched by a steady shear flow. The probability distribution for the molecular extension was determined as a function of shear rate. It was found that, in contrast to the behavior in pure elongational flow, the average polymer extension in shear flow does not display a sharp coil-stretch transition.

DNA has also been stretched by electrophoresis as part of a near-field detection scheme for sequencing biomolecules. DNA has been elongated by electrophoresis both in a gel and in solution, using electrical forces to move the DNA in position for reading (U.S. Pat. No. 5,538,898). However, no data were given to determine the quality of the stretching of large polymers, and the technique is limited to analyzing approximately 3 megabases at a time.

Gravitational forces have also been used to stretch DNA (U.S. Pat. No. 5,707,797; Windle (1993) Nature Genetics 5:17–21). In this technique, drops of DNA from the sodium dodecyl sulfate lysing of cells were allowed to run down a slide held at an angle. The effect of gravity was enough to stretch out the DNA, even to its over-stretched S-DNA form. The DNA was then immobilized on the slide, making processing, e.g., fluorescent labeling, prior to stretching relatively difficult.

Single-molecule DNA analytical methods which involve elongation of DNA molecule include optical mapping (Schwartz et al., 1993, Science 262:110–113; Meng et al., 1995, Nature Genet. 9:432; Jing et al., Proc. Natl. Acad. Sci. USA 95:8046–8051) and fiber-fluorescence in situ hybridization (fiber-FISH) (13ensimon et al., Science 265:2096; Michalet et al., 1997, Science 277:1518). In optical mapping, DNA molecules are elongated in a fluid sample and fixed in the elongated conformation in a gel or on a surface. Restriction digestions are then performed on the elongated and fixed DNA molecules. Ordered restriction maps are then generated by determining the size of the restriction fragments. In fiber-FISH, DNA molecules are elongated and fixed on a surface by molecular combing. Hybridization with fluorescently labeled probe sequences allows determination of sequence landmarks on the DNA molecules. Both methods require fixation of elongated molecules so that molecular lengths and/or distances between markers can be measured.

A method for measuring the length and distances between markers on DNA was developed by Kambara et al. (U.S. Pat. No. 5,356,776). This method involves electrophoresis of DNA molecule labeled at both termini and/or internal sites through a gel, in which the DNA molecule is forced into a straight line, transferring the straightened DNA molecule into a buffer containing no gel where fluorescent labels are detected. The time interval between the detection of the two labels is used to determine the distance between them. If the two labels label the termini of the DNA molecule, the distance between the labels measures the length of the molecule. The method, which does not provide means for determining the velocity of the DNA molecule, relies on estimating the velocity of DNA from the migration rate of the DNA molecule.

Flow based single-molecule analytical methods for elongation and characterization of single macromolecules have not been widely adopted due in part to the difficulty in precise measurement of molecular characteristics, e.g., the length of the macromolecule, the distance between two landmarks on a macromolecule, etc. For example, to determine the length of an elongated macromolecule as it travels through a detection zone, e.g., a laser excitation zone, it is necessary to know the velocity of the macromolecule. The flow velocity field can be measured by various known methods, e.g., particle image velocimetry (PIV) (see, e.g., Meinhart et al., 1999, Experiments in Fluids 27: 414–419; Meinhart et al., 2000, Meas. Sci. Technol. 11:809–814). The velocities of flexible objects, such as elongated polymers, may not be the same as the flow velocities. For example, in most flows the length of a polymer may be changing as it travels along with flow. In particular, the length of a polymer may be changing as a consequence of changing flow velocity. There is therefore a need for faster, simpler, more reliable and more universally applicable methods for measuring the velocities of single elongated polymers traveling in a flow. There is also a need for more accurate methods for determining the length of single elongated polymers and/or distances between landmarks on single elongated polymers.

Citation of a reference herein shall not be construed as indicating that such reference is prior art to the present invention.

3. SUMMARY OF THE INVENTION

The present invention provide methods and apparatuses for determining the velocities of single elongated macromolecules. The methods of the invention are based on time-correlated measurements of an elongated macromolecule at each of a plurality of detection zones. The detection zones are located along the travel path of the elongated macromolecule at predetermined spacings. Signal amplitude profiles, e.g, intensity-time curves when fluorescence based measurements are used, of an elongated macromolecule are measured as the macromolecule passes through each of the detection zones. The measurements in the plurality of detection zones are time-correlated, e.g., synchronized, so that the temporal spacings between signal amplitude profiles measured at different detections zones are also determined.

In one embodiment, the invention provides a method for determining velocity of a single elongated polymer, said method comprising measuring a plurality of signal amplitude profiles of said elongated polymer, each signal amplitude profile comprising measurements taken at a different one of a plurality of detection zones and determining said velocity of said elongated polymer from said plurality of signal amplitude profiles, wherein each said signal amplitude profile comprises measurements in the respective detection zone of a signal generated at said single elongated polymer at a plurality of times, said plurality of times comprising times that are before and after said elongated polymer is in said detection zone, wherein said plurality of detection zones are located in order along the path of said elongated polymer at predetermined distances, and wherein said plurality of signal amplitude profiles are measured in a time-correlated manner. In preferred embodiments, said measuring is performed by a method comprising measuring fluorescence intensity and the signal amplitude profiles are intensity-time curves. In one embodiment, the velocity determined is a center-of-mass velocity. In another embodiment, the velocity determined is a center-to-center velocity. In still another embodiment, the velocity determined is an end-to-end velocity, e.g., a leading-end-to-leading-end velocity or a trailing-end-to-trailing end velocity. In still another embodiment, the velocity determined is a rise-time velocity.

In another embodiment, the invention provides a method for determining the length of a single elongated polymer, said method comprising measuring a plurality of signal amplitude profiles of said elongated polymer, each signal amplitude profile comprising measurements taken at a different one of a plurality of detection zones, and determining said length of said elongated polymer using said plurality of signal amplitude profiles and velocity of said elongated polymer, wherein each of said plurality of signal amplitude profiles comprises measurements in the respective detection zone of a signal generated at said single elongated polymer at a plurality of times, said plurality of times comprising times that are before and after said elongated polymer is in said detection zone, wherein said plurality of detection zones are located in order along the path of said elongated polymer at predetermined distances, wherein said plurality of signal amplitude profiles are measured in a time-correlated manner, and wherein said velocity of said elongated polymer is determined from said plurality of signal amplitude profiles. In preferred embodiments, said measuring is performed by a method comprising measuring fluorescence intensity and the signal amplitude profiles are intensity-time curves. In one embodiment, the velocity determined is a center-of-mass velocity. In another embodiment, the velocity determined is a center-to-center velocity. In still another embodiment, the velocity determined is an end-to-end velocity, e.g., a leading-end-to-leading-end velocity or a trailing-end-to-trailing end velocity. In still another embodiment, the velocity determined is a rise-time velocity.

In still another embodiment, the invention provides a method for determining the length of a single elongated polymer, said method comprising: (a) measuring a first signal amplitude profile of said single elongated polymer at a first detection zone; (b) measuring a second signal amplitude profile of said single elongated polymer at a second detection zone; (c) determining a velocity of said single elongated polymer at said first and second detection zones from said first and/or second signal amplitude profiles; and (d) determining length of said single elongated polymer by multiplying time difference between leading and trailing edges of said first or said second signal amplitude profile with said velocity; wherein each of said first and second signal amplitude profiles comprises measurements in the respective detection zone of a signal generated at said single elongated polymer at a plurality of times, said plurality of times comprising times that are before and after said elongated polymer is in said detection zone, wherein said plurality of detection zones are located in order along the path of said elongated polymer at predetermined distances, and wherein said first and second signal amplitude profiles are measured in a time-correlated manner. In preferred embodiments, said measuring is performed by a method comprising measuring fluorescence intensity and the first and second signal amplitude profiles are intensity-time curves. In one embodiment, the velocity determined is a center-of-mass velocity. In another embodiment, the velocity determined is a center-to-center velocity. In still another embodiment, the velocity determined is an end-to-end velocity, e.g., a leading-end-to-leading-end velocity or a trailing-end-to-trailing end velocity. In still another embodiment, the velocity determined is a rise-time velocity.

In still another embodiment, the invention provides a method for determining the length of a single elongated polymer, said method comprising: (a) measuring a plurality of signal amplitude profile of said single elongated polymer each at each of a plurality of detection zones; (b) determining a velocity of said single elongated polymer between each successive pair of detection zones from pair of signal amplitude profiles measured in respective pair of detection zones; and (c) determining length of said elongated polymer by (i) multiplying time interval for said elongated polymer to travel between each successive pair of detection zones with said velocity between said pair of detection zones and (ii) summing all products between time interval in one of said plurality of signal amplitude profiles; wherein each said signal amplitude profile comprises measurements in the respective detection zone of a signal generated at said single elongated polymer at a plurality of times, said plurality of times comprising times that are before and after said elongated polymer is in said detection zone, wherein said plurality of detection zones are located in order along the path of said elongated polymer at predetermined distances, said distances are shorter than length of elongated polymers, and wherein said plurality of signal amplitude profiles are measured in a time-correlated manner. In preferred embodiments, said measuring is performed by a method comprising measuring fluorescence intensity and the signal amplitude profiles are intensity-time curves. In one embodiment, the velocity determined is a center-of-mass velocity. In another embodiment, the velocity determined is a center-to-center velocity. In still another embodiment, the velocity determined is an end-to-end velocity, e.g., a leading-end-to-leading-end velocity or a trailing-end-to-trailing end velocity. In still another embodiment, the velocity determined is a rise-time velocity.

In still another embodiment, the invention also provides a method for determining a distance between a first and a second landmark on an elongated polymer, said method comprising: (a) detecting at a first detection zone said first and second landmarks on said elongated polymer; (b) detecting at a second detection zone said first and second landmark on said elongated polymer; (c) determining the velocity of said elongated polymer by dividing the distance between said first and second detection zones with time interval between detection of said first or second landmark in said first detection zone and detection of said first and second landmark in said second detection zone; and (d) determining said distance between said first and second landmark by multiplying time interval between detection of said first and second landmark at said first detection zone or said second detection zone; wherein said first and second detection zones are located in order along the path of said elongated polymer at predetermined distances, and wherein said detection in said first and said second detection zones are carried out in a time-correlated manner.

The invention also provides a method for determining velocity of a single polymer, said method comprising: (a) moving said single polymer along an elongation structure, said elongation structure comprising a tapered channel with a first end and a second end, whereby said single polymer is elongated in said tapered channel as said single polymer moves along said tapered channel from said first end to said second end; and (b) measuring a plurality of signal amplitude profiles of said single polymer, each signal amplitude profile comprising measurements taken at a different one of a plurality of detection zones and determining said velocity of said elongated polymer from said plurality of signal amplitude profiles, wherein each said signal amplitude profile comprises measurements in the respective detection zone of a signal generated at said single elongated polymer at a plurality of times, said plurality of times comprising times that are before and after said single polymer is in said detection zone, wherein said plurality of detection zones are located in order along the path of said single polymer at predetermined distances, and wherein said plurality of signal amplitude profiles are measured in a time-correlated manner. In preferred embodiments, said measuring is performed by a method comprising measuring fluorescence intensity and the signal amplitude profiles are intensity-time curves. In one embodiment, the velocity determined is a center-of-mass velocity. In another embodiment, the velocity determined is a center-to-center velocity. In still another embodiment, the velocity determined is an end-to-end velocity, e.g., a leading-end-to-leading-end velocity or a trailing-end-to-trailing end velocity. In still another embodiment, the velocity determined is a rise-time velocity.

The invention also provides a method for determining velocity of a single polymer, said method comprising: (a) moving said single polymer along an elongation structure, said elongation structure comprising a central channel holding fluid and a plurality of side channels holding fluid connected to said central channel, said central channel comprising a first end and a second end, wherein said single polymer is moved along said central channel from said first end to said second end and is elongated; and (b) measuring a plurality of signal amplitude profiles of said single polymer, each signal amplitude profile comprising measurements taken at a different one of a plurality of detection zones and determining said velocity of said elongated polymer from said plurality of signal amplitude profiles, wherein each said signal amplitude profile comprises measurements in the respective detection zone of a signal generated at said single elongated polymer at a plurality of times, said plurality of times comprising times that are before and after said single polymer is in said detection zone, wherein said plurality of detection zones are located in order along the path of said single polymer at predetermined distances, and wherein said plurality of signal amplitude profiles are measured in a time-correlated manner. In preferred embodiments, said measuring is performed by a method comprising measuring fluorescence intensity and the signal amplitude profiles are intensity-time curves. In one embodiment, the velocity determined is a center-of-mass velocity. In another embodiment, the velocity determined is a center-to-center velocity. In still another embodiment, the velocity determined is an end-to-end velocity, e.g., a leading-end-to-leading-end velocity or a trailing-end-to-trailing end velocity. In still another embodiment, the velocity determined is a rise-time velocity.

The invention also provides a method for determining velocity of a single polymer, said method comprising: (a) moving said single polymer along an elongation structure, said elongation structure comprising a channel with at least one bend, said channel comprising a first end and a second end, wherein said single polymer is moved from said first end to said second end, wherein said single polymer is moved along said channel from said first end to said second end and is elongated; and (b) measuring a plurality of signal amplitude profiles of said single polymer, each signal amplitude profile comprising measurements taken at a different one of a plurality of detection zones and determining said velocity of said elongated polymer from said plurality of signal amplitude profiles, wherein each said signal amplitude profile comprises measurements in the respective detection zone of a signal generated at said single elongated polymer at a plurality of times, said plurality of times comprising times that are before and after said single polymer is in said detection zone, wherein said plurality of detection zones are located in order along the path of said single polymer at predetermined distances, and wherein said plurality of signal amplitude profiles are measured in a time-correlated manner. In preferred embodiments, said measuring is performed by a method comprising measuring fluorescence intensity and the signal amplitude profiles are intensity-time curves. In one embodiment, the velocity determined is a center-of-mass velocity. In another embodiment, the velocity determined is a center-to-center velocity. In still another embodiment, the velocity determined is an end-to-end velocity, e.g., a leading-end-to-leading-end velocity or a trailing-end-to-trailing end velocity. In still another embodiment, the velocity determined is a rise-time velocity.

The invention also provides a method for determining velocity of a single polymer, said method comprising: (a) moving said single polymer along an elongation structure, said elongation structure comprising a channel and a plurality of obstacles to motion of said single polymer within said channel, said channel comprising a first end and a second end, wherein said single polymer moves along said channel from said first end to said second end and is elongated; and (b) measuring a plurality of signal amplitude profiles of said single polymer, each signal amplitude profile comprising measurements taken at a different one of a plurality of detection zones and determining said velocity of said elongated polymer from said plurality of signal amplitude profiles, wherein each said signal amplitude profile comprises measurements in the respective detection zone of a signal generated at said single elongated polymer at a plurality of times, said plurality of times comprising times that are before and after said single polymer is in said detection zone, wherein said plurality of detection zones are located in order along the path of said single polymer at predetermined distances, and wherein said plurality of signal amplitude profiles are measured in a time-correlated manner. In preferred embodiments, said measuring is performed by a method comprising measuring fluorescence intensity and the signal amplitude profiles are intensity-time curves. In one embodiment, the velocity determined is a center-of-mass velocity. In another embodiment, the velocity determined is a center-to-center velocity. In still another embodiment, the velocity determined is an end-to-end velocity, e.g., a leading-end-to-leading-end velocity or a trailing-end-to-trailing end velocity. In still another embodiment, the velocity determined is a rise-time velocity.

The invention also provides a method for determining velocity of a single polymer, said method comprising: (a) moving said single polymer along an elongation structure, said elongation structure comprising a first channel, said first channel comprising a first end, a second end, and a plurality of posts in a staggered arrangement between said first end and said second end, and a second channel, said second channel comprising a third end and a fourth end, said third end being connected to said first channel at said second end, said second channel decreasing in width from said third end to said fourth end, wherein said single polymer moves along said channel from said first end to said fourth end and is elongated; and (b) measuring a plurality of signal amplitude profiles of said single polymer, each signal amplitude profile comprising measurements taken at a different one of a plurality of detection zones and determining said velocity of said elongated polymer from said plurality of signal amplitude profiles, wherein each said signal amplitude profile comprises measurements in the respective detection zone of a signal generated at said single elongated polymer at a plurality of times, said plurality of times comprising times that are before and after said single polymer is in said detection zone, wherein said plurality of detection zones are located in order along the path of said single polymer at predetermined distances, and wherein said plurality of signal amplitude profiles are measured in a time-correlated manner. In preferred embodiments, said measuring is performed by a method comprising measuring fluorescence intensity and the signal amplitude profiles are intensity-time curves. In one embodiment, the velocity determined is a center-of-mass velocity. In another embodiment, the velocity determined is a center-to-center velocity. In still another embodiment, the velocity determined is an end-to-end velocity, e.g., a leading-end-to-leading-end velocity or a trailing-end-to-trailing end velocity. In still another embodiment, the velocity determined is a rise-time velocity.

The invention also provides a method for determining length of a single polymer, said method comprising: (a) moving said single polymer along an elongation structure, said elongation structure comprising a tapered channel with a first end and a second end, whereby said single polymer is elongated in said tapered channel as said single polymer moves along said tapered channel from said first end to said second end; and (b) determining said length of said single polymer by a method comprising the steps of (i) measuring a first signal amplitude profile of said single elongated polymer at a first detection zone; (ii) measuring a second signal amplitude profile of said single elongated polymer at a second detection zone; (iii) determining a velocity of said single elongated polymer at said first and second detection zones from said first and/or second signal amplitude profiles; and (vi) determining length of said single elongated polymer by multiplying time difference between leading and trailing edges of said first or said second signal amplitude profile with said velocity; wherein each said signal amplitude profile comprises measurements in the respective detection zone of a signal generated at said single elongated polymer at a plurality of times, said plurality of times comprising times that are before and after said elongated polymer is in said detection zone, wherein said plurality of detection zones are located in order along the path of said elongated polymer at predetermined distances, and wherein said first and second signal amplitude profiles are measured in a time-correlated manner. In preferred embodiments, said measuring is performed by a method comprising measuring fluorescence intensity and the first and second signal amplitude profiles are intensity-time curves. In one embodiment, the velocity determined is a center-of-mass velocity. In another embodiment, the velocity determined is a center-to-center velocity. In still another embodiment, the velocity determined is an end-to-end velocity, e.g., a leading-end-to-leading-end velocity or a trailing-end-to-trailing end velocity. In still another embodiment, the velocity determined is a rise-time velocity.

The invention also provides a method for determining length of a single polymer, said method comprising: (a) moving said single polymer along an elongation structure, said elongation structure comprising a central channel holding fluid and a plurality of side channels holding fluid connected to said central channel, said central channel comprising a first end and a second end, wherein said single polymer is moved along said central channel from said first end to said second end and is elongated; and (b) determining said length of said single polymer by a method comprising the steps of (i) measuring a first signal amplitude profile of said single elongated polymer at a first detection zone; (ii) measuring a second signal amplitude profile of said single elongated polymer at a second detection zone; (iii) determining a velocity of said single elongated polymer at said first and second detection zones from said first and/or second signal amplitude profiles; and (vi) determining length of said single elongated polymer by multiplying time difference between leading and trailing edges of said first or said second signal amplitude profile with said velocity; wherein each said signal amplitude profile comprises measurements in the respective detection zone of a signal generated at said single elongated polymer at a plurality of times, said plurality of times comprising times that are before and after said elongated polymer is in said detection zone, wherein said plurality of detection zones are located in order along the path of said elongated polymer at predetermined distances, and wherein said first and second signal amplitude profiles are measured in a time-correlated manner. In preferred embodiments, said measuring is performed by a method comprising measuring fluorescence intensity and the first and second signal amplitude profiles are intensity-time curves. In one embodiment, the velocity determined is a center-of-mass velocity. In another embodiment, the velocity determined is a center-to-center velocity. In still another embodiment, the velocity determined is an end-to-end velocity, e.g., a leading-end-to-leading-end velocity or a trailing-end-to-trailing end velocity. In still another embodiment, the velocity determined is a rise-time velocity.

The invention also provides a method for determining length of a single polymer, said method comprising: (a) moving said single polymer along an elongation structure, said elongation structure comprising a channel with at least one bend, said channel comprising a first end and a second end, wherein said single polymer is moved from said first end to said second end, wherein said single polymer is moved along said channel from said first end to said second end and is elongated; and (b) determining said length of said single polymer by a method comprising the steps of (i) measuring a first signal amplitude profile of said single elongated polymer at a first detection zone; (ii) measuring a second signal amplitude profile of said single elongated polymer at a second detection zone; (iii) determining a velocity of said single elongated polymer at said first and second detection zones from said first and/or second signal amplitude profiles; and (vi) determining length of said single elongated polymer by multiplying time difference between leading and trailing edges of said first or said second signal amplitude profile with said velocity; wherein each said signal amplitude profile comprises measurements in the respective detection zone of a signal generated at said single elongated polymer at a plurality of times, said plurality of times comprising times that are before and after said elongated polymer is in said detection zone, wherein said plurality of detection zones are located in order along the path of said elongated polymer at predetermined distances, and wherein said first and second signal amplitude profiles are measured in a time-correlated manner. In preferred embodiments, said measuring is performed by a method comprising measuring fluorescence intensity and the first and second signal amplitude profiles are intensity-time curves. In one embodiment, the velocity determined is a center-of-mass velocity. In another embodiment, the velocity determined is a center-to-center velocity. In still another embodiment, the velocity determined is an end-to-end velocity, e.g., a leading-end-to-leading-end velocity or a trailing-end-to-trailing end velocity. In still another embodiment, the velocity determined is a rise-time velocity.

The invention also provides a method for determining length of a single polymer, said method comprising: (a) moving said single polymer along an elongation structure, said elongation structure comprising a channel and a plurality of obstacles to motion of said single polymer within said channel, said channel comprising a first end and a second end, wherein said single polymer moves along said channel from said first end to said second end and is elongated; and (b) determining said length of said single polymer by a method comprising the steps of (i) measuring a first signal amplitude profile of said single elongated polymer at a first detection zone; (ii) measuring a second signal amplitude profile of said single elongated polymer at a second detection zone; (iii) determining a velocity of said single elongated polymer at said first and second detection zones from said first and/or second signal amplitude profiles; and (vi) determining length of said single elongated polymer by multiplying time difference between leading and trailing edges of said first or said second signal amplitude profile with said velocity; wherein each said signal amplitude profile comprises measurements in the respective detection zone of a signal generated at said single elongated polymer at a plurality of times, said plurality of times comprising times that are before and after said elongated polymer is in said detection zone, wherein said plurality of detection zones are located in order along the path of said elongated polymer at predetermined distances, and wherein said first and second signal amplitude profiles are measured in a time-correlated manner. In preferred embodiments, said measuring is performed by a method comprising measuring fluorescence intensity and the first and second signal amplitude profiles are intensity-time curves. In one embodiment, the velocity determined is a center-of-mass velocity. In another embodiment, the velocity determined is a center-to-center velocity. In still another embodiment, the velocity determined is an end-to-end velocity, e.g., a leading-end-to-leading-end velocity or a trailing-end-to-trailing end velocity. In still another embodiment, the velocity determined is a rise-time velocity.

The invention also provides a method for determining length of a single polymer, said method comprising: (a) moving said single polymer along an elongation structure, said elongation structure comprising a first channel, said first channel comprising a first end, a second end, and a plurality of posts in a staggered arrangement between said first end and said second end, and a second channel, said second channel comprising a third end and a fourth end, said third end being connected to said first channel at said second end, said second channel decreasing in width from said third end to said fourth end, wherein said single polymer moves along said channel from said first end to said fourth end and is elongated; and (b) determining said length of said single polymer by a method comprising the steps of (i) measuring a first signal amplitude profile of said single elongated polymer at a first detection zone; (ii) measuring a second signal amplitude profile of said single elongated polymer at a second detection zone; (iii) determining a velocity of said single elongated polymer at said first and second detection zones from said first and/or second signal amplitude profiles; and (vi) determining length of said single elongated polymer by multiplying time difference between leading and trailing edges of said first or said second signal amplitude profile with said velocity; wherein each said signal amplitude profile comprises measurements in the respective detection zone of a signal generated at said single elongated polymer at a plurality of times, said plurality of times comprising times that are before and after said elongated polymer is in said detection zone, wherein said plurality of detection zones are located in order along the path of said elongated polymer at predetermined distances, and wherein said first and second signal amplitude profiles are measured in a time-correlated manner. In preferred embodiments, said measuring is performed by a method comprising measuring fluorescence intensity and the first and second signal amplitude profiles are intensity-time curves. In one embodiment, the velocity determined is a center-of-mass velocity. In another embodiment, the velocity determined is a center-to-center velocity. In still another embodiment, the velocity determined is an end-to-end velocity, e.g., a leading-end-to-leading-end velocity or a trailing-end-to-trailing end velocity. In still another embodiment, the velocity determined is a rise-time velocity.

The invention further provides a method for DNA restriction fragment analysis, said method comprising: (a) moving a plurality of DNA molecules along an elongation structure, said elongation structure comprising a first channel, said first channel comprising a first end, a second end, and a plurality of posts in a staggered arrangement between said first end and said second end, and a second channel, said second channel comprising a third end and a fourth end, said third end being connected to said first channel at said second end, said second channel decreasing in width from said third end to said fourth end, wherein said plurality of DNA molecules comprising DNA molecules generated by one or more restriction enzymes, and wherein each of said plurality of DNA molecules moves along said channel from said first end to said fourth end, separates from other DNA molecules in said plurality, and is elongated; and (b) measuring length of each of said plurality of DNA molecules by repeating for each of said plurality of DNA molecules a method comprising: (i) measuring a first signal amplitude profile of a DNA molecule in said plurality of DNA molecules at a first detection zone and a second signal amplitude profile of said DNA molecule at a second detection zone; (ii) determining a velocity of said DNA molecule at said first and second detection zones from said first and/or second signal amplitude profiles; and (iii) determining length of said DNA molecule by multiplying time difference between leading and trailing edges of said first or said second signal amplitude profile with said velocity; wherein each said signal amplitude profile comprises measurements in the respective detection zone of a signal generated at said DNA molecule at a plurality of times, said plurality of times comprising times that are before and after said DNA molecule is in said detection zone, wherein said plurality of detection zones are located in order along said second channel at predetermined distances, and wherein said first and second signal amplitude profiles are measured in a time-correlated manner.

4. BRIEF DESCRIPTION OF FIGURES

FIG. 1 shows a schematic illustration of the method of the invention. 101 detection zone 1; 102 detection zone 2; 103 detection zone 3; 104 flow channel; 105 an elongated polymer; 106 signal amplitude profile measured at detection zone 1; 107 signal amplitude profile measured at detection zone 2; 108 signal amplitude profile measured at detection zone 3; D1 distance between detection zone 1 and detection zone 2; D2 distance between detection zone 2 and detection zone 3; W dimension of detection zones.

FIG. 2A–2C show a schematic illustration of time-correlated signal amplitude profiles and types of velocities. 201 first signal amplitude profile; 202 second signal amplitude profile; 203 center-to-center velocity; 204 center-of-mass velocity; 205 rise-time velocity; 206 end-to-end velocity; 207–210 signal amplitude profiles measured by multiple detection zones; 211 signal detected at a first detection zone; 212 signal detected at a second detection zone.

FIG. 3 shows examples of various structures that fall within the scope of the invention.

FIGS. 4a–4m show (a) several embodiments of stretching structures involving funnels, posts, branches, and serial structures; (b) an enlarged example of two-funnel structures with posts in serial; (c) several embodiments of complex post arrangements and branched structures; (d) an embodiment of a structure containing serial and parallel structures; (e) an asymmetric branched structure; (f) a structure having a combination of small obstacles which define small gaps; (g) a structure having a combination of polygons, bars, and posts; (h) an asymmetric bent structure; (i) an enlarged view of a branched structure having posts; (j) a large funnel structure with support posts; (k) a funnel structure with posts; (l) funnel structures with a linear increase in flow rate with and without posts; and (m) a summary of some of the funnel structures encompassed by the present invention.

FIG. 5. shows an embodiment of a tapered channel of linear decreasing width.

FIG. 9 shows an embodiment of a branched channel structure in which the elongational force comes from both a narrowing channel and the presence of side channels.

FIG. 10(a) shows the "racetrack effect" of fluid on the outside of a bend taking longer to pass around the corner than fluid on the inside; (b) shows how the "racetrack effect" can lead to the uncoiling of a polymer in a bend.

Figure 11:
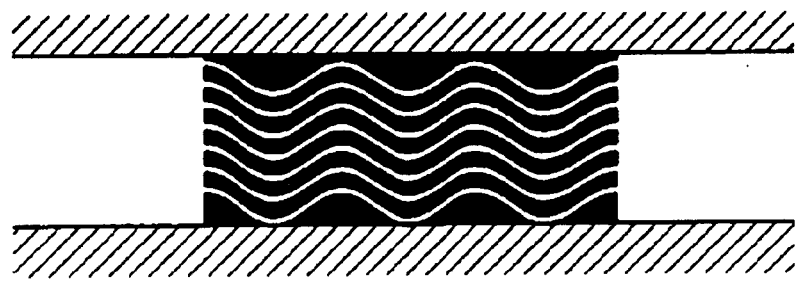

FIG. 11 displays an embodiment of the tortuosity regime, in which the channels follow a sine wave shape.

Figure 12:
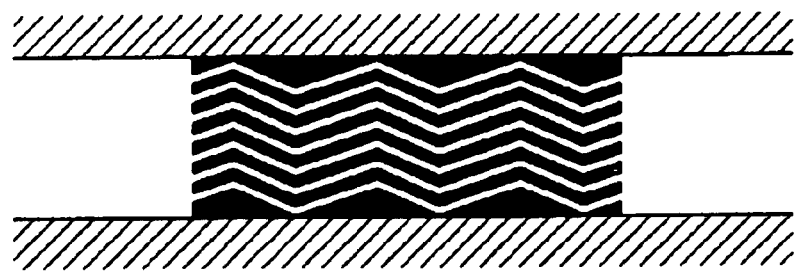

FIG. 12 displays an embodiment of the tortuosity regime in which the channels follow a zig-zag shape.

Figure 13:
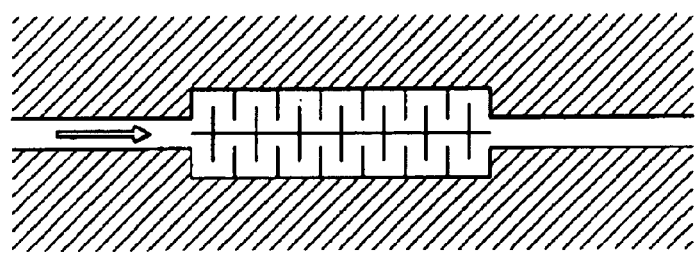

FIG. 13 displays an embodiment of the tortuosity regime in which the channels follow right angles in a "snake" shape.

Figure 14:
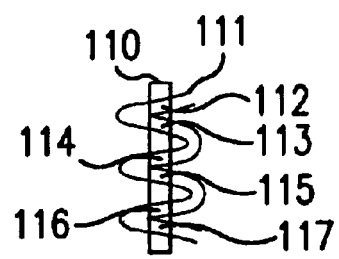

FIG. 14 shows how a tortuous channel can be used for multiple detection of the same polymer as it travels down a channel.

Figure 15:
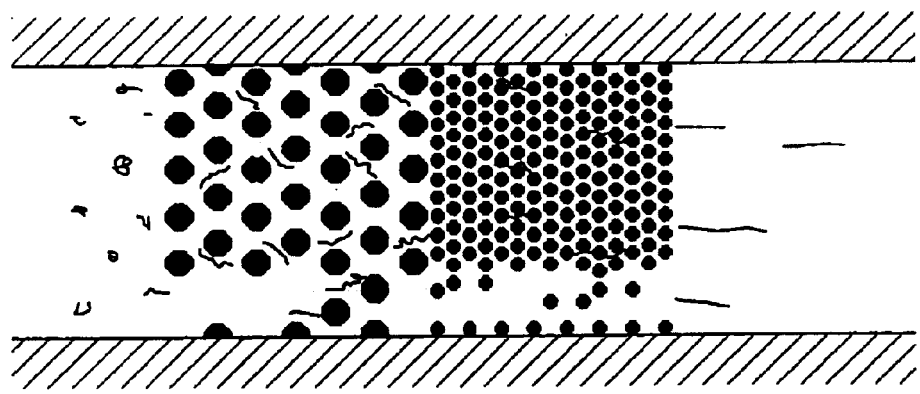

FIG. 15 shows how a polymer can stretch in an embodiment of the obstacle field regime with gradated sizing of obstacles.

Figure 16:
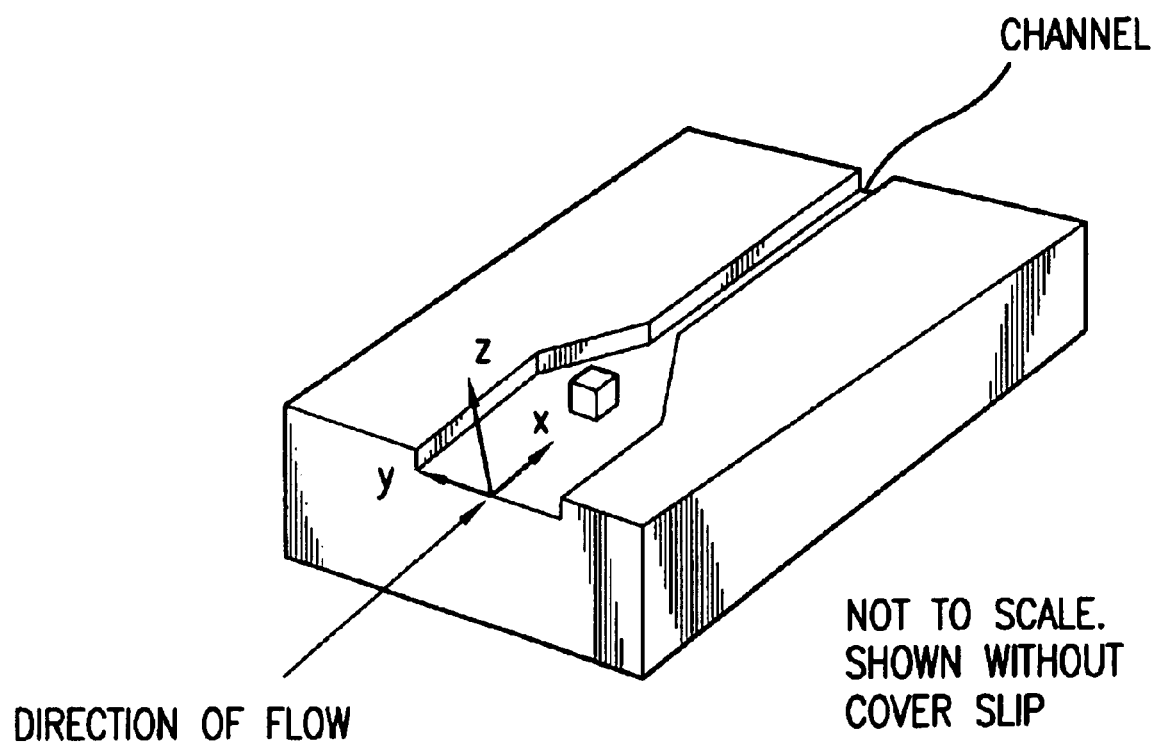

FIG. 16 shows the coordinate frame for an elongation structure.

Figure 17A:
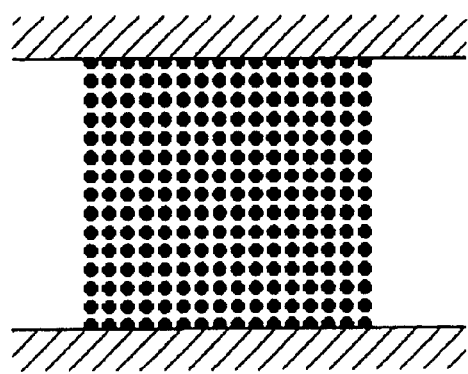

FIG. 17(a) shows an embodiment of the obstacle field regime with square-grid alignment of circular obstacles; (b) shows an embodiment of the obstacle field regime with an offset-grid alignment of circular obstacles.

Figure 18:
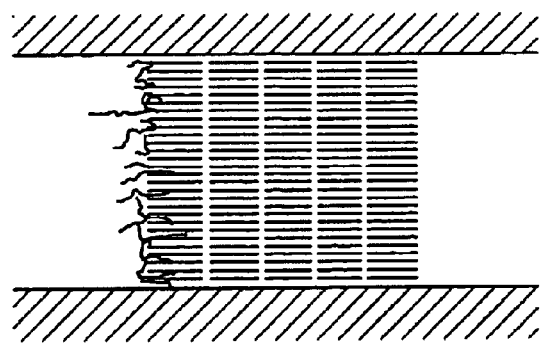

FIG. 18 shows an embodiment of the obstacle field regime with close spacing of rectangular obstacles of an exaggerated aspect ratio.

Figure 19:
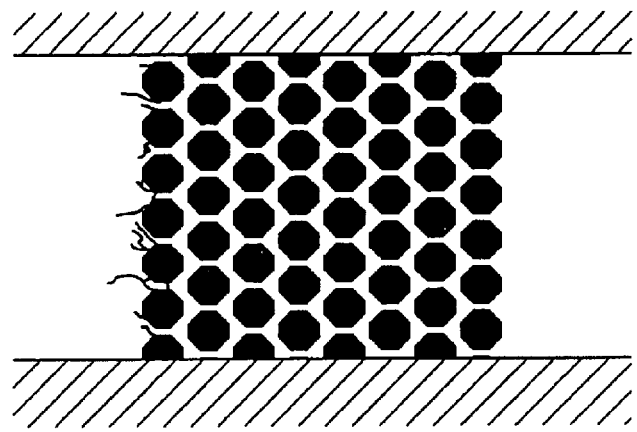

FIG. 19 shows an embodiment of the obstacle field regime with close spacing of circular obstacles.

Figure 20:
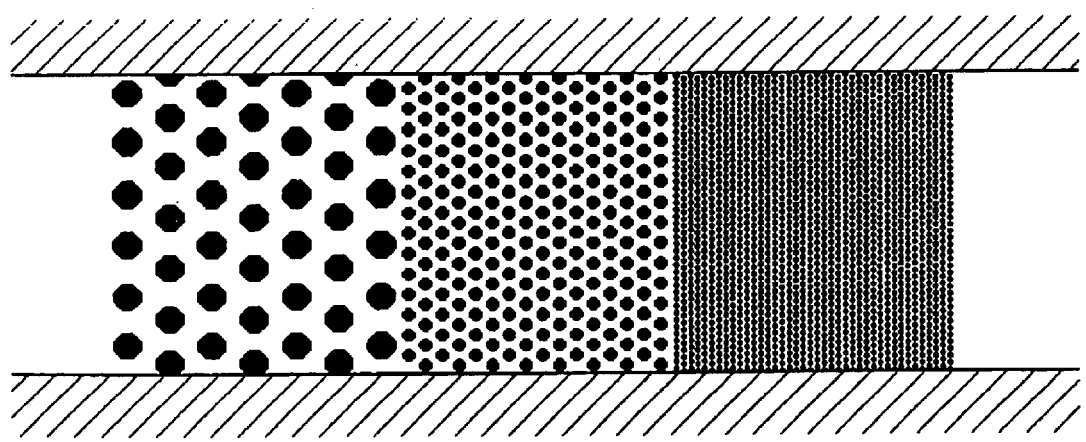

FIG. 20 shows an embodiment of the obstacle field regime with three gradated sizes of circular obstacles.

Figure 21:
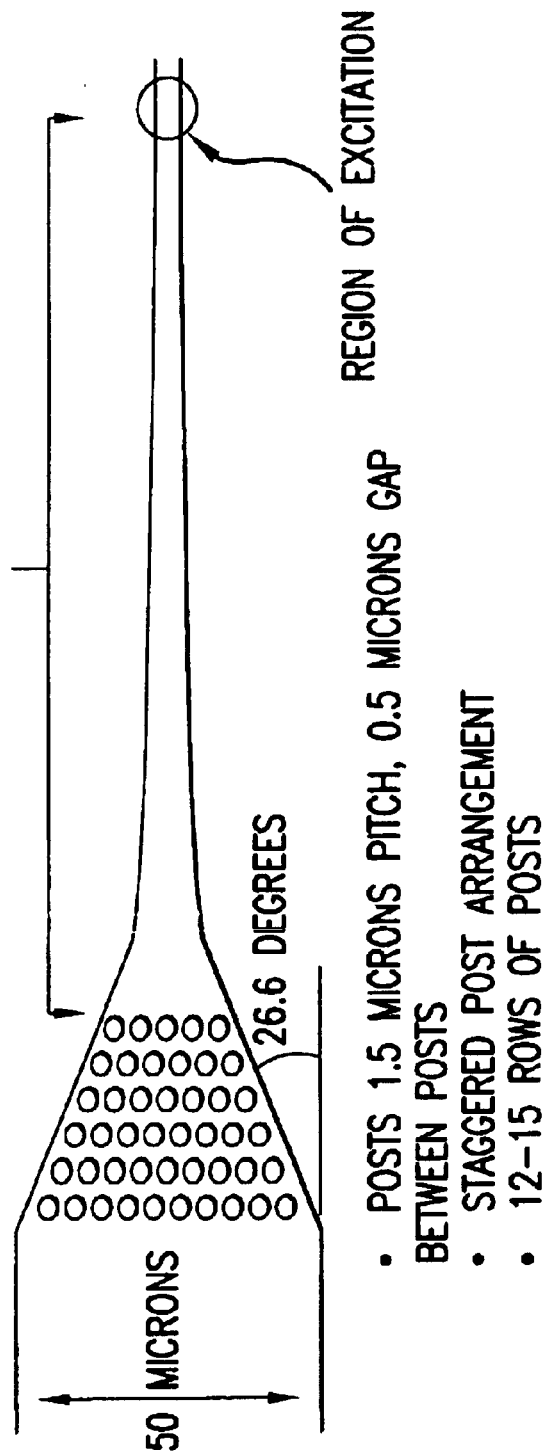

FIG. 21 shows a configuration for consistent unraveling, delivery, and stretching of DNA of varying sizes.

Figure 22:
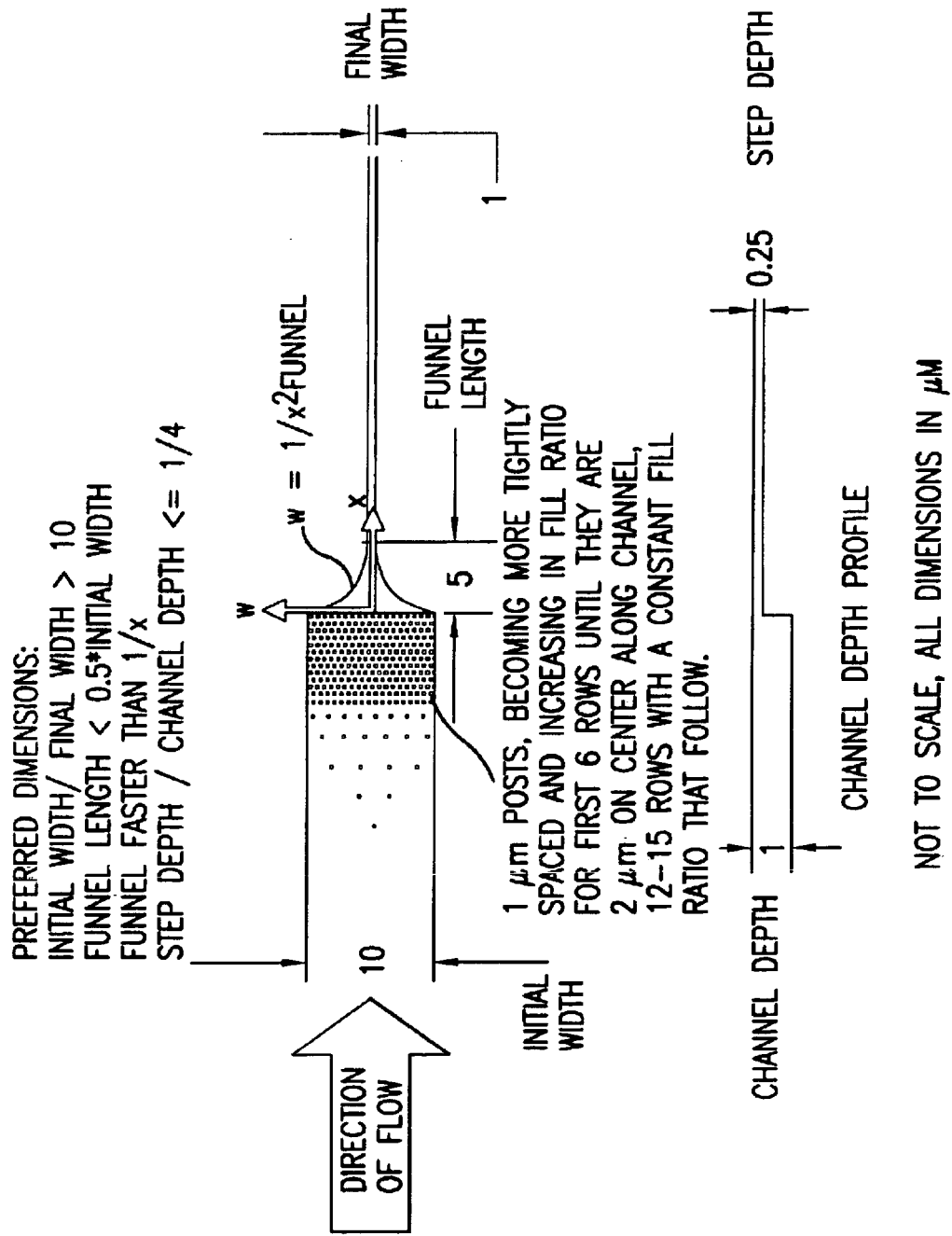

FIG. 22 shows a configuration of a preferred embodiment of a structure for stretching DNA that combines a post field, a funnel that tapers as $1/x^2$, wherein x is the distance along the length of the funnel, and a step that reduces the channel depth.

Figure 23:
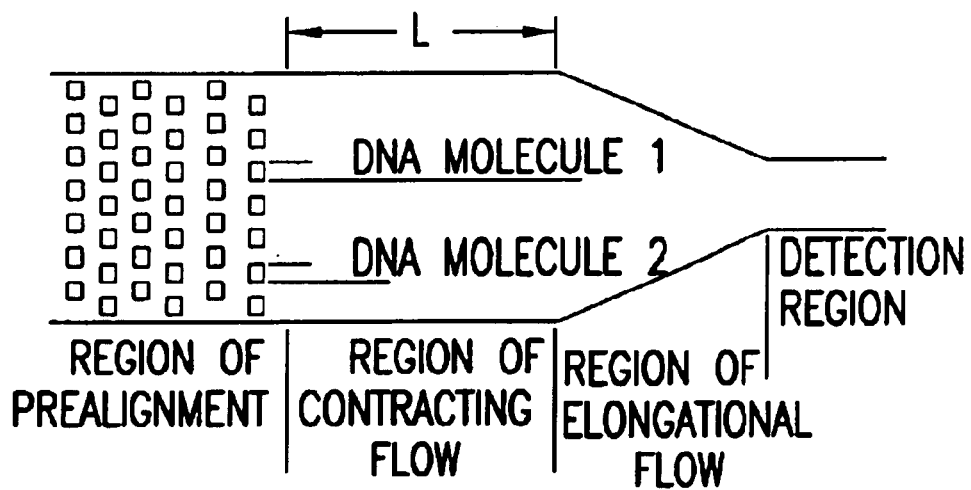

FIG. 23 shows a schematic of a molecular size sorting device, wherein signals of molecules of length L or greater can be easily distinguished from signals of molecules of length less than L.

Figure 24:
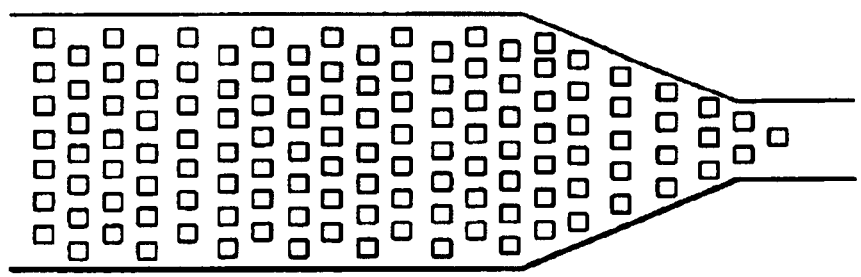

FIG. 24 shows a schematic of a device that stretches molecules of all lengths, such that signals from all of them are uniformly detected.

Figure 25:
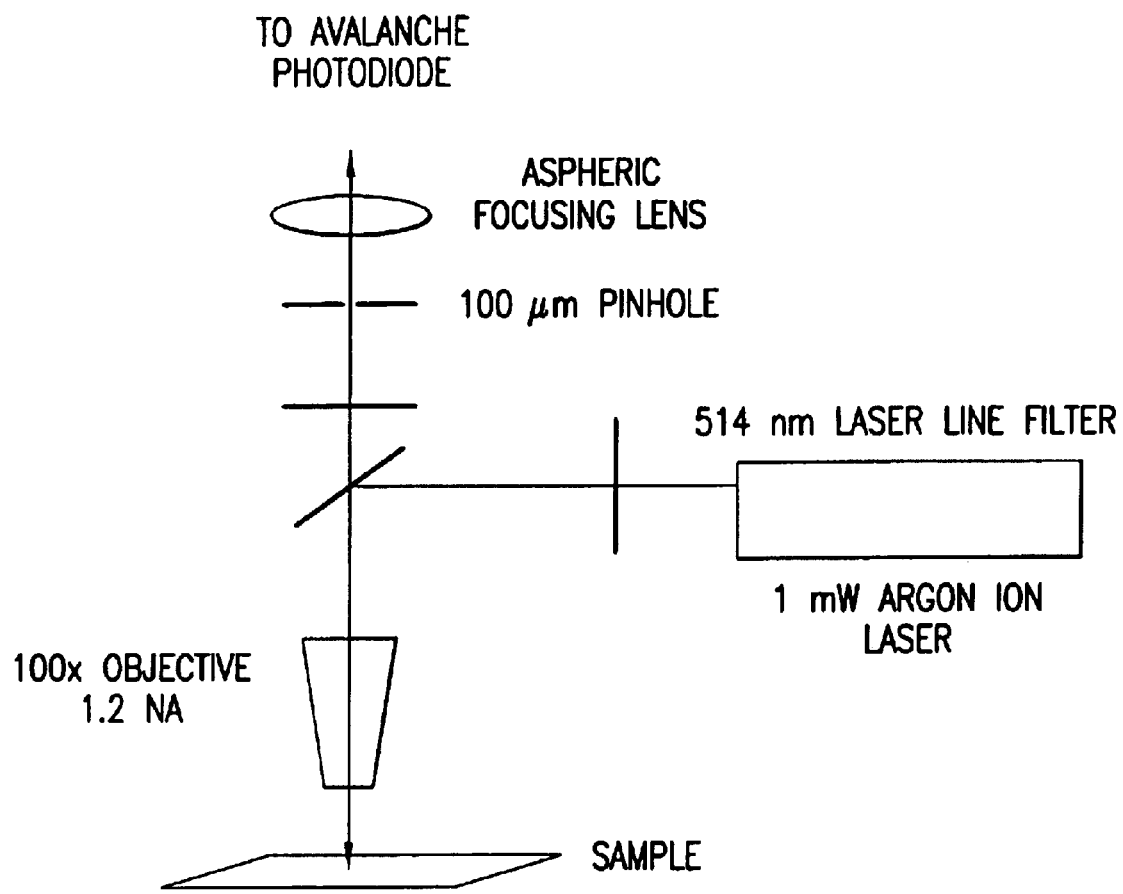

FIG. 25 shows a sensitive optical apparatus that utilizes confocal fluorescence illumination and detection.

Figure 26:
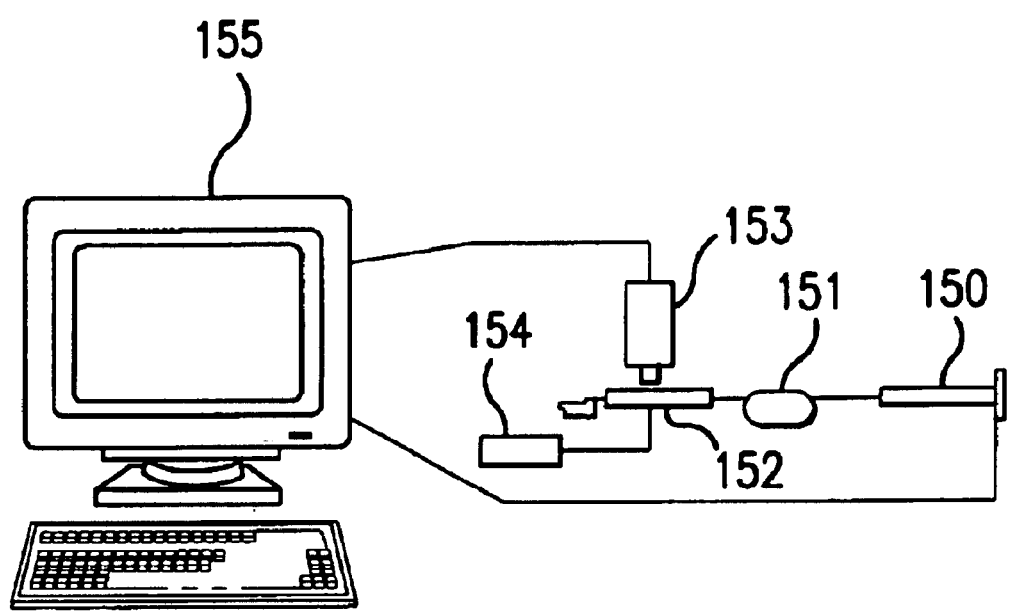

FIG. 26 demonstrates one embodiment of the overall polymer analysis system.

Figure 27:
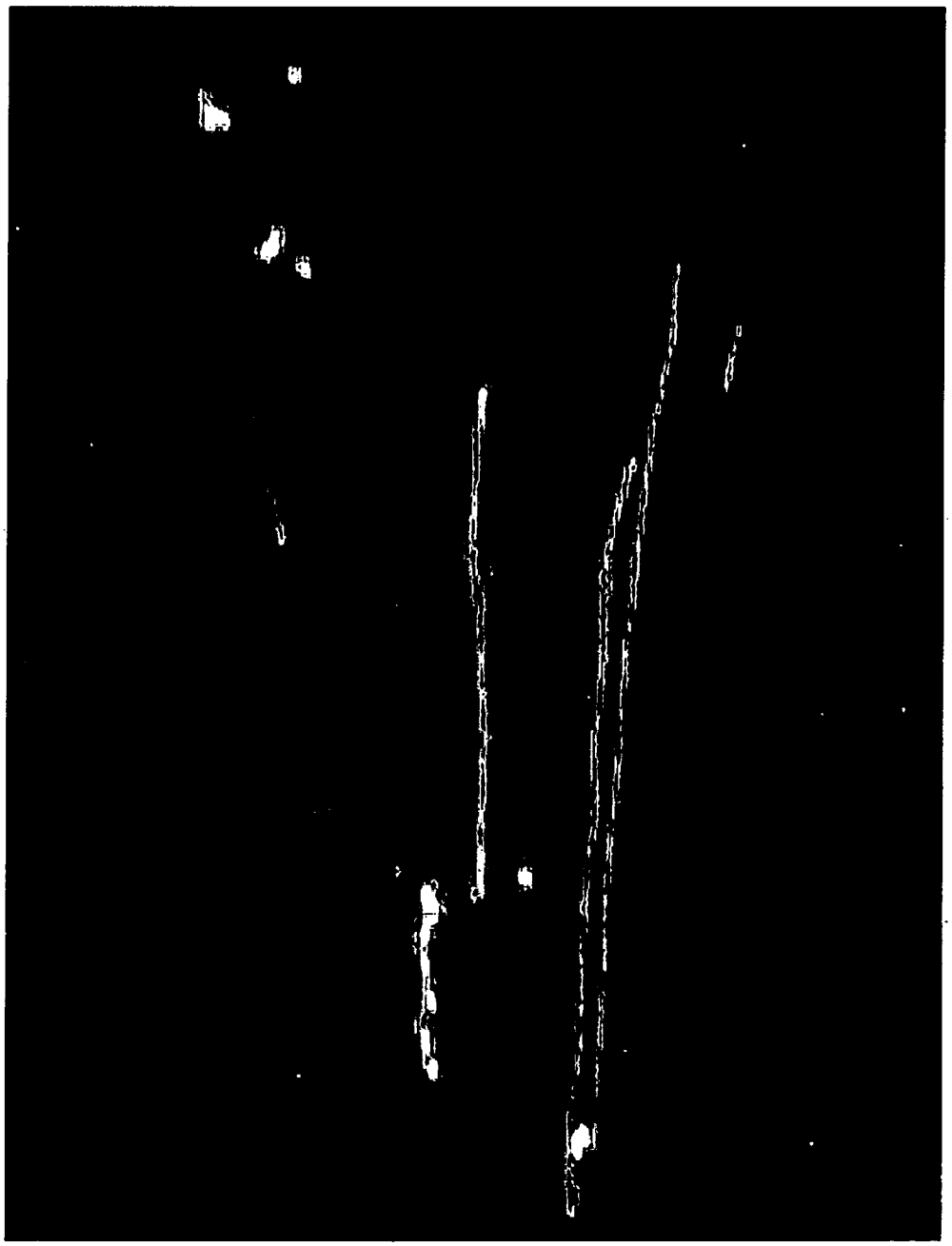
Figure 28A:
Figure 28B:
Figure 28C:
Figure 28D:
Figure 28E:
Figure 28F:
Figure 28G:

FIG. 27 shows DNA in various stretching states in the entrance to a tapered channel of constant strain rate.

FIG. 28(a–g) show a 50 kb DNA being stretched out in a tapered channel.

Figure 29:
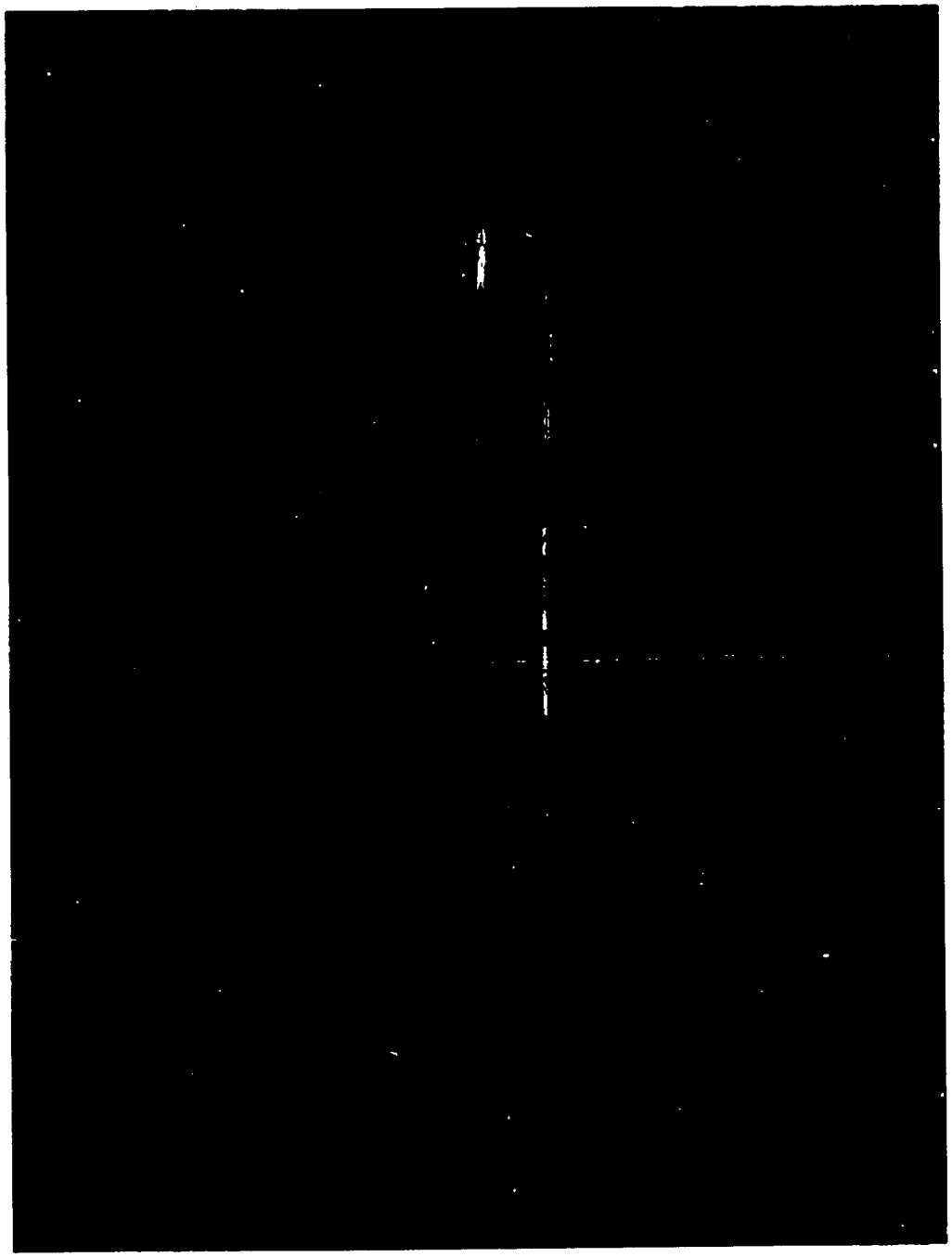

FIG. 29 shows a DNA measured at 537 kb stretched out in a channel.

Figure 30:
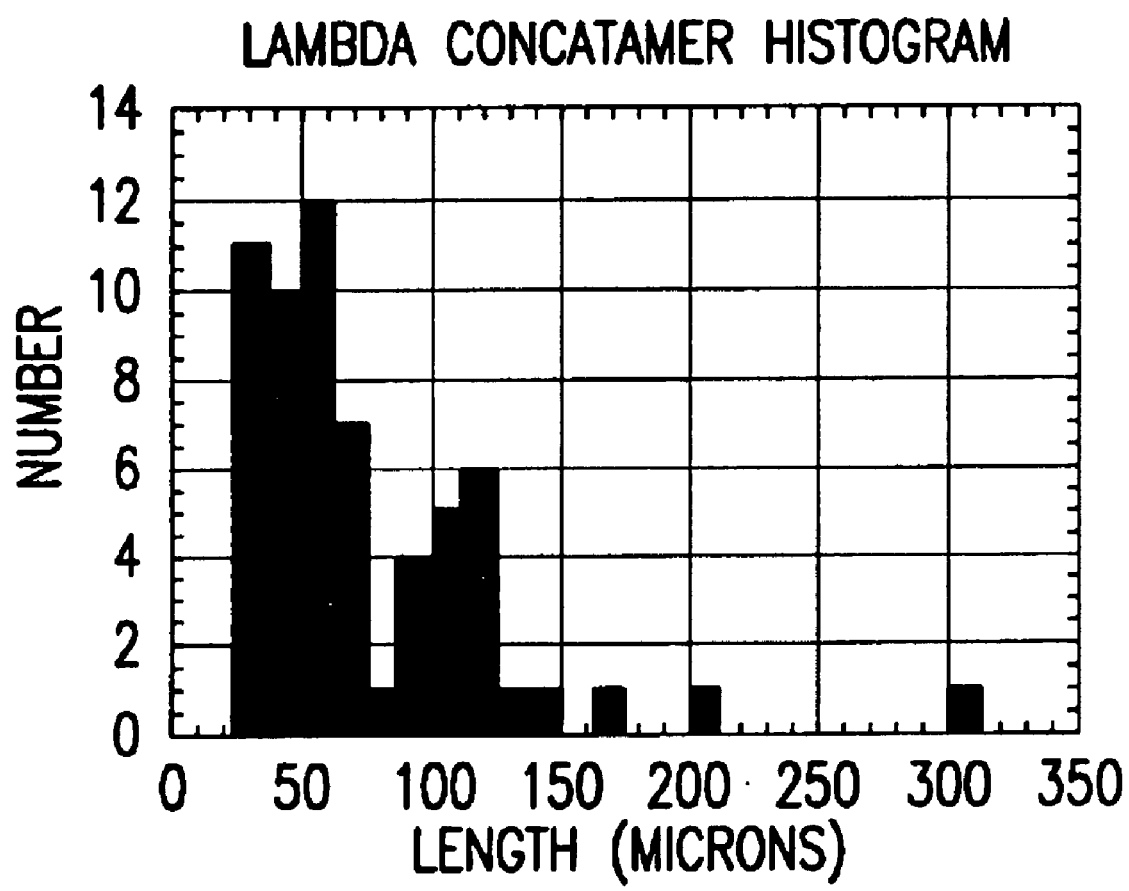

FIG. 30 shows a histogram displaying experimentally determined DNA lengths.

FIG. 31 shows histograms of experimentally determined lengths of phage lambda DNA from the structure of FIG. 21(a) without posts, and (b) with posts.

FIG. 32 is a schematic illustration of an embodiment for formation of multiple spots.

Figure 33:
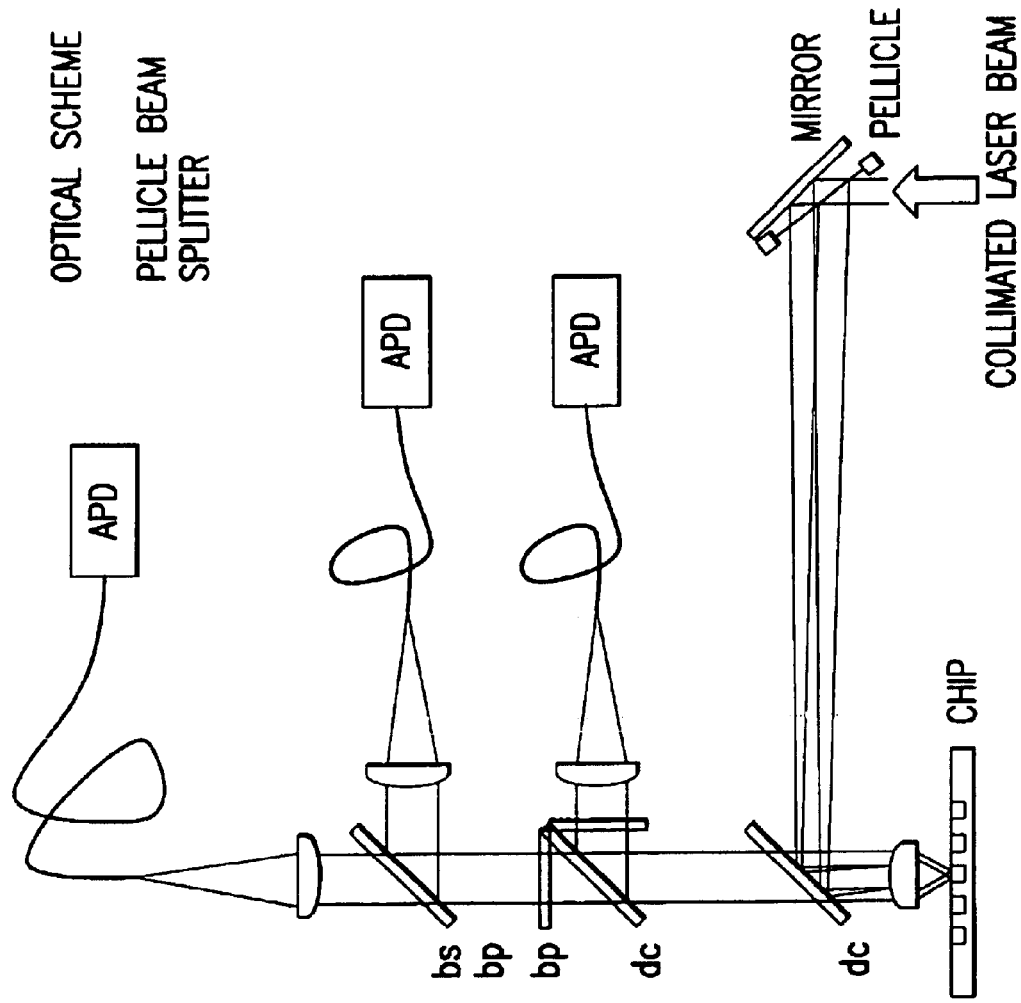

FIG. 33 illustrates an embodiment employing beamsplitter to generate two laser spots. APD: avalanche photodiode; bs: beamsplitter; bp: band-pass filter; dc: dichroic mirror.

Figure 34:
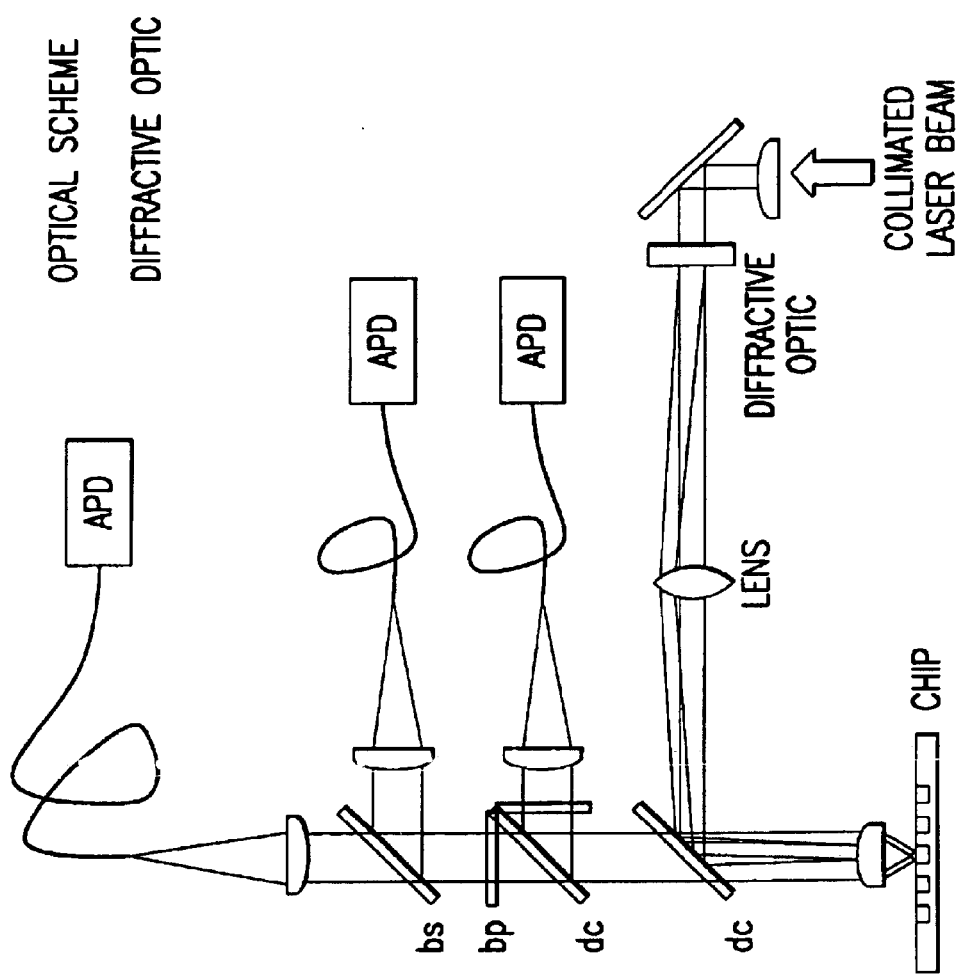

FIG. 34 illustrates an embodiment employing a diffractive grating to generate two laser spots. APD: avalanche photodiode; bs: beamsplitter; bp: band-pass filter; dc: dichroic mirror.

Figure 35:
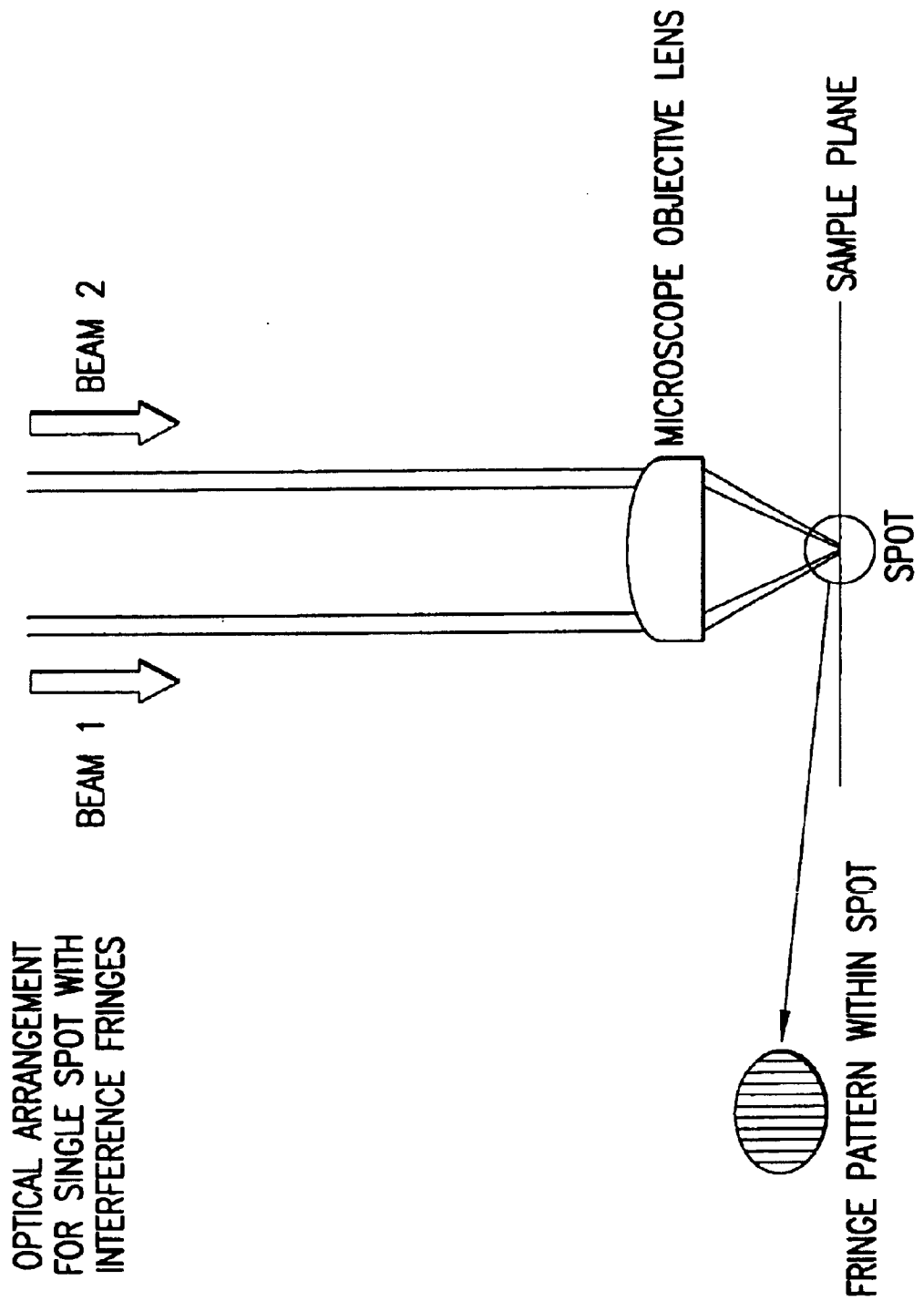

FIG. 35 illustrates an embodiment to generate interference fringes.

Figure 36:
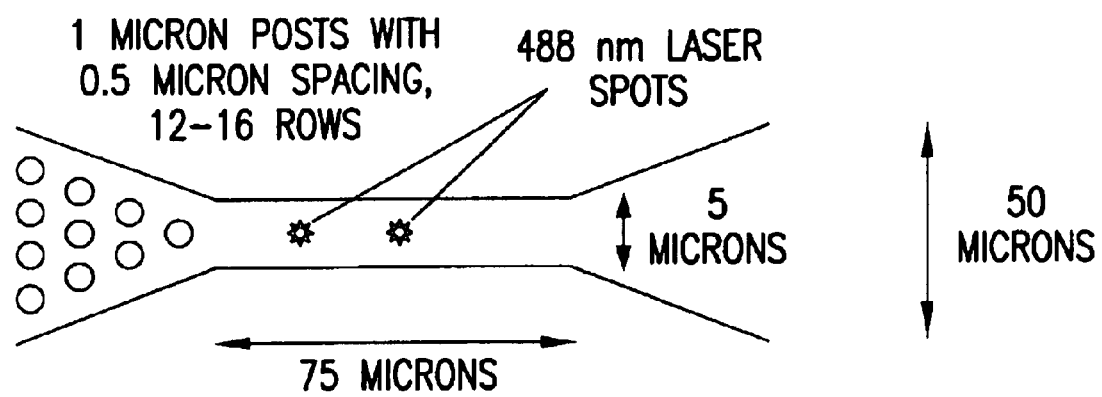

FIG. 36 illustrates an experiment setup.

Figure 37A:
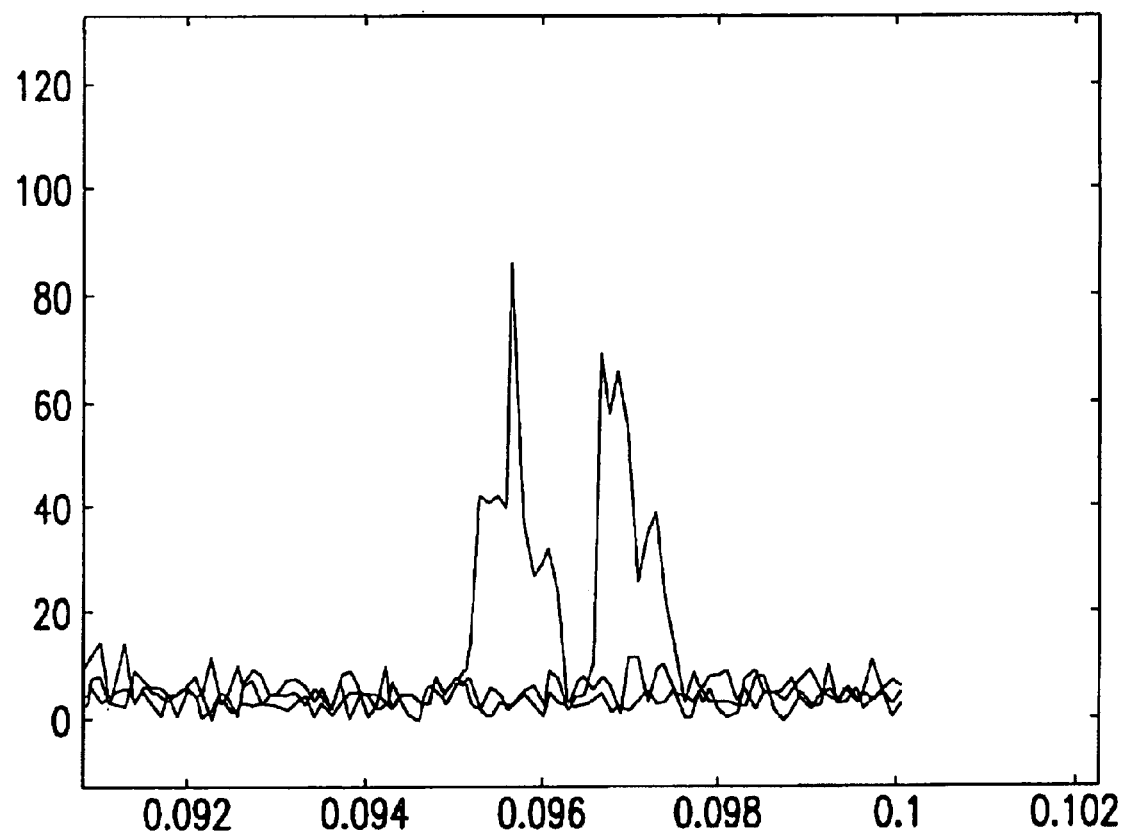
Figure 37B:
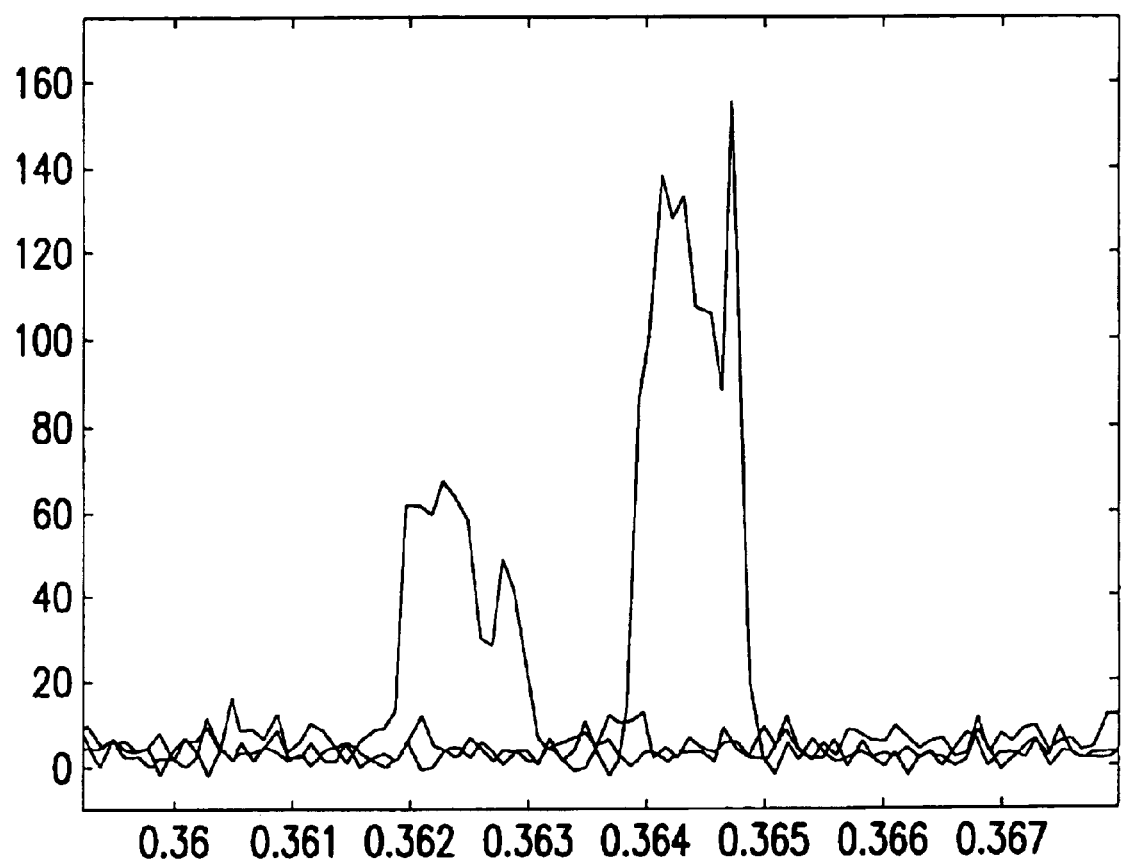
Figure 37C:
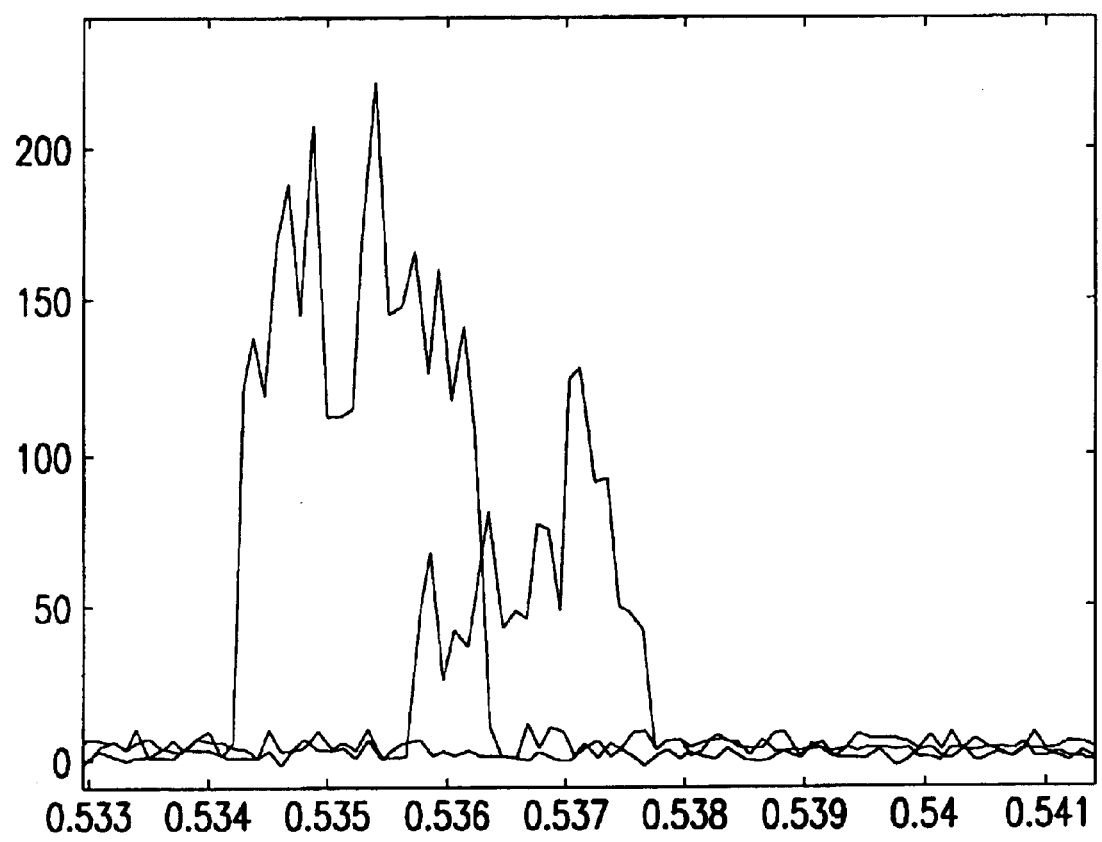

FIGS. 37A–37C show exemplary signal amplitude profiles measured at two detection zones.

Figure 38:
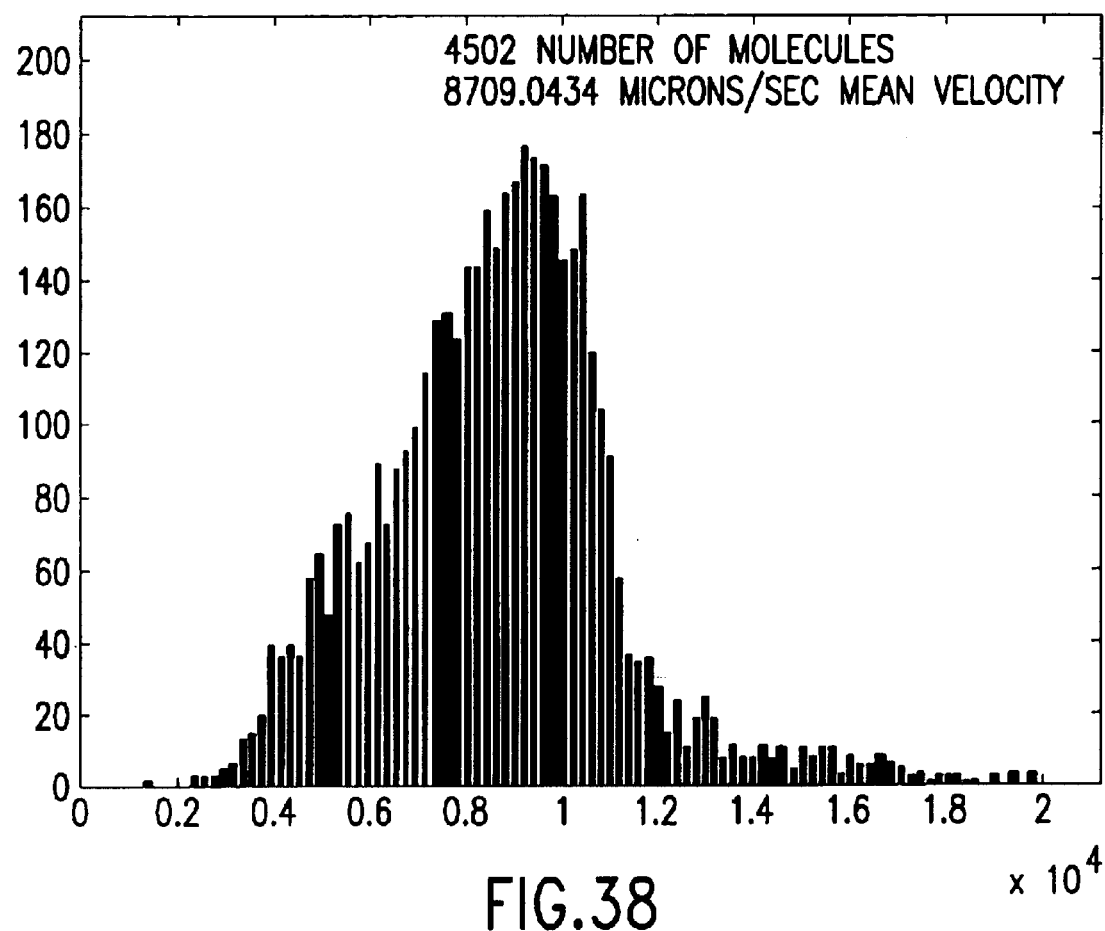

FIG. 38 shows a velocity histogram COM velocity of a population of λ DNA molecules measured by the method of the invention.

Figure 39:
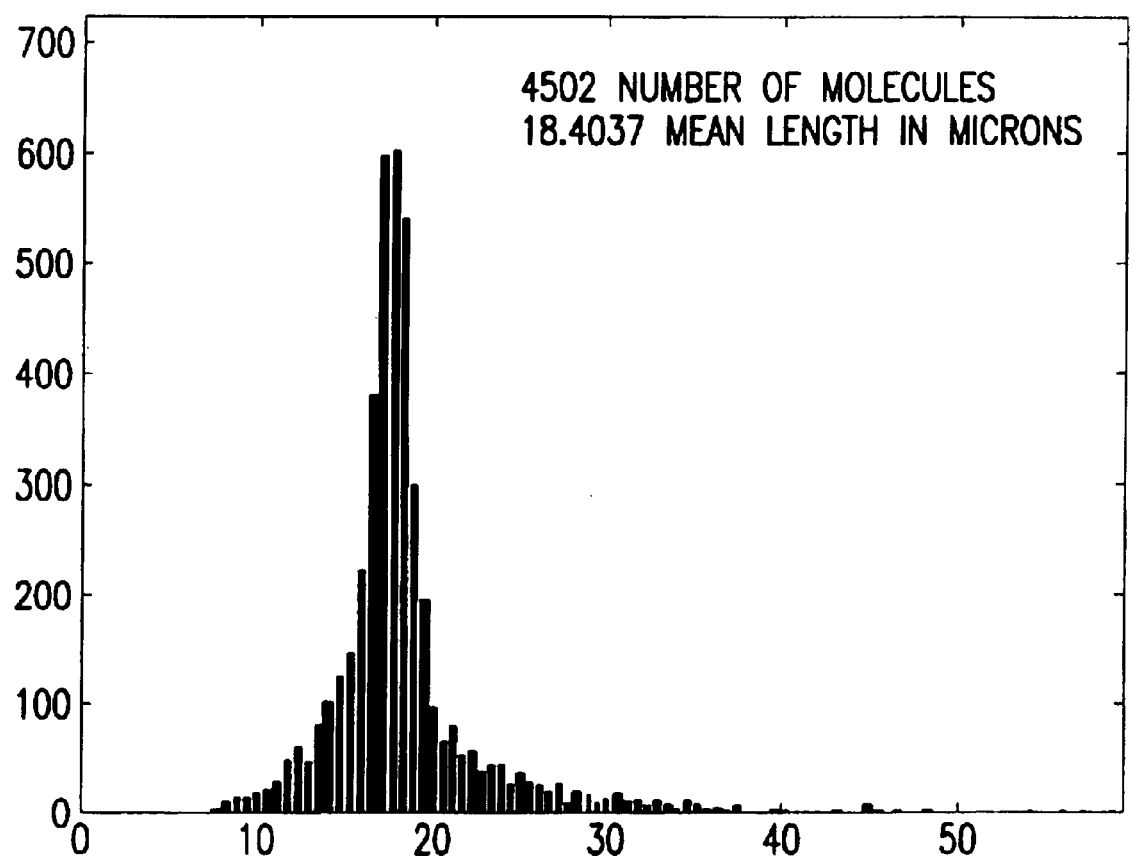

FIG. 39 shows a length histogram of a population of X DNA molecules measured by the method of the invention.

5. DETAILED DESCRIPTION OF THE INVENTION

Figure 1:
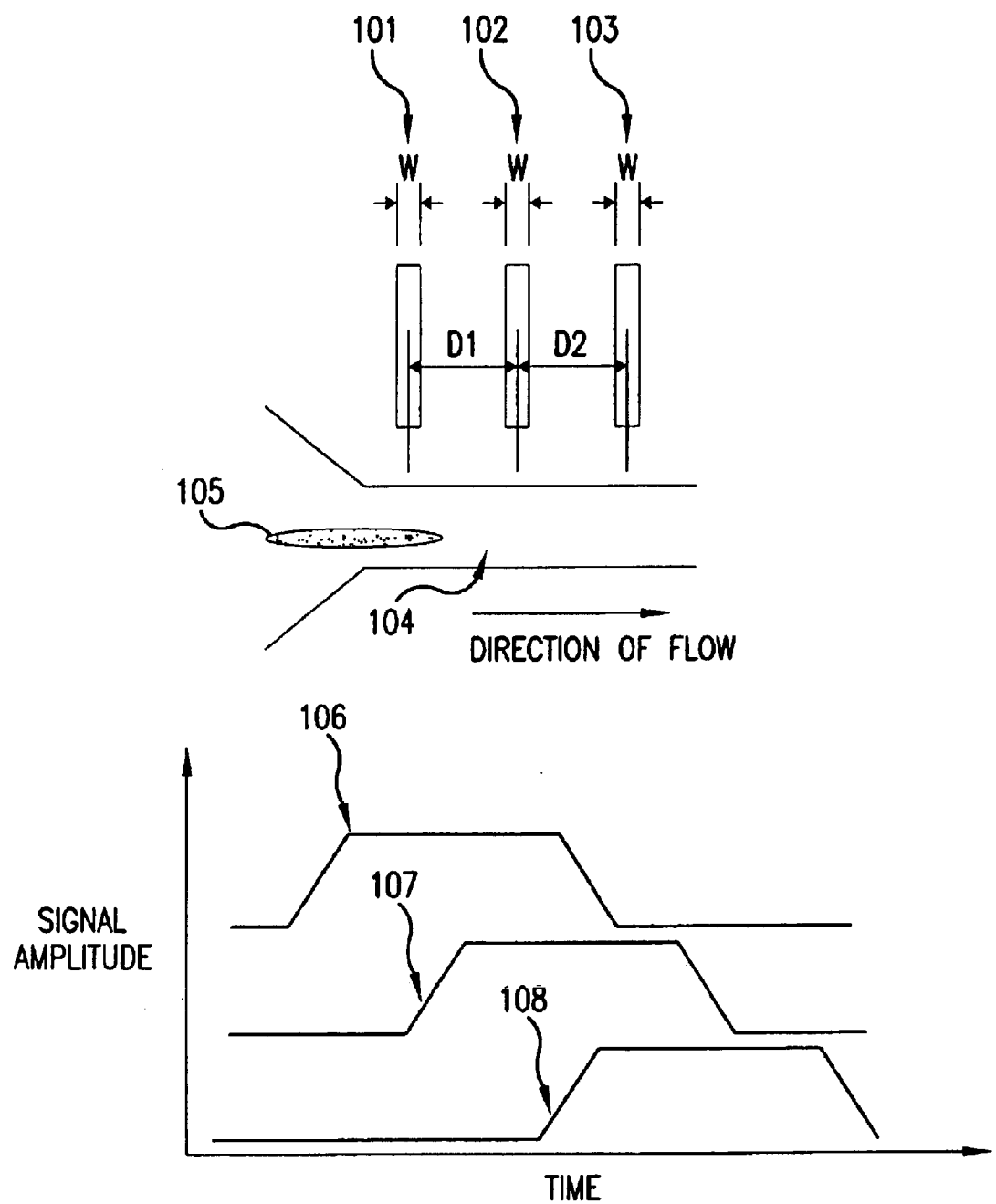

The present invention provide methods and apparatuses for determining the velocities of single elongated macromolecules. The methods of the invention are based on time-correlated measurements of an elongated macromolecule at each of a plurality of detection zones. The detection zones are located along the travel path of the elongated macromolecule at predetermined spacings. Signal amplitude profiles, e.g, intensity-time curves when fluorescence based measurements are used, of an elongated macromolecule are measured as the macromolecule passes through each of the detection zones. The measurements in the plurality of detection zones are time-correlated, e.g., synchronized, so that the temporal spacings between signal amplitude profiles measured at different detections zones are also determined. A schematic illustration of the methods of the invention is presented in FIG. 1. FIG. 1 illustrates measured signal amplitude profiles that are positive, i.e., an increasing signal amplitude. It will be apparent to one skilled in the art that negative signal amplitude profiles are also encompassed. For example, when absorption based measurements are used, the signal amplitude will decrease when the polymer is in the detection zone.

As used herein, the term "elongated macromolecule" or "stretched macromolecule" refers to a macromolecule that is in a conformation in which the length of the molecule is substantially greater than its radius of gyration in the same solvent. Preferably the elongated macromolecule has a length which is substantially close to its contour length.

As used herein, a "detection zone" refers to a region or volume along the traveling path of a macromolecule in which a signal from the macromolecule is measured if the macromolecule, or a portion thereof, is present in the region or volume. In embodiments based on measuring laser induced fluorescence, a detection zone is defined by the excitation volume of a laser beam and the signal is total fluorescence intensity emitted by the macromolecule or a portion thereof in the excitation volume.

As used herein, "time-correlated measurements" in more than one detection zone refers to measurements performed in different detection zones in such a manner that the temporal spacings between measured signals in different detections zones are known. Such time-correlated detection can be achieved by synchronizing measurements in all detection zone in real time. Alternatively, measurements in different detection zones may be time-correlated by fixed, known time delay of detection in different detection zones. Methods for synchronized and time-delayed detection in different detection zones are well known in art and will be apparent to one skilled in art.

As used herein, a "signal amplitude profile" refers to the temporal profile of a measured signal. In embodiments involving optical detection, e.g., when macromolecules are detected by fluorescence, the signal amplitude profile is the intensity vs. time curve or intensity-time curve measured by a photodetector. Preferably, the contributions to a signal amplitude profile due to the finite size of a detection zone are eliminated. In embodiments involving laser excitation, the laser beam profile is preferably deconvoluted from a measured intensity-time curve. Methods for eliminating the contribution of the finite size of a detection zone to a signal amplitude profile, e.g., a laser beam profile, is well known in art and can be performed by one skilled in the art.

The present invention also provides methods and structures that allow polymers of any length, including nucleic acids containing entire genomes, to be stretched or elongated for further analysis, e.g., determination of their velocities and lengths. Polymers are loaded into a device and run through the structures, propelled by, inter alia, physical, electrical or chemical forces. Stretching or elongation is achieved, e.g., by applying elongational forces on the polymers via generating elongational flows with large enough strain rates, by placing obstacles in the path of the polymer, or by any combination thereof. The structures of the invention permit stretching out polymers to lengths that are equal to or greater than the active area of the apparatus, i.e., where properties of the polymers are measured. For example, if a detection zone is in a region along the path of elongated polymers in which elongation or stretching occurs, an elongated polymer, e.g., an elongated DNA molecule, of lengths much longer than the dimension of the detection zone can be measured. Since multiple molecules may be stretched in succession, extremely high throughput screening, e.g., screening of more than one molecule per second, can be achieved.

In the invention, single extended, labeled polymers move past the detection zones, at which labeled units of the polymers interact with the detector to produce a signal. As used in this application, "move past" refers to embodiments in which the detection zones are stationary and the extended polymers are in motion, or the detection zones are in motion and the extended polymers are stationary, or the detection zones and extended polymers are both in motion.

Although the invention may be used for characterizing any polymer, it is preferable that the polymers have a predominantly, though not necessarily exclusively, linear or single-chain arrangement. Examples of such polymers include biological polymers such as deoxyribonucleic acids, ribonucleic acids, polypeptides, and oligosaccharides. The polymers may be heterogeneous in backbone composition, thereby containing any possible combination of individual monomer units linked together, e.g., peptide-nucleic acids (PNA), which have amino acids linked to nucleic acids. In a preferred embodiment, the polymers are homogeneous in backbone composition and are, e.g., nucleic acids, polypeptides or oligosaccharides. The term "backbone" is given its usual meaning in the field of polymer chemistry. A nucleic acid as used herein is a biopolymer comprised of nucleotides, such as deoxyribose nucleic acid (DNA) or ribose nucleic acid (RNA). A protein or polypeptide as used herein is a biopolymer comprised of amino acids. In the most preferred embodiment, the extended object is a double-stranded DNA molecule.

A polymer is made up of a plurality of individual units, i.e., monomeric units or monomers, which are building blocks that are linked either directly or indirectly to other building blocks or monomers to form the polymer. The polymer preferably comprises at least two chemically distinct linked monomers. The at least two chemically distinct linked monomers may produce or be labeled to produce different signals. Different types of polymers are composed of different monomers. For example, DNA is a biopolymer comprising a deoxyribose phosphate backbone to which are attached purines and pyrimidines such as adenine, cytosine, guanine, thymine, 5-methylcytosine, 2-aminopurine, hypoxanthine, and other naturally and non-naturally occurring nucleobases, substituted and unsubstituted aromatic moieties. RNA is a biopolymer comprising a ribose phosphate backbone to which are attached purines and pyrimidines such as those described for DNA but wherein uracil is substituted for thymidine. Deoxyribonucleotides may be joined to one another via an ester linkage through the 5' or 3' hydroxyl groups to form the DNA polymer. Ribonucleotides may be joined to one another via an ester linkage through the 5', 3' or 2' hydroxyl groups. Alternatively, DNA or RNA units having a 5', 3' or 2' amino group may be joined via an amide linkage to other units of the polymer.

The polymers may be naturally-occurring or non-naturally occurring polymers. Polymers can be isolated, e.g., from natural sources using biochemical purification techniques. Alternatively, polymers may be synthesized, e.g., enzymatically by in vitro amplification using the polymerase chain reaction (PCR), by chemical synthesis, or by recombinant techniques.

The structures of the invention are used in conjunction with methods for analyzing the extended polymers by detecting a physical quantity which transmits or conveys information about the structural characteristics of an extended polymer. A physical quantity, as used herein, can either be a measurable intrinsic property of a particular type associated with one or more monomers of an extended polymer, e.g., the distinct absorption maxima of the naturally occurring nucleobases of DNA (the polymer is intrinsically labeled), or a measurable property of a compound that is specifically associated with one or more monomers of an extended polymer (the polymer is extrinsically labeled).

Preferably the physical quantity is proportional to the number of monomers in the detection zone. An extrinsically labeled polymer may be labeled with a particular fluorescent dye with which all nucleobases of a particular type, e.g., all thymine nucleobases, in a DNA strand are labeled. Alternatively, an extrinsically labeled polymer may be a fluorescently labeled oligonucleotide of defined length and sequence that hybridizes to and therefore "marks" the complementary sequence present in a target DNA. Molecules, or markers, that can be used to labeled polymers may further include, but are not limited to, sequence specific major or minor groove binders and intercalators, sequence-specific DNA or peptide binding proteins, sequence specific PNAs, etc. The detectable physical quantity may be in any form that is capable of being measured. For instance, the detectable physical quantity may be electromagnetic radiation, electrical conductance, heat conductance, radioactivity, etc. The measured signal may arise from energy transfer, directed excitation, quenching, changes in conductance (resistance), or any other physical changes. In one embodiment, the measured signal arises from fluorescence resonance energy transfer ("FRET") between the marker and the station, or the environment surrounding the station. In preferred embodiments, the measured signal results from direct excitation in a confined or localized region, or epiillumination of a confocal volume or a slit-based excitation. Possible analyses of polymers include, but are not limited to: determination of polymer length, determination of polymer sequence, determination of polymer velocity, determination of the degree of identity of two polymers, determination of characteristic patterns of unit-specific markers of a polymer to produce a "fingerprint", and characterization of a heterogeneous population of polymers using a statistical distribution of unit-specific markers within a sample population. The exemplary labels include but are not limited to intercalator dyes: YOYO-1, TOTO-1, YOYO-3, TOTO-3, POPO-1, POPO-3, JOJO-1, JOJO-3, BOBO-1, BOBO-3 (from molecular probes); non-intercalator/backbone staining dyes (these dyes chemically attach to the backbone of DNA): Panvera-fluorescein kit, Panvera-Cy3 kit, Panvera-Cy 5 kit; fluorescent probe dyes: fluorescein, tetramethylrhodamine, Alexa dyes, Oregon dyes, Cy dyes, IR dyes; and other types of labels, e.g., latex spheres, gold particles, and streptavidin-biotin conjugates.

There are numerous methods and products available for analyzing polymers as described in PCT Publication No. WO 98/35012, which is incorporated herein by reference in its entirety.

Various methods for analyzing polymers differ in their potential sensitivity and resolution, e.g., the minimum distance between two detection zones. A low resolution technique is capable of measurements in two detection zones having a large distance between them, a high resolution technique is capable of measurements in two detection zones having a smaller distance between them. The resolution of a particular technique is determined by the characteristic distance through which the detection method may sense the particular physical quantity of an extended polymer. For example, the resolution of optical methods is dictated by the diffraction limit.

In the following, for simplicity reasons, optical detection methods are often used. It will be apparent to one skilled in the art that other detection methods can be used in conjunction or in place of optical detections.

5.1 Velocities of Single Elongated Polymers

Due to its flexibility, the conformation of a polymer may be constantly changing. As a consequence, each point on the polymer may have a different velocity from another point on the polymer. For polymers in a fluid flow, the velocity of an elongated polymer is also affected by the fluid flow. The velocity of a single elongated polymer can be described in various manners (FIG. 2).

The velocity of an elongated polymer can be represented by the velocity of its center-of-mass (COM). The COM velocity can be measured by determining the time interval the center-of-mass of the elongated polymer requires to travel between two detection zones of known distance. The center-of-mass velocity is especially useful when the molecule elongates or shortens during passage through the system. For example, the COM velocity based on measurements of intercalator signal takes into account any variations in stretching because varying regions of stretching will have proportionately higher or lower intensity of the intercalator signal.

The velocity of an elongated polymer can also be represented by the velocity of its contour center, i.e., the midpoint of its molecular contour (center-to-center velocity). The center-to-center velocity can be measured by determining the time interval the contour center of an elongated polymer requires to travel between two detection zones of known distance. Depending on whether the polymer is uniformly elongated or not, the center-to-center velocity can be the same or different from the COM velocity. In particular, if the polymer is not uniformly elongated, the center-to-center velocity is generally different from the COM velocity.

The velocity of an elongated polymer can also be represented by the velocity of its leading or trailing end, i.e., end-to-end velocity. The end-to-end velocity can be measured by determining the time interval the leading or trailing end of an elongated polymer requires to travel between two detection zones of known distance.

The velocity of an elongated polymer can also be represented by the rise-time velocity which is defined as the velocity of the leading end of the elongated polymer traverse through a region of finite size. A rise-time velocity can therefore be measured by dividing the size of the region with the time required for the leading end of the polymer to travel from the entry edge of the region to the exit edge of the region. Rise-time velocity is particularly useful when the leading end of the polymer is labeled.

Any one type of the velocities can be used either independently or in combination with one or more other types of velocity for the characterization of an elongated polymer. The measured velocity can be used in determination of the lengths and/or distances between markers on an elongated polymers.

Figure 2A:
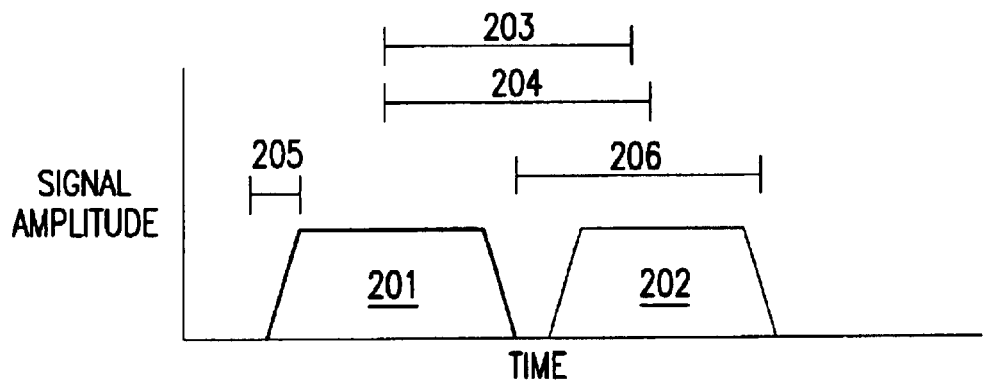
Figure 2B:
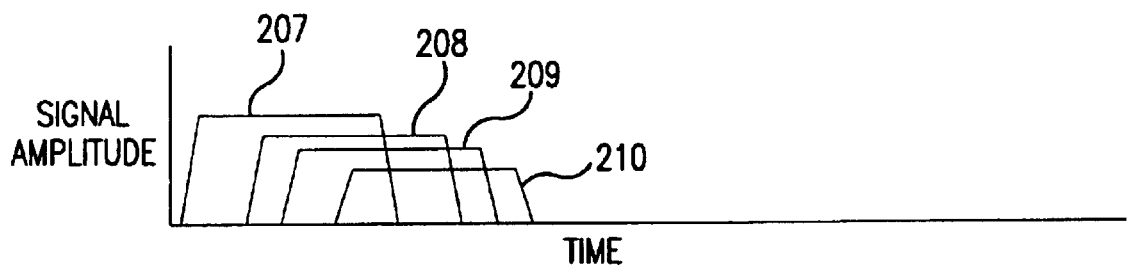
Figure 2C:
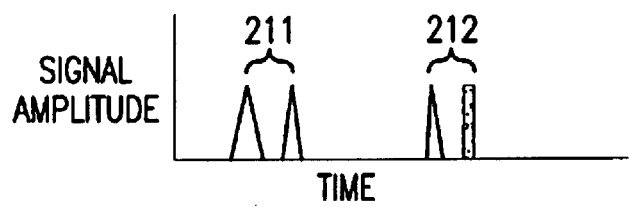

5.2. Methods and Apparatuses for Determination of Velocities of Single Elongated Polymers The methods of the invention are based on time-correlated measurements of elongated polymers as they travel past two or more detection zones with known distances among them. A schematic illustration of the methods of the invention is presented in FIG. 1. For example, detection zones 101 and 102 has a distance of D1 between them. The corresponding time-correlated signal amplitude profiles 106 and 107 are therefore separated in time by the time the polymer (105) takes to travel a distance D1. Signal amplitude profiles are then used to determine the velocity of the polymer. FIGS. 2A–2C illustrate various ways different types of velocity can be determined from measured signal amplitude profiles. The distance between each pair of detection zones is determined based on the conditions and/or requirements of the measurements. For example, when a steady flow is involved such that the velocities of polymers do not vary over a range of distances, larger distance may be used. Alternatively, when flow changes rapidly and/or the polymers vary in length rapidly, multiple closely spaced detection zones are used (FIG. 2B). In preferred embodiments, distances between the detectors is less than the length of an elongated polymer. The closer the distances between detectors, the average measured velocity will be closer to the real velocity at both detectors. Thus in some more preferred embodiments, the distances between detectors are at minimums allowed by the resolution of the method used to defined the detection zones. For example, in methods based on optical measurement, the distances between detection zones are at or close to diffraction limit.

Distances among detection zones can be determined using any methods known in the art. In one embodiment, the distances are measured by a mechanical means that offers high spatial resolution. In another embodiment, the distances can be measured by calibration using elongated polymers of a known length. In still another embodiment, the distances can be measured by calibration using a fluid flow of known velocity. Such calibration methods are well known in the art.

The methods of the invention can be based on optical methods, including but are not limited to light induced fluorescence measurements, absorption measurements, light scattering measurements and non-linear optical measurements. Such optical methods are well known in the art. It will be apparent to one skilled in the art how to choose the parameters when a particular method is selected. For example, when light induced fluorescence measurements or absorption measurements are to be used, it will be apparent to one skilled in the art how to choose, e.g., the excitation source, e.g., the wavelength, the detector, etc. When a slit is used to excite the detection zone, it is preferable to use a slit having a width that is close to the diffraction limit of the wavelength of light used such that the highest resolution can be achieved.

In some embodiments, the signal measured at the detection zone can be the light induced fluorescence of an elongated polymer. In one embodiment, the laser induced fluorescence of monomers in the polymer is measured. In another embodiment, laser induced fluorescence of intercalating dye molecules is measured. In still another embodiment, light induced fluorescence from fluorescent markers labeled at discrete locations along the polymer, e.g., at the leading or trailing ends, is measured. In other embodiments, a slit of selected width is used to define the detection zone. In this embodiment, the excitation can be selected from the emitted wavelengths of a lamp and the detection zone is illuminated through the slit.

The signal measured at the detection zone can also be the absorption of an elongated polymer. In such embodiments, the measured wavelength or wavelengths of the absorbed light are proportional to the number of monomers falling within the excitation region. In one embodiment, laser excitation is used in the absorption measurements. In this embodiment, a laser beam of a selected wavelength is used to define the detection zone. In another embodiment, a slit of select width is used to define the detection zone. In this embodiment, the excitation can be selected from the emitted wavelengths of a lamp and the detection zone is illuminated through the slit.

The signal measured at the detection zone can also be the scattered light of the polymer. In such embodiments, the polymer is labeled by molecules that scatter light. In one embodiment, laser excitation is used in the absorption measurements. In this embodiment, a laser beam of a selected wavelength is used to define the detection zone. In another embodiment, a slit of select width is used to define the detection zone. In this embodiment, the excitation can be selected from the emitted wavelengths of a lamp and the detection zone is illuminated through the slit.

Various methods can be used to define multiple detection zones in the present invention. In methods based on optical measurements, detection zones can be generated using 2 or more laser illumination spots. In some embodiments, a separate laser is used to generate each spot. Thus, multiple lasers are used to define multiple detection zones. In the embodiment, the lasers are arranged such that the collimated output of the lasers converge on the output aperture of the microscope objective. Each beam thus enters the microscope objective at a different angle. The angular displacement of the beams is converted by the objective lens to a spatial separation of the focused laser spots (FIG. 32). The spatial separation of the spots can be controlled by adjusting the angular separation of the beams. The larger the angular separation, the larger the spatial separation. In other embodiments, multiple detection zones are defined by splitting the output of a single laser to create angularly displaced beams. In one embodiment, a partially reflecting beamsplitter and a fully reflective mirror to create two beams that converge on the output aperture of the microscope objective. The angular separation is controlled by setting the spacing and angles of the partially reflecting beamsplitter from the fully reflecting mirror. In a preferred embodiment, the partially reflecting beamsplitter is a pellicle type of beamsplitter. The very thin membrane of the pellicle means that a ghost beam from the rear surface of the beamsplitter is effectively avoided. A schematic illustration of an embodiment using beamsplitter is shown in FIG. 33. In still other embodiments, a diffractive optics such as a phase grating is used to split a monochromatic laser beam into multiple beams at various grating orders, e.g., a zero order (straight through) beam, first order beams and higher order beams. The distribution of energy into the different orders is determined by the depth of the grooves in the phase grating, whereas the angular separation of different orders of beams is determined by groove spacing. Any one skill in the art will be able to choose the appropriate grating once the desired beam distribution is determined. In a preferred embodiment, additional optical element, e.g., a lens, is used to collect the diverging beams from a diffractive optics and refocus the beams so that they converge on the microscope objective. A schematic illustration of an embodiment using diffractive optics is shown in FIG. 34.

In other embodiments, a fringe pattern of alternating dark and bright bands formed within a single illumination spot is used to define detection zones (FIG. 35). An elongated polymer, such as a DNA molecule, moves through the spatially periodic bands. In one embodiment, an elongated polymer is labeled with one or more fluorescence labels. As the elongated polymer moves through the bands, any such fluorescent probe bound to it will emit fluorescence in proportion to the illuminating light. The movement of the probe will therefore result in a temporally periodic emission. The time pattern of emission is measured. Knowing the spatial periodicity, i.e, the fringe spacing, the velocity of the DNA can be calculated from the measured temporal periodicity. In an another embodiment, the backbone of an elongated DNA molecule is stain with a fluorescence dye. In this embodiment, a stairstep pattern of emission will be observed as successively more of the bright bands illuminate DNA. Any standard method known in the art can be used to generate the fringe pattern. In one embodiment, the fringe pattern is created by overlapping in a single illumination spot, two beams that have been formed from a single laser. The limiting fringe spacing is one half the wavelength of the illuminating light when the two beams are oriented 180 degrees to each other. At other angles, the fringe spacing is larger and can be found from D=λ/2sin (θ), where D is the fringe spacing, X is the wavelength of the illuminating laser and θ is the half-angle between the two laser beams. In preferred embodiments, the illumination spot is a few microns in size such that a sufficient number of fringes are formed. A schematic illustration of the optical arrangement is shown in FIG. 35.

It will be apparent to one skilled in the art that any of the optical methods can also be combined. In one embodiment, elongated DNA molecules labeled with both intercalating dye and sequence specific fluorescence markers are envisioned. Preferably, the intercalating dye and the fluorescence markers emit light of different and distinguishable wavelengths. In such an embodiment, signal amplitude profiles illustrated by both FIG. 2A and FIG. 2C are simultaneously determined for a DNA. Any dual color set ups for measuring fluorescence from both intercalating dye and fluorescence markers of a different wavelength from an elongated DNA molecule labeled with both intercalating dye and sequence specific fluorescence markers known in the art can be used, e.g., Deniz et al., 1999, *Proc. Natl. Acad. Sci. USA.* 96:3670–3675; and Ha et al., 1996, *Proc. Natl. Acad. Sci. USA.* 93:6264–6268.

Any methods known in the art for elongating single polymers, e.g., single DNA molecules, can be used in the invention. In some embodiments of the invention, single polymers are elongated by an elongation structure described in Section 5.5., infra. Single elongated polymers are then delivered to the detection region of the apparatus by any means described in Section 5.5. Preferably, the detection region is located along the path of the elongated molecule where measurements of molecular properties can be performed. In preferred embodiments, the detection region is located where the depths of the fluid flow path, i.e., the dimension of a detection zone that is perpendicular to the fluid flow direction, is within the depth of optical field of view such that the elongated molecules can be measured accurately in the entire depth of fluid flow. More preferably, in the detection region polymers maintain elongated conformations. In one embodiment, the detection region is located at the tapered channel portion of an elongation structure (see, Section 5.5., infra). When the detection region is located at the tapered channel portion of an elongation structure, it is preferred that the detection is performed in the direction of constant channel width.

5.2.1. Center-of-Mass Velocities of Polymers

Various methods can be used to determine the COM velocity of an elongated polymer. Any detection methods that allow measuring the mass of the section of an elongated polymer falling within a detection zone can be used. Such detection methods can be, but are not limited to, optical detection methods and electrical detection methods.

In a preferred embodiment, the COM velocity is determined from measured intensity-time curves of DNA molecules stained with intercalating dye molecules. It is well known in the art that the amount of intercalating dye molecules bound to a DNA molecule is proportional to the length of the DNA molecule. For example, intercalating dye YOYO-1 binds to DNA molecules at a dye:base pairs ratio of 1:5 (see, e.g., Larsson et al., 1994, *J. Amer. Chem. Soc.* 116:8459–8465). The fluorescence intensity of intercalating dye is therefore proportional to the length or mass of the DNA molecule. Thus, the center-of-mass of a DNA can be determined from the measured fluorescence intensity-time curve by integrating the fluorescence intensity as a function of time according to the equation:

$$L_{com} = \frac{\int_{t_1}^{t_2} I(t) \cdot L(t) \, dt}{\int_{t_1}^{t_2} I(t) \, dt} \quad (1)$$

where $L_{com}$ is the location of the center-of-mass along the polymer, I(t) is the fluorescence intensity measured at time t, $t_1$, and $t_2$ designate the time when the polymer enters and leaves the detection zone, respectively, and L(t) is the length of the polymer that has passed through the detection zone at time t. It will be obvious to one skilled in the art that any time before $t_1$ can be used as the lower bound of the integral and any time after the time $t_2$ can be used as the upper bound of the integral. L(t) can be determined according to equation (2)

$$L(t) = \int_{t_1}^{t} v(\tau) \, d\tau \quad (2)$$

where v(t) is the velocity of the polymer at time t. Thus the temporal location of the center-of-mass $t_{com}$ of an elongated polymer can be determined by solving the equation $$\int_{t_1}^{t_{com}} v(t) \, dt = \frac{\int_{t_1}^{t_2} I(t) \cdot \left[ \int_{t_1}^{t} v(\tau) \, d\tau \right] dt}{\int_{t_1}^{t_2} I(t) \, dt} \quad (3)$$

In cases where the velocity of the polymer is constant, i.e., v(t)=V, the temporal location of the center-of-mass can be determined by the equation $$T_{com} = \frac{\int_{t_1}^{t_2} I(t) \cdot t \, dt}{\int_{t_1}^{t_2} I(t) \, dt} \quad (4)$$

The COM velocity is then determined by dividing the distance between two detection zones of known distance with the difference in $T_{com}$ at the two detection zones.

In another embodiment, the COM velocity is determined from the measured intensity-time curve of intrinsic stimulated fluorescence from an elongated polymer. When monomer units of a polymer can be excited by light and fluoresce at a detectable wavelength, intensity-time curves can be measured by monitoring fluorescence at the emitted wavelength. When this approach is to be used, it is preferable that the fluorescent monomers are evenly distributed along the polymer. The fluorescence intensity then provides a measure of the length or mass of the polymer.

5.2.2. Center-to-Center Velocities of Polymers

Depending on the channel geometry used for delivering the polymers, e.g., DNA molecules, a center-to-center approximation of the velocity of polymer movement can be used. For example, a center-to-center velocity of an elongated DNA can be used where a constant flow profile is generated. The center-to-center velocity is generally different from the center-of-mass velocity. The center-to-center velocity is determined by measuring the time interval for the mid point of the molecular contour of an elongated polymer, i.e., the center of the polymer contour, to travel between two detection zones separated by a known distance. The center of an elongated polymer is defined as $$L(t_c) = \frac{L(t_1) + L(t_2)}{2} \quad (5)$$

where $L(t_c)$, $L(t_1)$ and $L(t_2)$ are defined by Eq. (2). In cases where the velocity of the polymer is constant, i.e., $v(t)=V$, the temporal location of the center of the polymer can be determined by the equation $$t_c = \frac{t_1 + t_2}{2} \quad (6)$$

where $t_c$ is the temporal location of the center of the measured signal amplitude profile, e.g., intensity-time curve, of the polymer, $t_1$ and $t_2$ are the leading and trailing edges of the signal amplitude profile, respectively. The center-to-center velocity is then determined by dividing the distance between two detection zones with the difference in $T_c$ at the two detection zones.

In some cases, e.g., when a polymer is elongated such that its mass is uniformly distributed across its length, the center-to-center velocity is the same as the center-of-mass velocity.

5.2.3. End-To-End Velocities of Polymers

The end-to-end velocity is determined using the entrance or exit of the elongated molecule through two detection zones. In some embodiments, a front-end to front-end velocity is determined by measuring the front end of the polymer passing through the two detection zones. In other embodiments, a trailing-end to trailing-end velocity is determined by measuring the front end of the polymer passing through the two detection zones. End-to-end velocity can be measured by any methods that are capable of detecting the ends of a polymer.

In some embodiments of the invention, the end-to-end velocity of an elongated polymer is determined from signal amplitude profiles measured at two detection zones by a method that allows measuring the mass of polymer section in the respective detection zone. In a preferred embodiment, the polymer is labeled along the length, e.g., DNA molecule is labeled with intercalating dye. The entrance of the DNA molecule into a detection zone is marked by a rise in the intercalator signal. The exit of the DNA molecule from the detection zone is marked by the decrease in the intercalator signal. Using the known distance of separation in the detection zones, the velocity can be determined using any combination of edges of the intensity-time curves and their respective times of entry/exit into their respective detection zones. In one embodiment, a time of entry or exit of the polymer in the detection zone is identified as the temporal location where intensity-time curve begins to deviate from the background level. In another embodiment, a time of entry or exit of the polymer is identified as the time at the half height of the leading or trailing edge of the intensity-time curve. The end-to-end velocity is then determined by dividing the distance between two detection zones with the difference in the entry or exit times at the two detection zones. This is more accurate than end labeled polymer and more easily measured due to many dye molecules.

In some other embodiments, the polymer is labeled at one or both ends and the label is detected to determine the end-to-end velocity. In one embodiment, the polymer is labeled at one end with a fluorescent dye molecule. The fluorescence signals are detected at two detection zones of a known distance. The end-to-end velocity is determined by dividing the distance between the two detection zones by the measured time interval of the signals. Because the polymer can enter the detection zones with labeled end or the unlabeled end as the leading end, it is important that the polymer travel from the first detection zone to the second detection zone without switching leading and trailing ends. This condition is normally satisfied if no obstacles are located between the two detection zones.

In a preferred embodiment, the polymer is labeled at both ends with the same dye. Two fluorescence signals are detected at each detection zone. The end-to-end velocity can be determined by the two first signals or the two second signals. Labeling of the polymer at both ends is more preferred than labeling of the polymers at one end, since the detection of two correlated signals corresponding to the labels at the leading and the trailing ends at each detection zone can be used to confirm the detection of the labeled ends of a polymer. This is especially important when loose dye molecules or other fluorescent specifies may be present in the sample. In another preferred embodiment, the two ends of a polymer can be labeled with dyes of different emission spectrum.

5.2.4. Velocities of Polymers from Rise-Time Measurements

The rise-time approximation allows the determination of the velocity of an elongated polymer by measuring the time required for the leading end of the polymer to traverse the detection zone and the size of the known size of the detection zone. Alternatively, the velocity of an elongated polymer can be determined by measuring the time required for the trailing end of the polymer to traverse the detection zone and the size of the known size of the detection zone. In contrast to COM, center-to-center and end-to-end velocities, the rise-time velocity is determined using only one detection zone.

In some embodiments of the invention, the rise-time velocity of an elongated polymer is determined from signal amplitude profiles measured at a detection zone by a method that allows measuring the mass of polymer section in the detection zone. In a preferred embodiment, the polymer is labeled along its length, e.g., DNA molecule is labeled with intercalating dye. The entrance of the DNA molecule into a detection zone is marked by a rise in the intercalator signal. The exit of the DNA molecule from the detection zone is marked by a decrease in the intercalator signal. The intercalator signal from the DNA reaches full intensity as the front end of the DNA molecule reaches the far-edge of the detection zone. Thus, in an intensity-time curve, rise-time is represented by the rising edge of the intensity-time curve. The rise-time velocity is then determined by dividing the detection zone dimension by the time interval between the entrance of the front end of the DNA molecule to reach this full intensity. In one embodiment, the detection zone is defined by the spot size of a laser excitation beam from a 532 nm diode pumped solid-state laser focused to a beam waist of about 266 nm. In such embodiment, the resolution of rise-time velocity is 266 nm divided by the rise-time.

5.2.5. Determination of Velocities of Polymers Labeled with Markers at Known Distances on a Polymer The velocity of elongated polymers can also be determined by monitoring the time interval between markers on the polymers at known distances. In such embodiments, because the distance between two or more markers on a polymer is known, the velocity of the polymer can be determined using a single detection zone.

In a preferred embodiment, sequence specific markers, e.g, a fluorescently labeled oligonucleotides of defined sequences that hybridize to and therefore "mark" the complementary sequences present in a target DNA molecule, that are specific to known sequences on a DNA molecule, are used to labeled the DNA molecule. The distance between each adjacent pair of markers is preferably greater than half the dimension of the detection zone so that signals from adjacent markers can be distinguished. The velocity of the polymer is then determined by dividing the known distance between a pair of markers with the time interval between the signals from the two markers. Any sequence specific markers can be used in the present invention, including, but are not limited to, fluorescently labeled sequence specific major or minor groove binders and intercalators, sequence-specific DNA or peptide binding proteins, sequence specific peptide nucleic acids (PNAs), etc.

5.2.6. Characterization of Velocities of Single Elongated Polymers by Combination of Methods It will be apparent to one skilled in the art that two or more methods can be combined to give more information about the motion of elongated polymers. In one embodiment, COM velocity and end-to-end velocities, e.g., front-end-to-front-end and/or trailing-end-to-trailing-end velocities are determined for an elongated polymer. COM velocity and end-to-end velocity are then compared. A difference between COM velocity and end-to-end velocity indicates that the length of the polymer may be changing. In another embodiment, rise-time velocity is determined to estimate the size of the detection zone. The rise-time velocity is subtracted from a simultaneously determined COM velocity, center-to-center velocity and/or end-to-end velocity such that the contribution of finite size of the detection zone is eliminated.

5.3. Methods of Determination of Lengths of Single Polymers

The invention also provides methods for determination of the lengths of single elongated polymers and for determination of the distances between tags along single elongated polymers. Methods for measurements of lengths of single polymers and distances between tags on single polymers are useful in, e.g., DNA restriction fragment sizing. The length of or the distance between two markers on a traveling single elongated polymer, e.g., a single elongated DNA, can be determined using discrete detection zones if the velocity of the polymer is known. For example, if the velocity of a polymer is v(t), then the length of the polymer can be determined from the signal amplitude profile measured at a detection zone according to the equation:

$$L = \int_{t_1}^{t_2} v(t)\, dt \quad (7)$$

where L is the length of the polymer, $t_1$ and $t_2$ are the leading and trailing edges of the signal amplitude profile.

In some embodiments of the invention, the velocity of the polymer is approximated by a time independent velocity V. In such embodiments, the length of the polymer can be determined as $L = V \cdot (t_1 - t_2)$.

However, since the velocity of the polymer may be changing, e.g., accelerating or decelerating upon passage through the region of interest. It may be desirable to create multiple detection zones along the path of the elongated polymer so that multiple signal amplitude profiles can be obtained. In one embodiment, the spacings between each adjacent pair of detection zones are much smaller than the length of the elongated polymer. In such an embodiment, overlapping signal amplitude profiles along the strand of the elongated polymer can be obtained, permitting determination of time dependent velocity v(t). This will increase the accuracy of the velocity measurements thus provide a more accurate measurement of the polymer length. A schematic of the output is shown in the following FIG. 2B. In FIG. 2B, four signal amplitude profiles of an elongated polymer is shown (with arbitrary relative intensities). Any of the different types of velocities can be used in the multiple detection scheme. For instance, velocity determination can further be estimated by using a combination of leading end velocity information, center-of-mass estimations, rise time estimations, and other information that can be obtained from the intercalator signal.

5.4. Methods of Analyzing Polymers

The methods and apparatuses of the invention can be used in analysis of polymers. For example, the methods and apparatuses of the invention can be used in analysis of single DNA molecules, such as single-molecule restriction fragment length polymorphism (RFLP).

5.4.1. Single-Molecule Restriction Mapping

The invention provides a method for single-molecule restriction mapping. In one embodiment, a suitable restriction enzyme or enzymes are used to produce restriction fragments. Any restriction enzymes can be used in conjunction with the invention. The recognition sequences and reaction conditions of many restriction enzymes are well known to one skilled in the art. Depending on the sequences of the DNA molecules that are to be analyzed, suitable restriction enzymes can be selected by any one skilled in the art and obtained from various vendors, e.g., New England Biolab. A sample containing fragments from restriction digestion is then labeled, e.g., stained with an intercalating dye, such as but is not limited to YOYO-1. The labeled fragments are then elongated and detected by a method of the invention. In one embodiment, a sample containing stained restriction fragments is sent through an elongation structure comprising a combination of an obstacle field upstream of a tapered channel. The obstacle field serves both to uncoil the DNA fragments from their random coil configurations and to separate DNA fragments such that single DNA fragments enter the tapered channel separately (see Section 5.5., infra). Two or more detection zones are located in the tapered channel region where the lengths of single restriction fragments are measured. The tapered channel serves to maintain the restriction fragments in their elongated conformation so that their lengths can be accurately determined. It will be apparent to one skilled in the art that other methods may also be used to separate and elongate restriction fragments. For example, a gel filled channel can be used before the tapered channel.

In another embodiment, modified restriction enzymes that recognize and bind to their recognition sequences but do not cleave the substrate DNA molecule are used to labeled a DNA molecule. In another embodiment, a restriction enzyme is used in conjunction with a buffer, e.g., in a solution of low concentration of Mg2++, such that the restriction enzyme recognize and bind to their recognition sequences but do not cleave the substrate DNA molecule. The restriction enzymes are fluorescently labeled. Single labeled DNA molecules are then elongated by an elongation structure of the present invention and distances between labels along the DNA molecules are measured. In one embodiment, a sample containing the labeled DNA molecules is sent through an elongation structure comprising a combination of an obstacle field upstream of a tapered channel. The obstacle field serves both to elongate the DNA molecule from their random coil configurations and to separate DNA molecules such that single DNA molecules enter the tapered channel separately (see Section 5.5., infra). Two or more detection zones are located in the tapered channel region where distances between labeled restriction sites on a DNA molecule are measured. The tapered channel serves to maintain the restriction fragments in their elongated conformation so that distances between labeled restriction sites can be accurately determined. It will be apparent to one skilled in the art that other methods may also be used to separate and elongate restriction fragments. For example, a gel filled channel can be used before the tapered channel. It will be apparent to one skilled in art that other sequence specific labels can be used in place of or in conjunction with labeled non-cleaving restriction enzymes. Such sequence specific labels include but are not limited to sequence specific major or minor groove binders and intercalators or sequence specific PNAs, etc.

It will be apparent to one skilled in the art that a combination of cleaving and non-cleaving restriction enzymes can also be used. In one embodiment, restriction enzymes that cleave a substrate are used to generate restriction fragments. Restriction fragments are stained with an appropriate intercalating dye. Non-cleaving restriction enzymes labeled with a fluorescence dye of a wavelength different and distinguishable from that of the intercalating dye are used to labeled internal restriction sites in these restriction fragments. Simultaneous detection of both wavelengths allows determination of lengths of restriction fragments and identification of internal sequences. It will be apparent to one skilled in art that other sequence specific labels can be used in place of or in conjunction with labeled non-cleaving restriction enzymes. Such sequence specific labels include but are not limited to sequence specific major or minor groove binders and intercalators or sequence specific PNAs, etc.

5.5. Methods and Apparatuses for Elongation of Polymers

In the present invention, elongated single polymers can preferably be obtained and maintained by methods and apparatuses described in this section. The methods and apparatuses make use of the macrofabricated structures to elongate or stretch polymers and maintain such polymers in elongated conformations. However, the invention does not limited to these methods and apparatuses, and any other methods known in the art for elongating single polymers can also be used in conjunction with the methods and apparatuses for determining velocity and/or lengths of the invention.

For example, when a polymer molecule in a fluid flow encounters an obstacle of appropriate dimension, it may "hook" around the obstacle such that portions of the polymer chain on each side of the obstacle become elongated. The polymer may then travel down the side that has a greater portion of the molecular mass. (See, e.g., Austin et al., 1993, Analysis 21:235–238.) In addition, if there are a plurality of obstacles properly arranged and spaced, e.g., in rows perpendicular to the flow direction, localized velocity gradients are created around and between the obstacles, since the cross-sectional area available for fluid flow is reduced. As a result, the fluid flowing in between the obstacles moves faster than the fluid before and after. This creates an elongational force that serves as an additional means to elongate the polymer. When the combined effects is properly multiplied by having an entire field of properly-sized obstacles, the polymer elongates or stretches out.

Once the polymer has passed the array of obstacles and enters a free solution in its fully extended form it will rapidly return to a coiled conformation. To prevent this from happening, tapered channels are designed to provide an elongational force on the polymer, causing it to remain in a stretched or elongated conformation.

As an example of such an elongation mechanism, and not intended to be limiting, the elongational force on a polymer in a tapered channel can be resulted from a elongational flow component of a fluid flow with a strain rate of S:

$$\partial u/\partial x = S \quad (8)$$

where x is the distance along the flow direction in the channel, and u is the fluid flow velocity in the x direction, which can be determined from the flow rate (Q) and the cross-sectional area, A, of the channel as follows:

$$u = Q/A \quad (9)$$

In one embodiment where the channel cross-section is rectangular, the channel may be defined at each x along the channel by a constant height, H, and a x-dependent width, W, such that the cross-sectional area A=HW. The fluid flow velocity is given by:

$$u = Q/HW \quad (10)$$

For an incompressible flow, Q is constant. Hence, u is inversely proportional to W. This relationship can be substituted into the expression for S to determine a relationship between the strain rate and the channel width:

$$S = \partial u/\partial x = Q/H \partial/\partial x (1/w) = (-Q/HW^2)(dW/dx) \quad (11)$$

$$dW/dx = (-SH/Q)(W^2) \quad (12)$$

Integrating this expression, it is found that:

$$W = (SHx/Q + C)^{-1} \quad (13)$$

where C is a constant of integration determined by the width at the starting end, i.e., the wider end, of the channel (boundary condition). In preferred embodiments of the invention, x is a distance measured from the starting end of the channel. In such embodiments, C is given by $1/W_0$, where $W_0$ is the starting width of the channel. This equation can be used to determine the channel width when S, Q and H are set. Similar calculations may readily be completed by those of skill in the art for non-rectangular channel shapes. It is well known in the art that a strain rate above a threshold can result in elongation or stretching of a polymer. The multiple of the strain rate and the relaxation time is known as the Deborah number, De=τ·S, and can be used to determine whether the stretching will be maintained (see, e.g., Smith et al., 1998, Science 281:1335–1340). If De is much greater than one, then the strain force predominates and the polymer will remain stretched. If De is much smaller than one, then the natural relaxation process dominates and the polymer will not maintain a stretched or elongated conformation. Thus a tapered channel with a desired stain rate can be designed to support an elongational flow component which can serve to elongate a polymer. When no net momentum transfer occurs in the height axis, i.e., when the velocity profile in the z-axis has been established, the shear rate from the width profile results in a stretching force:

$$F=\mu HLS \tag{14}$$

where L is the length of the channel wall, approximately the length of the channel in which the constant strain rate is maintained.

5.5.1. Structures for Stretching Polymers

The structures for stretching DNA of the present invention ("elongation structures") comprise two regions: a delivery region and a region of polymer elongation. The delivery region is a channel, i.e., a wide channel, that leads into and out of the region of polymer elongation. The region of elongation comprises at least one of four main components: (1) funnels; (2) structures having branched channels; (3) channels with bends or curves; and (4) obstacles defining small gaps, wherein the obstacles can be, inter alia, posts or steps. The invention encompasses combinations of the four main components and variations of the main components themselves. In some embodiments, a combination of two or more of the main components can give rise to additional designs that work well to extend and stretch polymers, particularly DNA, in a controllable fashion. In addition, several of the same design may be repeated in parallel or in series.

Figure 3A:
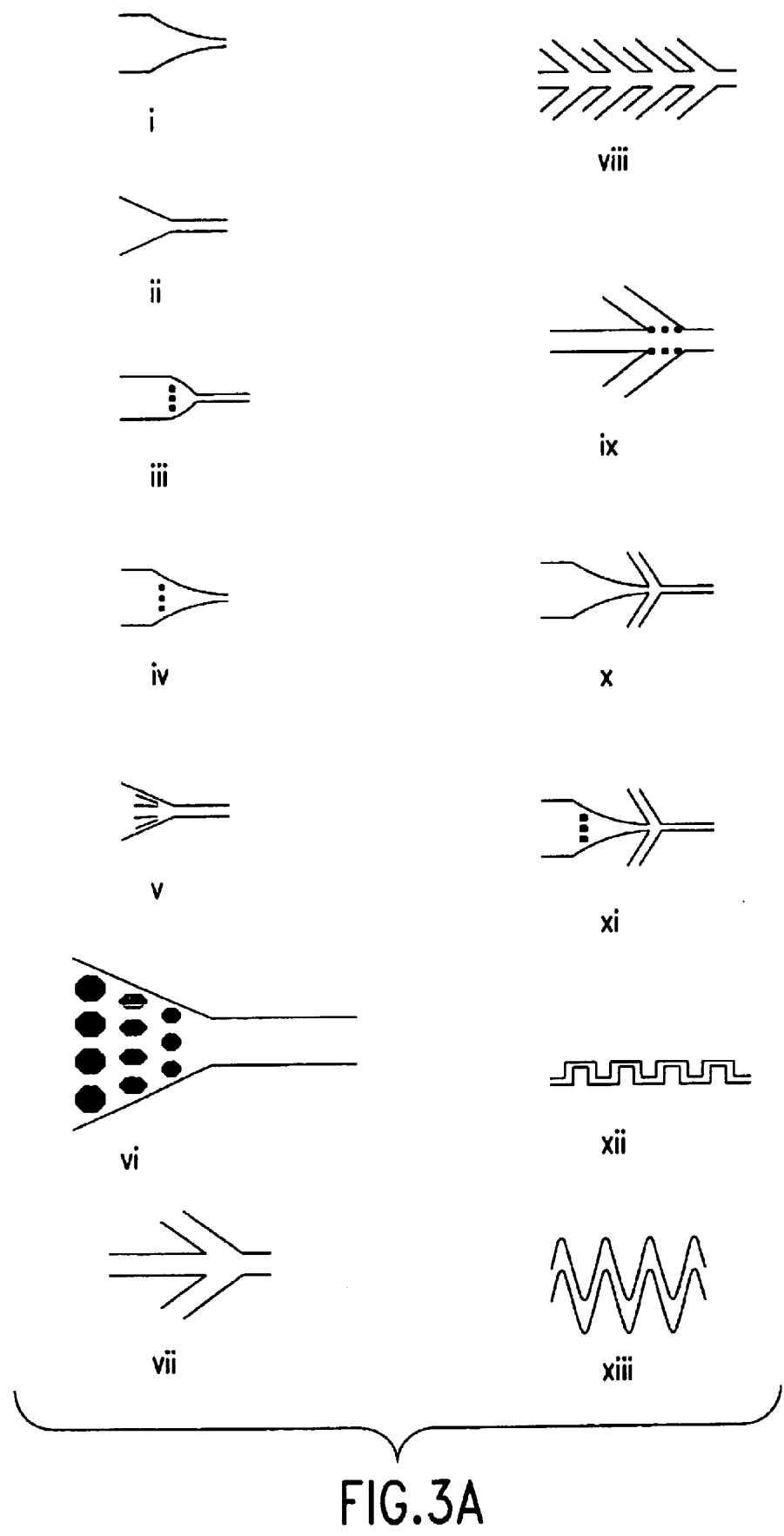
Figure 4A:
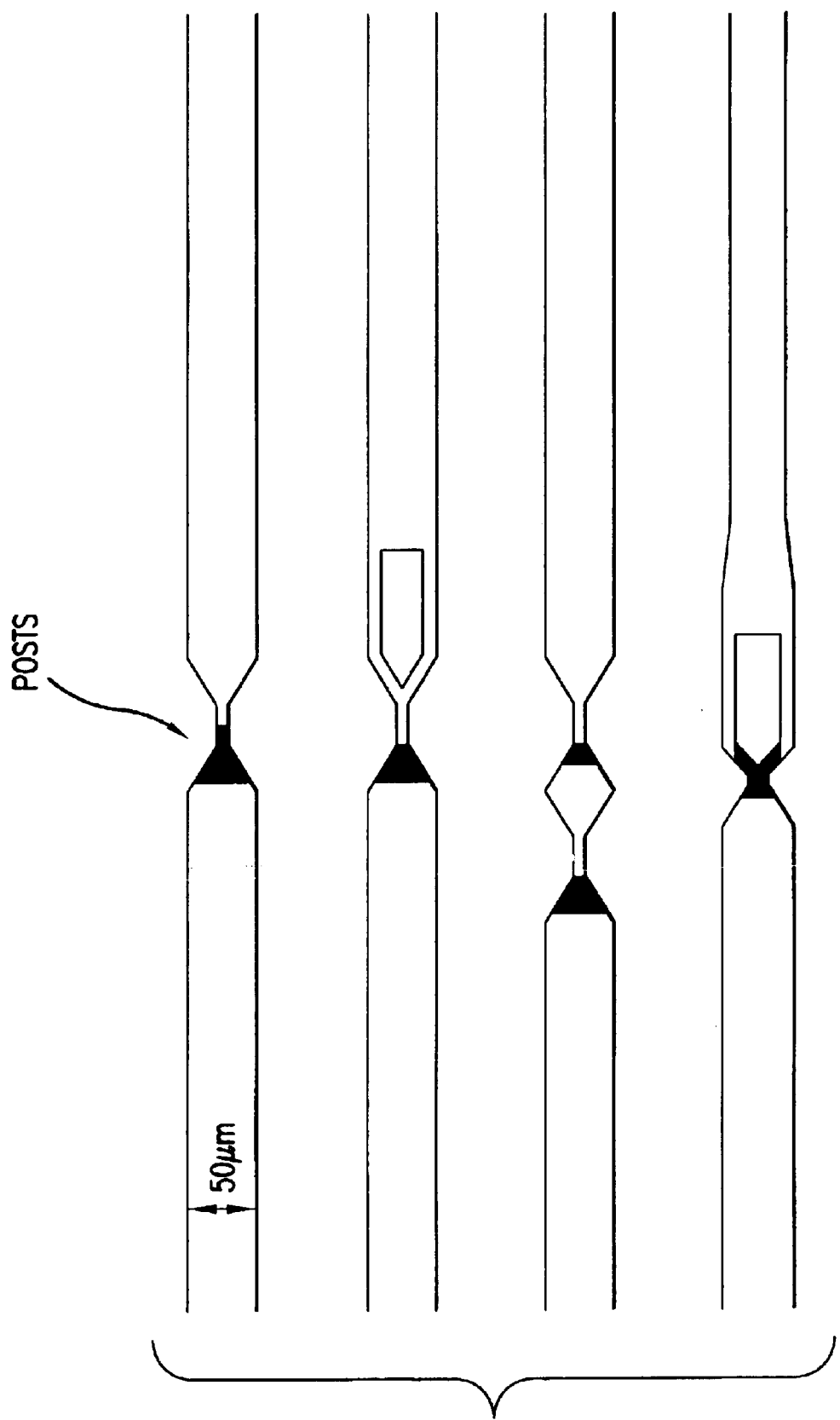
Figure 4B:
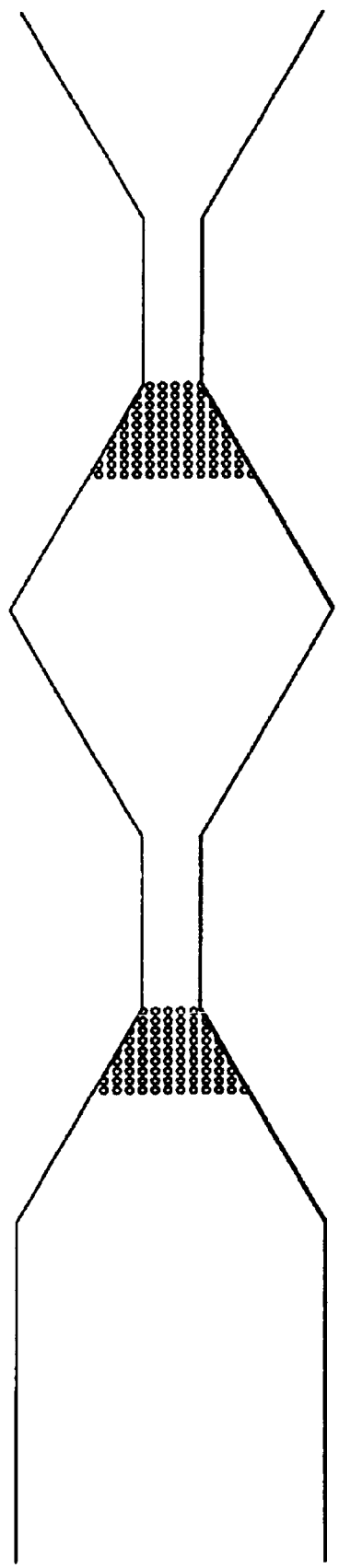
Figure 4C:
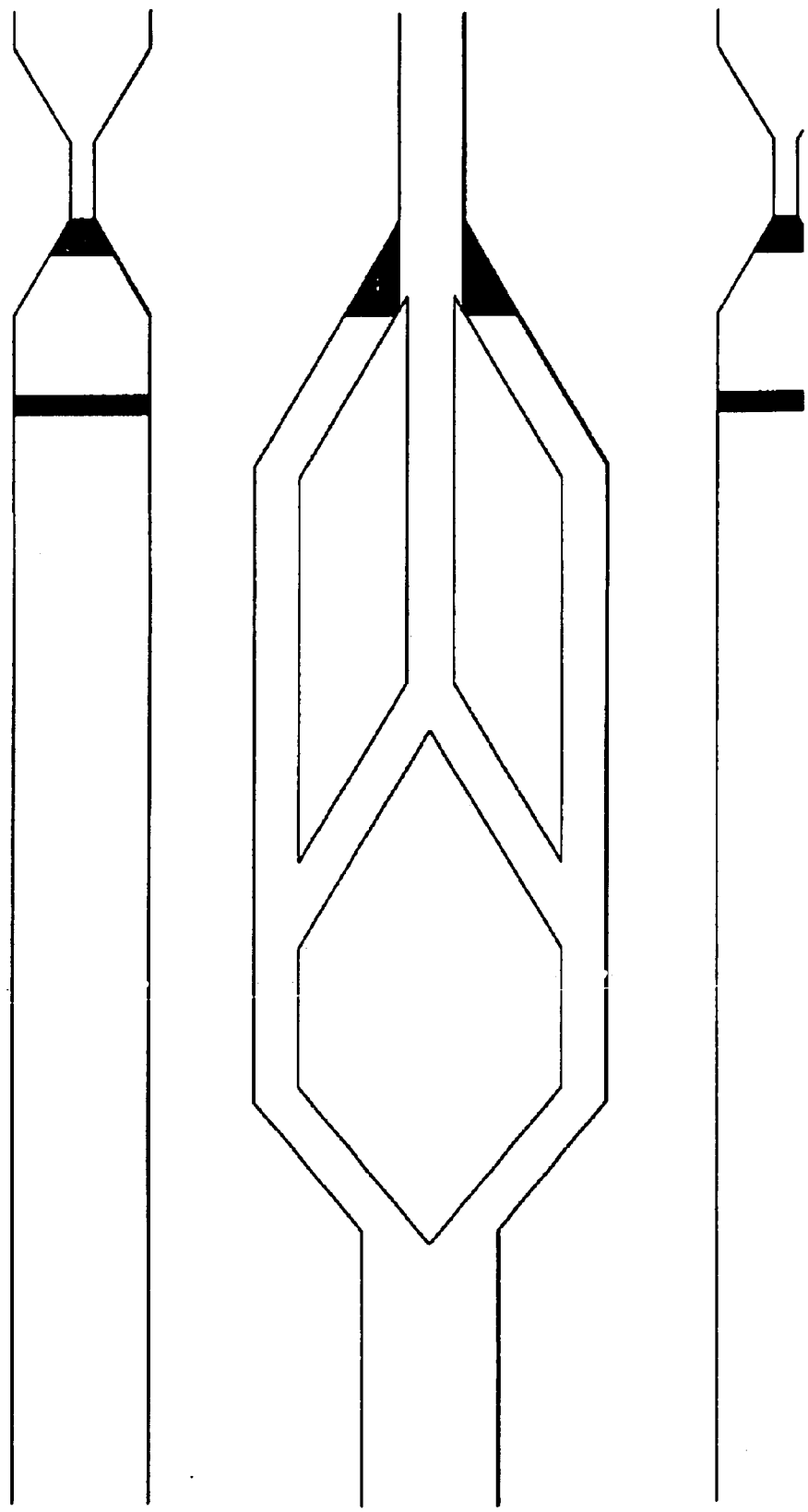
Figure 4D:
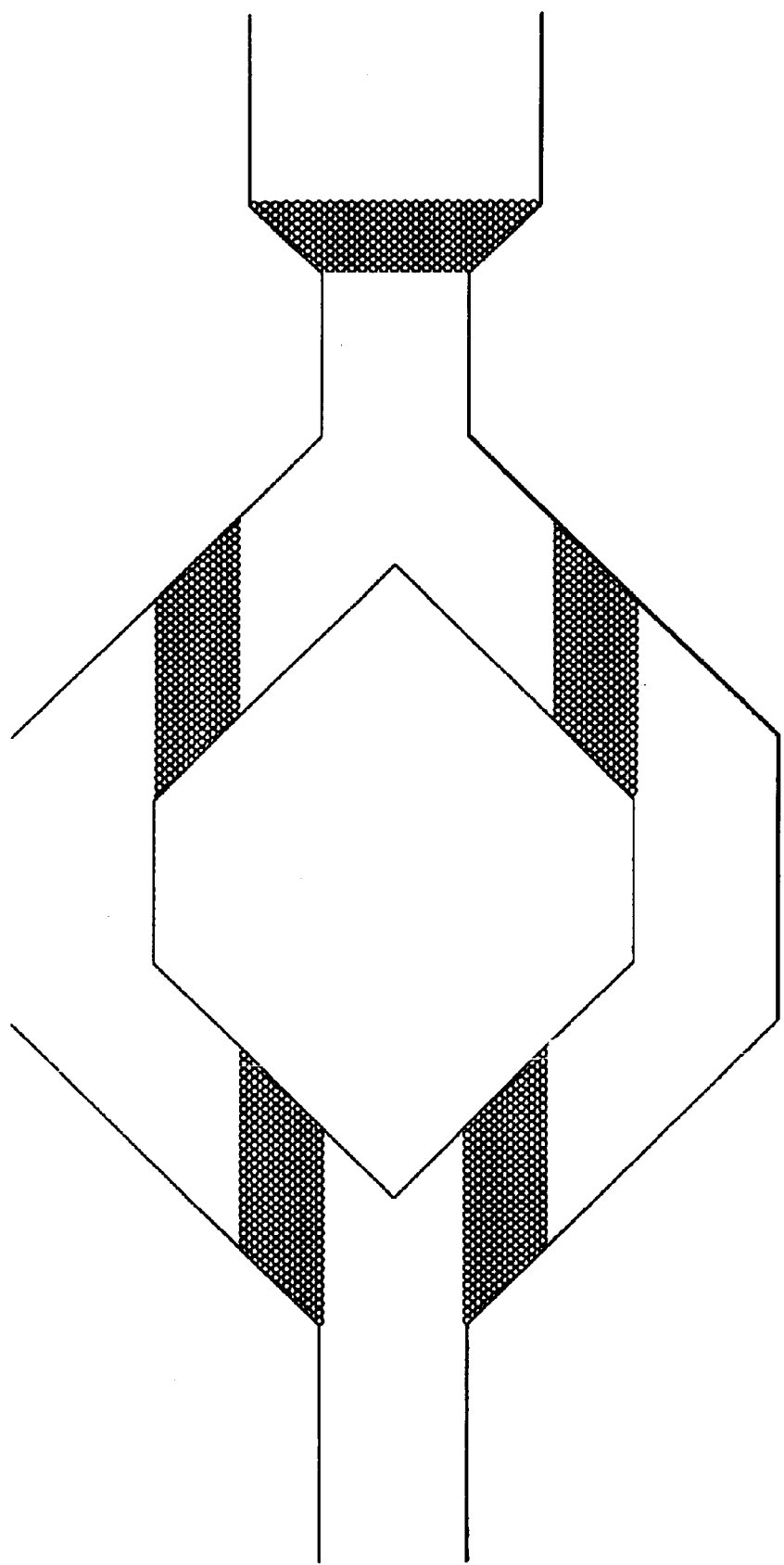
Figure 4E:
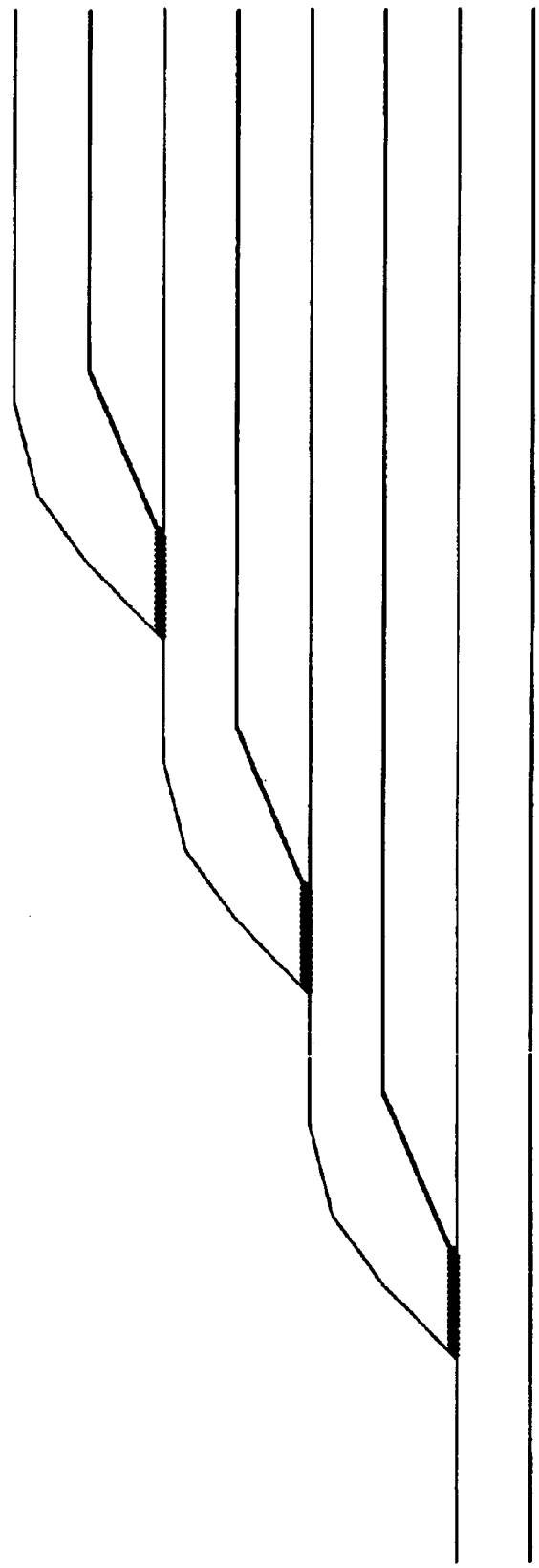
Figure 4F:
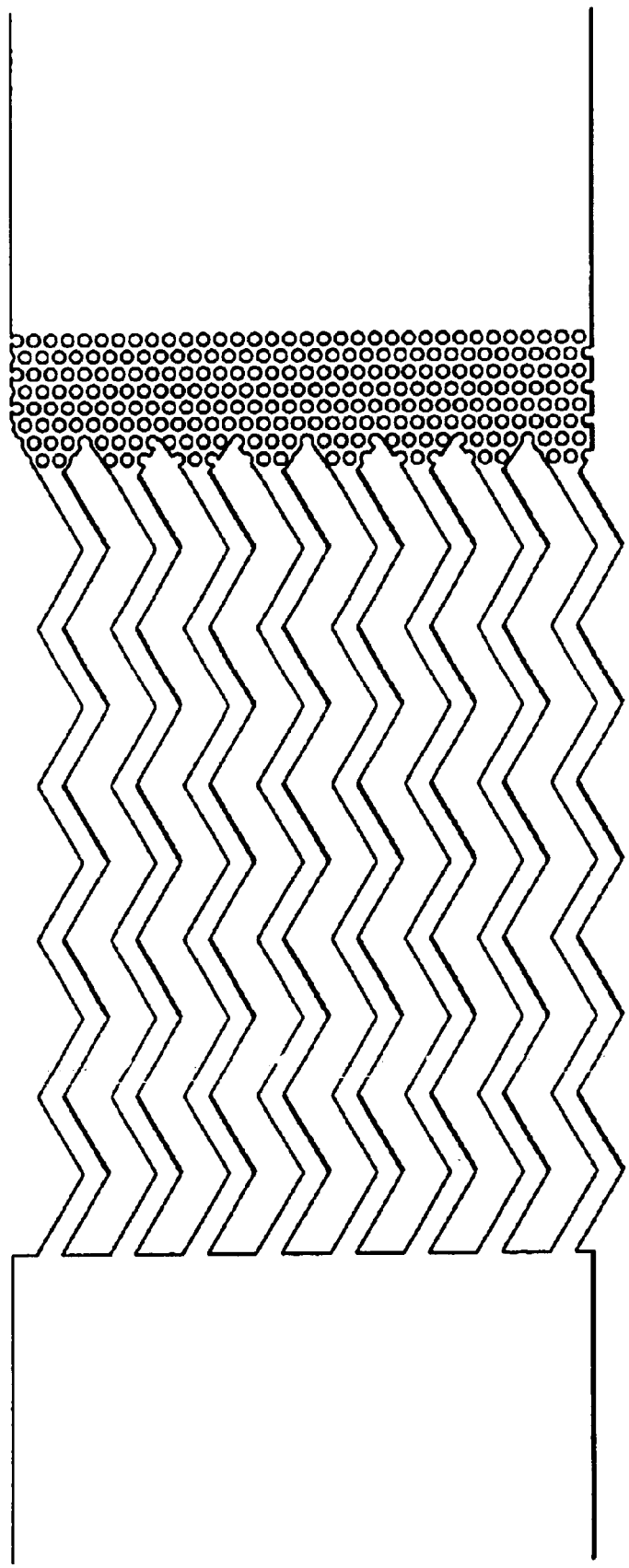
Figure 4G:
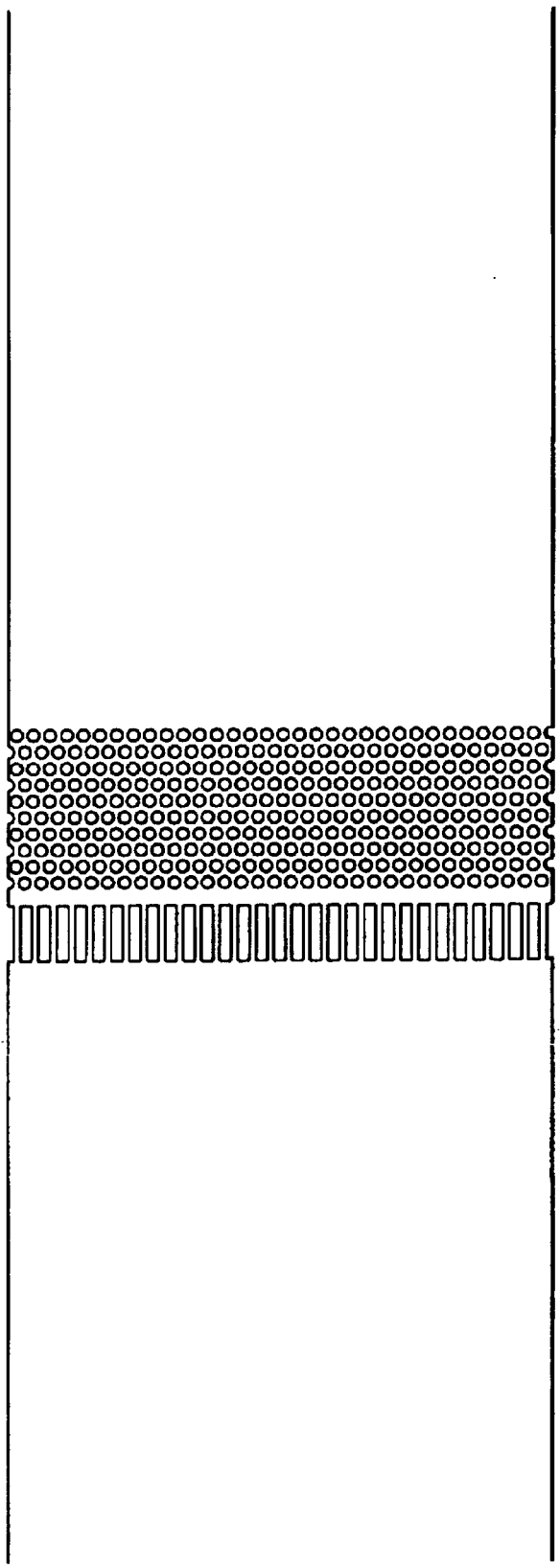
Figure 4H:
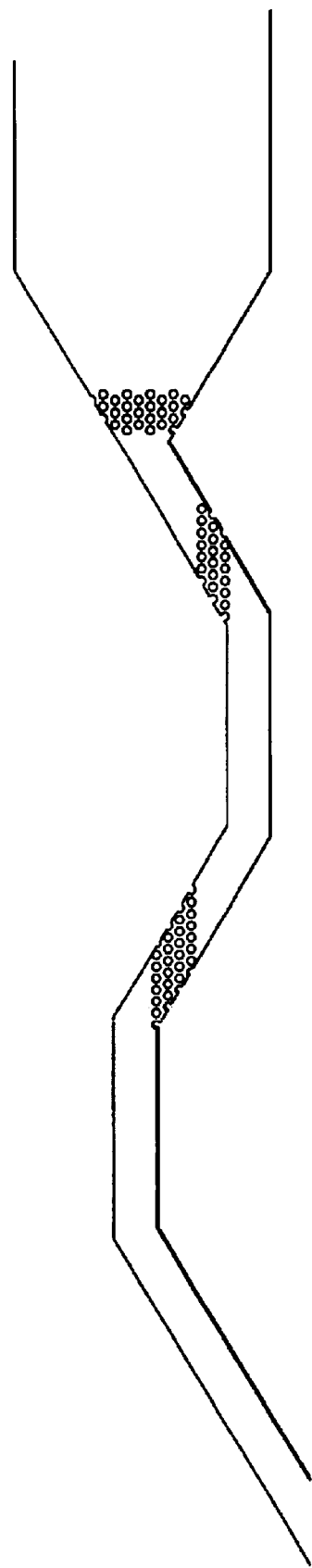
Figure 41:
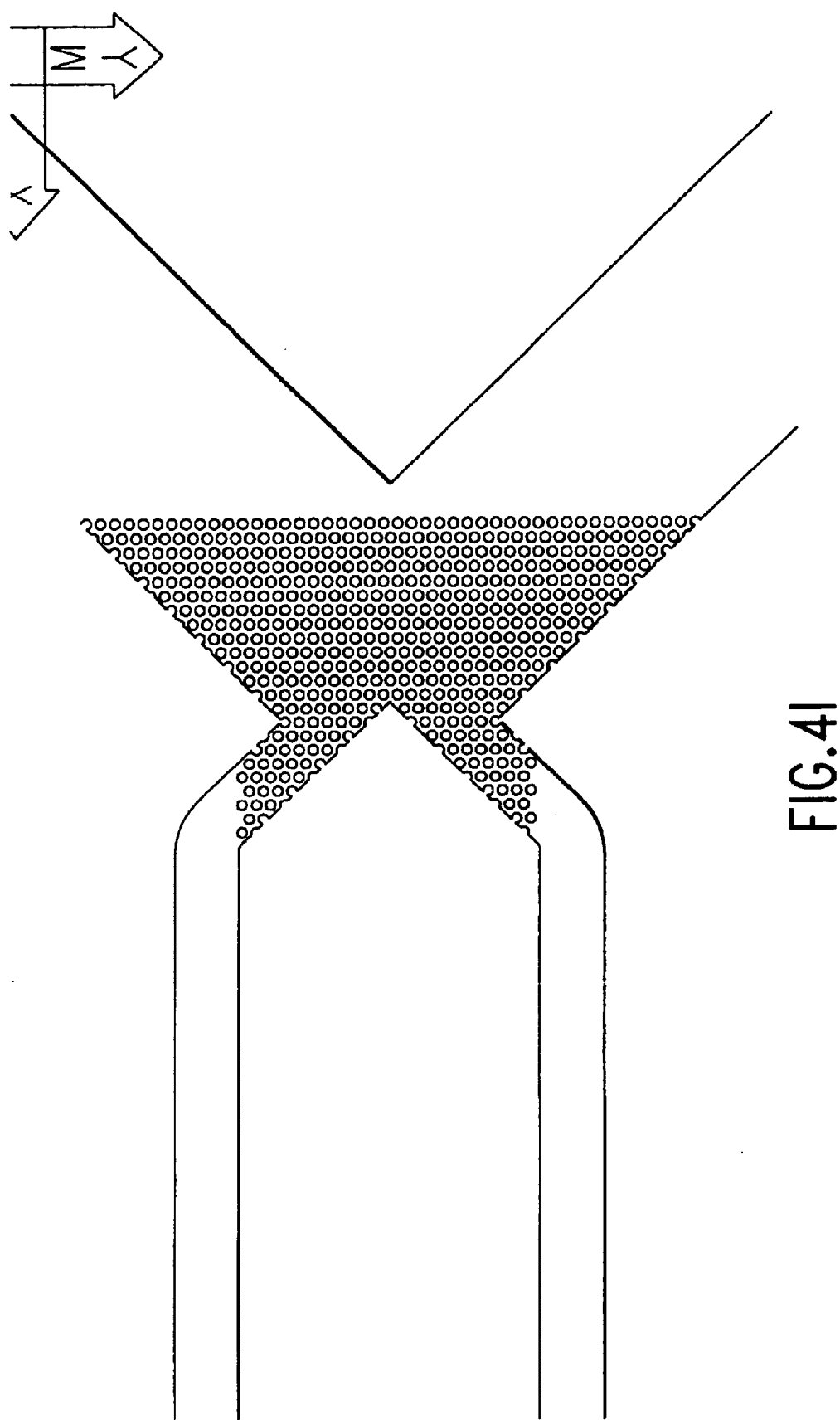
Figure 4J:
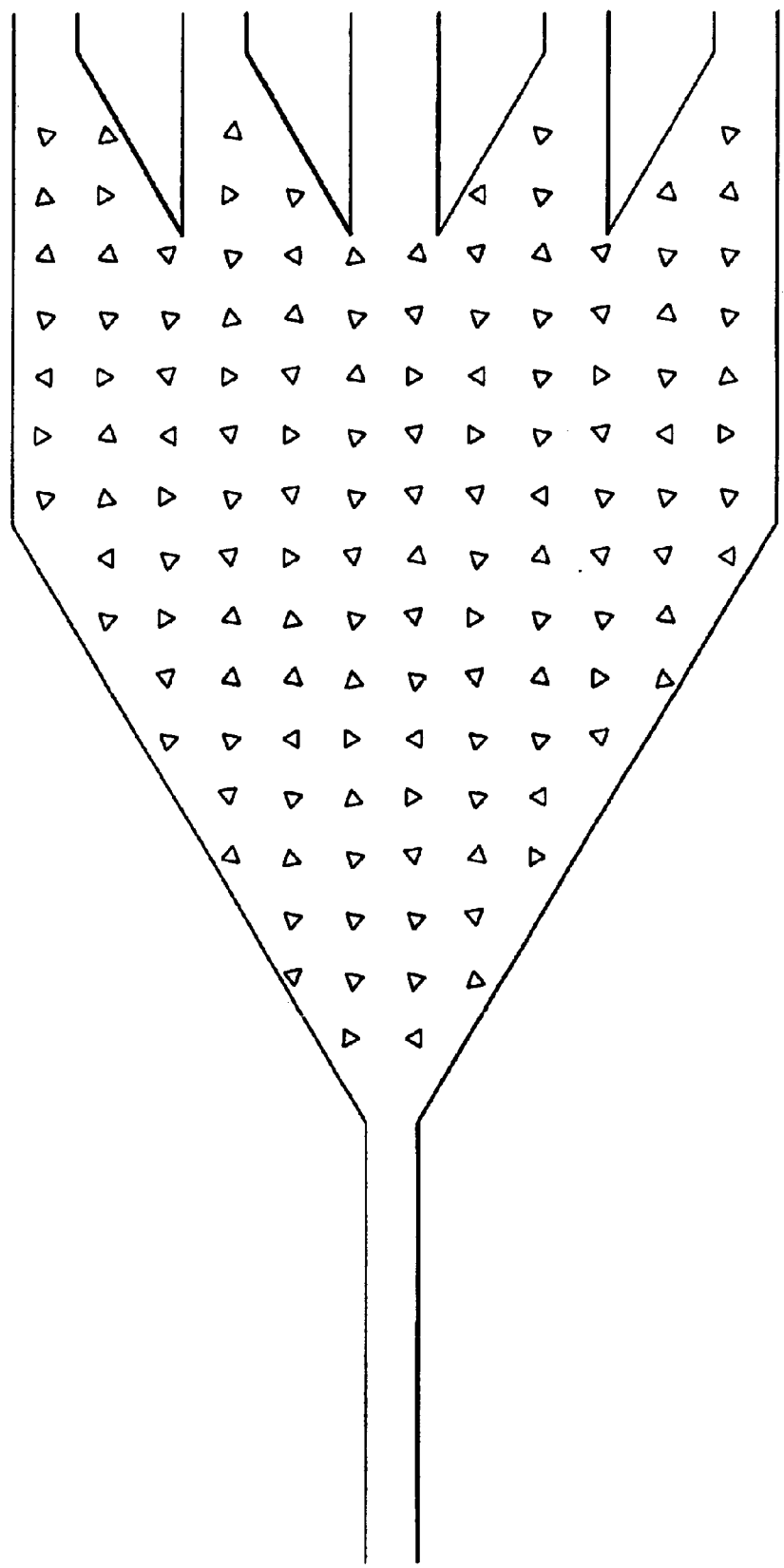
Figure 4K:
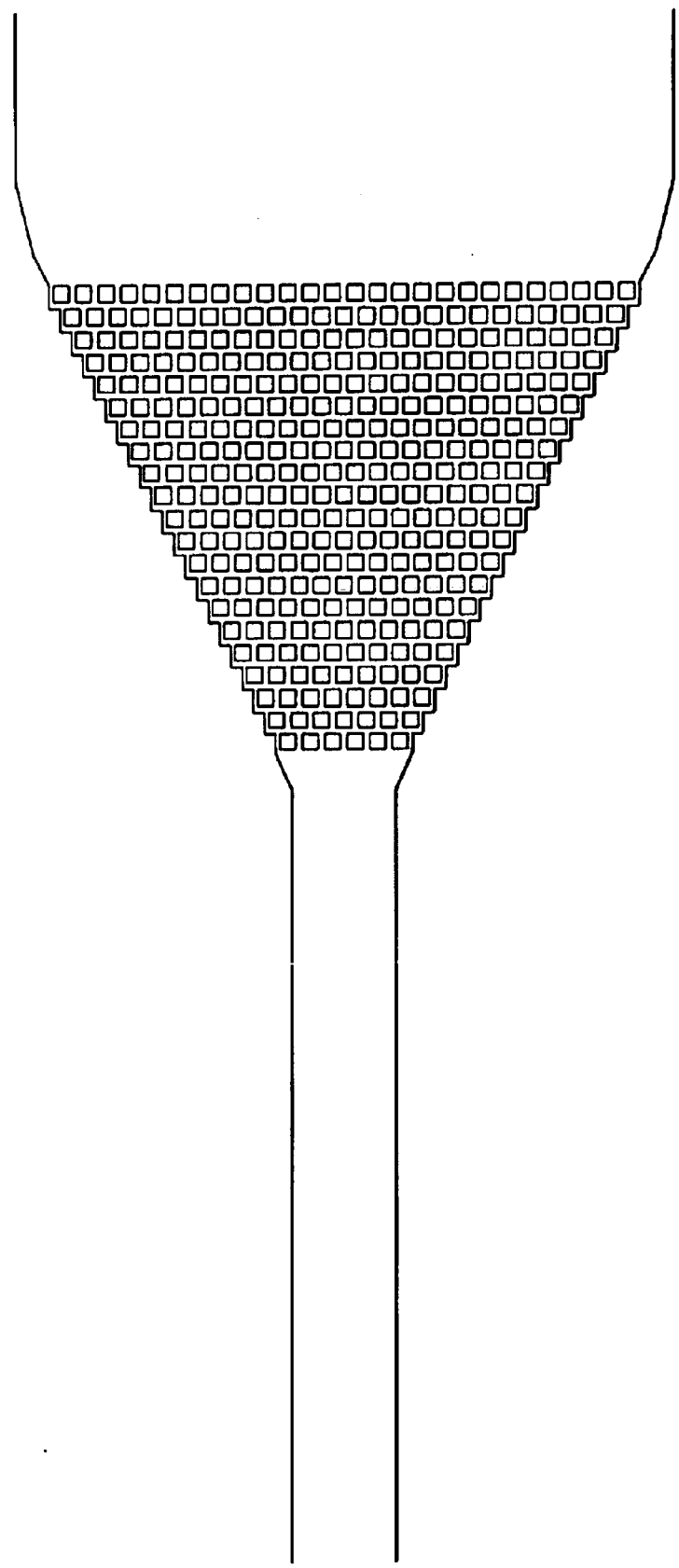
Figure 4L:
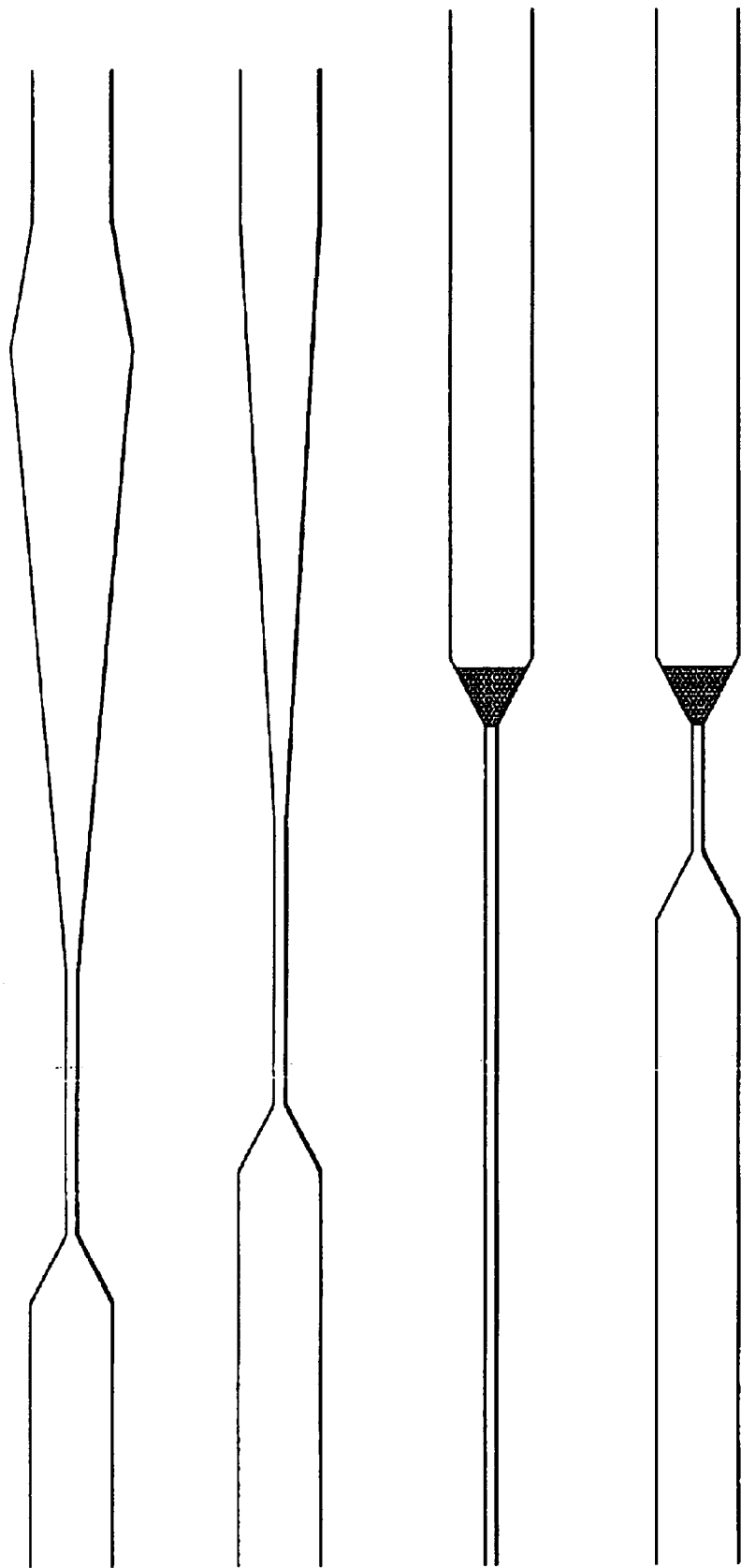
Figure 4M:
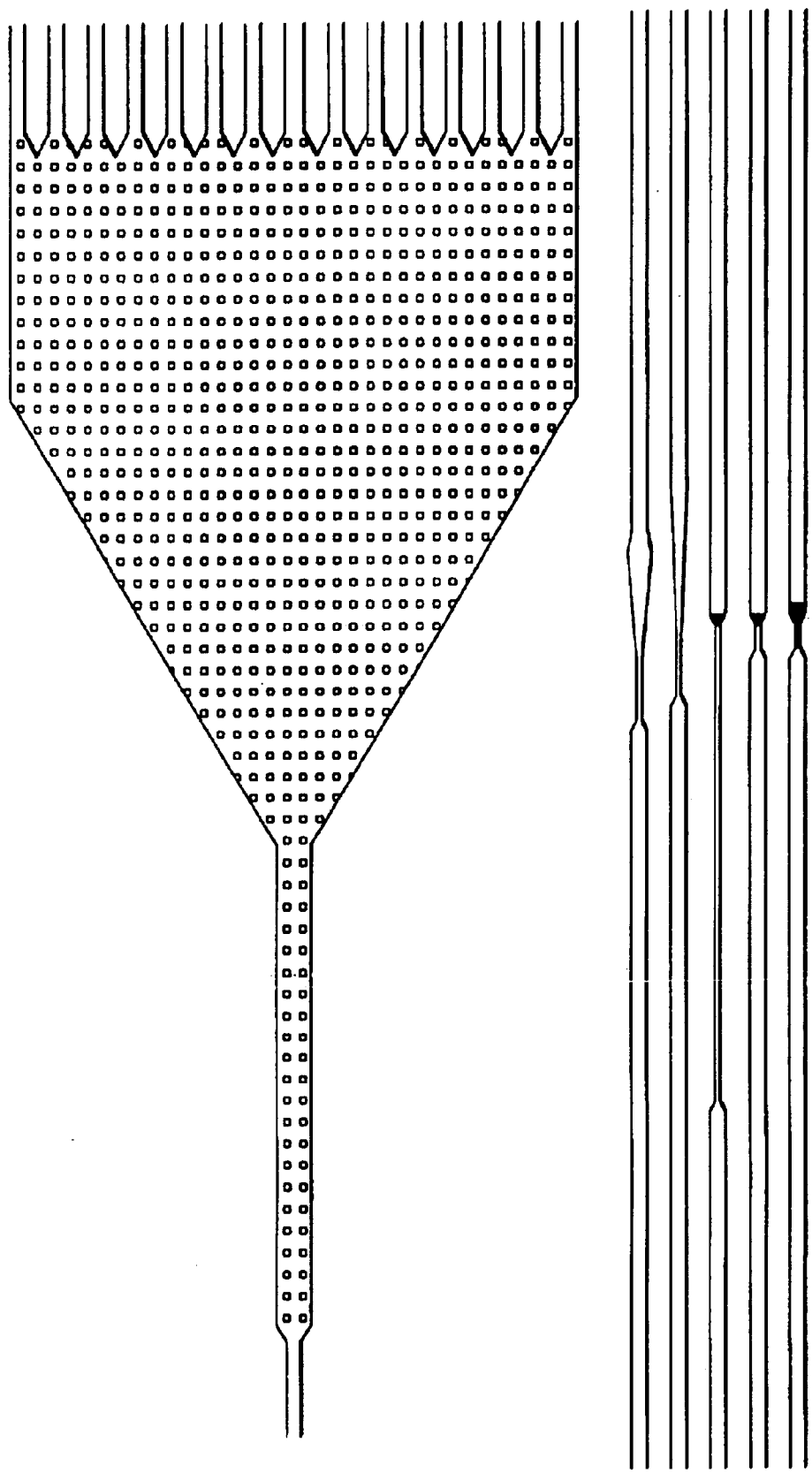

Examples of structures (FIG. 3) that fall within the scope of the invention include, but are not limited to:

1) funnels with a non-linear increase in fluid velocity;
2) funnels with a linear increase in fluid velocity;
3) funnels with obstacles defining small gaps as the region of DNA elongation;
4) funnels with a non-linear increase in fluid velocity and obstacles defining small gaps;
5) funnels with a linear increase in fluid velocity and obstacles defining small gaps;
6) funnels with mixed obstacle sizes and gaps, including a gradient of obstacles sizes and gaps;
7) branched structures having regions of increased fluid velocity from converging channels;
8) branched structures having multiple regions of increased fluid velocity from multiple converging channels;
9) branched structures having obstacles defining small gaps;
10) branched structures which have at least one funnel as one of the branches;
11) branched structures with mixed obstacle sizes and gaps, including a gradient of obstacle sizes and gaps;
12) structures which have obstacles which define small gaps and also bends or curves;
13) structures which have obstacles defining small gaps which have a periodicity (sine patterns, boxcar repeats, zig-zags);
14) structures which have obstacles defining small gaps which are non-quadrilateral polygons;
15) structures having a mixture of obstacles which define small gaps, e.g., a set of bars defining small gaps juxtaposed to a field of sine patterns, or a field of triangles, circles, or stars;
16) structures having obstacles defining small gaps integrated with funnels, branched structures, or bends or curves;
17) structures having bends or curves in a funnel shape;
18) structures having bends or curves with obstacles defining small gaps;
19) structures having regions of DNA elongation in series;
20) structures having regions of DNA elongation in parallel;
21) structures having multiple delivery channels with respective regions of elongation;
22) structures having three-dimensional geometries involving embodiments of the other categories; and
23) structures which are closed loops containing regions of DNA stretching.

Further examples of structures that fall within the scope of the invention are shown in FIGS. 4(a–l). These include several embodiments of stretching structures involving funnels, obstacles, branches, and serial structures; two funnel structures with posts in serial; embodiments of several complex post arrangements and branched structures; an asymmetric branched structure; a structure with a combination of small obstacles that define small gaps; a structure with a combination of polygonal, bar, and post obstacles; an asymmetric bent structure; a branched structure having posts; a large funnel structure with support posts; a funnel structure with posts; funnel structures with a linear increase in flow rate both with and without posts. FIG. 4(m) is a summary of some of the possible funnel structures. Typically, the elongation structures of the invention can have lengths from 1 μm to 2 cm. Preferably the elongation structures of the invention have lengths from 1 μm to 1 mm, widths of from 2 μm to 1 mm, and depths of from 0.1 μm to 10 μm.

Each of the four main components of a functional polymer elongation and stretching structure are described below.

Funnel Structures

Figure 5:
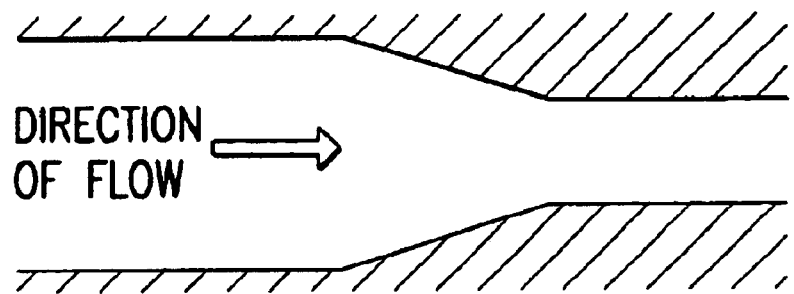

Funnel structures are tapered channels that apply elongational forces in a regular and continuous manner as the polymer flows down the channel. The characteristics of the elongational forces are determined by the type of channel structure and shape. In one embodiment of the invention, the channel is a tapered channel (FIG. 5) that begins at a first width at a first end and continuously decreases to a second width at a second end, creating an elongational force in the funnel portion of the channel as characterized by a strain rate:

$$du/dx=(-Q/H)(dW/dx)(1/W^2) \tag{15}$$

In one embodiment of the invention, the width decreases linearly so that dW/dx is constant; and the strain rate, du/dx, of a flow in the channel thus increases as W decreases. In this embodiment, the angle of the funnel as measured as a deviation from a straight wall starting from the first end is preferably between 1° and 75°, with a most preferred value of 26.6° for DNA in a low viscosity solution such as TE (10 mM TRIS, 1 mM EDTA) buffer, pH 8.0. Starting widths for the linear funnel embodiment preferably range from 1 micron to 1 cm, with ending widths preferably in the range of 1 nm to 1 mm depending on the polymer of interest, with most-preferred values of 50 microns and 5 microns, respectively, for DNA.

Figure 6:
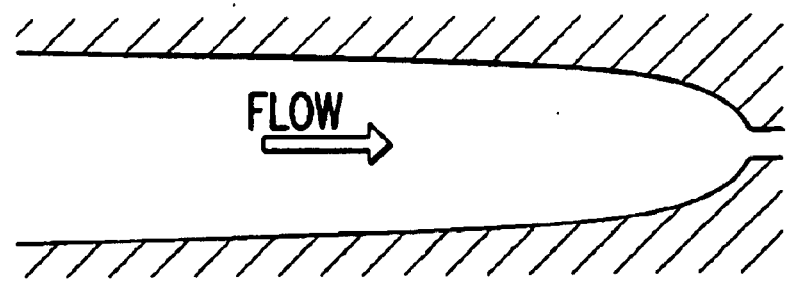
FIG. 6 shows an embodiment of a tapered channel which gives rise to an elongational flow component of rapidly increasing strain rate.

The channel could also be configured such that the width decreases at a rate faster than linear rate (FIG. 6), resulting in higher rate of increase in strain rate as the channel is traversed. Such tapered channels offer especially good protection against natural relaxation of the polymer, since as time passes and the molecules move down the channel, they experience increasing elongational forces to counter their tendency to recoil. Furthermore, the increasing force tapered channel allows more design flexibility; any polymer that will encounter elongational forces large enough to cause the polymer to stretch in the tapered channel and will not encounter elongational forces large enough to cause the polymer to break in the tapered channel can be successfully run through the tapered channel and stretched. There is no need to find the ideal or threshold force for the polymer, only an effective range. In embodiments involving pressure-driven fluid flow (see Driving forces, below), more rapidly increasing strain rate also offers the greatest increase in velocity for a given pressure drop, since the final velocity is a function of the cross-sectional area and the pressure drop is a function of the cross-sectional area and length of channel. The same small cross-sectional area (and hence large velocity) can be reached in a shorter distance (and hence smaller pressure drop). In a preferred embodiment, the width of the funnel, W, decreases as $1/(ax^n+b)$, where n is any real number greater than 1, a is a nonzero real number, b is a real number, and x is distance along the length of the funnel, e.g, measured from the starting end (and the direction of polymer flow). Potential equations for width of a tapered channel include $W=1/x^2$, $W=1/x^3$, etc.

Figure 7:
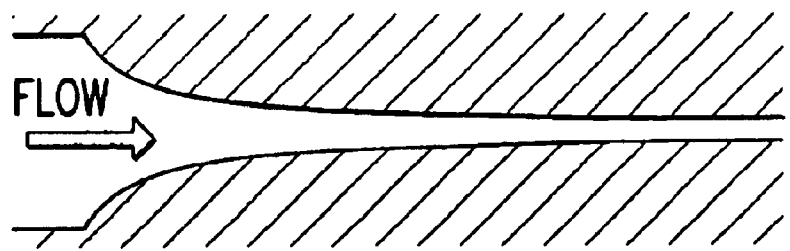
FIG. 7 shows an embodiment of a tapered channel which gives rise to an elongational flow component of constant strain rate.

In yet other embodiments, channels are designed such that the strain rate is constant, leading to a tapered channel such as that shown in FIG. 7. The value of the constant strain rate required to achieve an adequate force to completely stretch the polymer over the course of the channel will vary depending on the length of that channel (see, e.g., Eq. (14)). Therefore, 0.01/s might be a reasonable strain rate in order to completely stretch a polymer in a very long, e.g. >1 cm, channel, but might result in almost no polymer stretching in a very short, e.g. <10 µm, channel. Lengths of channels may vary significantly, with preferred values from 10 µm to 1 cm and the most preferred values in the range of 1–2 mm. In one embodiment, the channel is 1 mm long and the shear rate is 0.075/s.

The strain rate of the funnel can be determined by standard methods known in the art, e.g., PIV.

Branched Channels

Figure 8:
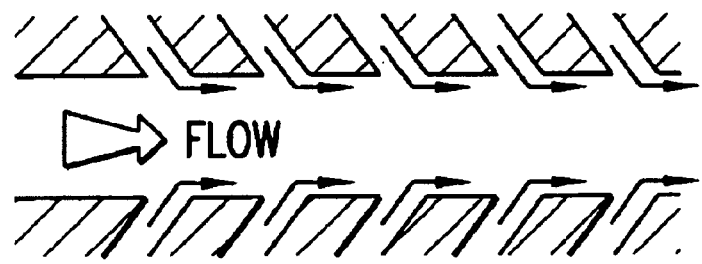
FIG. 8 shows an embodiment of a branched channel structure in which the elongational force comes from the addition of fluid from side channels.

A second aspect of the invention used to stretch and elongate polymers is to create branched structures, which cause either changes in fluid flow rates or changes in flow directions (see below in Structures with bends or curves). Side channels feed more fluid into a main channel, resulting in a change in fluid velocity and hence causing polymer stretching. A typical arrangement of branched channels is shown in FIG. 8. Side channels preferably have a combined cross-sectional area ranging from about 1% to 500% of the cross-sectional area of the main channel. Most preferably, side channels have a combined cross-sectional area of about 50% of the cross-sectional area of the main channel. In one embodiment, the side channels are present in a pattern that is repeated, which results in a dilution of the elongational force at each individual entrance to the main channel and, hence, a closer approximation of a constant elongational flow situation. This arrangement highlights the advantages and disadvantages of the side channels. One disadvantage of this component of polymer elongation is that all of the force in the main channel fluid is dissipated in a relatively small region near the junction of the main channel and the side channels. Therefore, this configuration does not lead to a constant-force situation. However, an advantage of this component of polymer elongation is that, because the fluid added from the side channels is moving in the same direction as the fluid in the main channel, it creates a substantial elongational flow component. A shear flow is a superposition of an elongational flow and a rotational flow. The elongational flow stretches a polymer in the direction of the fluid flow, because the portion of the polymer located in a region downstream moves faster than a portion still located in a upstream region. The rotational force causes the polymer to spin or "tumble" in conformation, which can cause stretched portions of the polymer to fold up on themselves and recoil. In the embodiments that have stronger elongational flow, such as the side channel junction configuration, the polymer tends to accelerate away from the junction, which results in lower rotational forces, thus allowing for better stretching.

As will be appreciated by those of skill in the art, the channel dimensions may be modified and the flow rate increased in the same region of the chip. In fact, a significant increase in the flow rate followed by a constant strain rate section is one way not only to stretch out a polymer, but also to direct it away from the walls of the channel. One arrangement embracing this embodiment of the invention is shown in FIG. 9. In yet another embodiment, additional flow is brought in only from one side of the main channel, thereby positioning a polymer traveling down the main channel toward one side. This positioning design could be used to ensure that a polymer is aligned to pass under a narrow detector in a broader channel.

Structures with Bends or Curves

The third aspect of the invention uses tortuosity to achieve stretching. As fluid flow encounters changes in its path, alignments ranging from a small bend to a right angle, the fluid on the outside of the curve or corner will take longer to go around the turn than the fluid on the inside of the curve or corner (FIG. 10(a)). This so-called "racetrack effect" can help stretch out polymers. Such a bend does not include a "T" junction. In a rectangular section of a channel, a polymer may flow such that it straddles more than one fluid flow line, and since the fluid in each line travels at the same velocity, it retains its configuration. In contrast, when the distance traveled by each fluid flow line diverges at a bend or corner, the polymer is stretched locally by the velocity differential. Furthermore, the polymer tends to move toward the higher-velocity flow line, so that even if the channel curves back to regain its original direction, the polymer does not fully recoil because locally it is within the same flow line. A possible sequence of this kind of stretching is shown in FIG. 10(b). While this effect is insufficient to stretch an entire long molecule in a single set of turns, it can gradually uncoil specific regions, and enough repetition of a tortuous channel can stretch an entire molecule.

One of the gentler incarnations of the tortuosity regime is an embodiment where the configuration of the channel follows a sine wave pattern (FIG. 11). In another embodiment, the channel takes the form of a zig-zag shape (FIG. 12), or, in yet a further embodiment, even a "snake"-shape with only right-angle corners (FIG. 13), though this severe of a corner tends to cause stagnant flows and other undesirable fluid dynamics. For those embodiments where the channel has a zig-zag shape, each bend preferably has an angle between 5° and 75°; for DNA a preferred value of every such angle is 26.6 (effectively a 53.4° angle where the zig-zag reverses). Such zig-zag shapes may be periodic, in which the angle of the bends is always the same, or may comprise a pattern of differential bends. The period of repetition for the zig-zags may vary from as little as 2 µm to 1 cm, with preferred values of 20–50 µm for DNA (1000 times the persistence length). For those embodiments where the channel has a sinusoidal shape, the amplitude to period ratios are preferably between 0.01 and 5. The number of periods for any of these patterns may vary from 1 period to 500, with a preferred value of 10.

In a further embodiment, tortuous channels are used to create multiple detection possibilities. When a detector, such as a position-dependent photomultiplier tube arranged in a 1×256 array, is situated along the direction of flow in the channel, the tortuous channel can be aligned so that it repeatedly crosses the detection zone at defined locations. The polymer being stretched is then observed at several locations, creating redundancy and error checking in the system. Such an arrangement is shown in FIG. 14, with fluid traveling down channel 111 passing through detection zone 110 at six locations, 112–117.

Obstacles Defining Small Gaps

The fourth aspect of structures which tend to cause stretching is the field of obstacles. As described more generally above, obstacles induce stretching both by reducing the available cross-sectional area of the channel (causing local strain on the molecules) and by acting as physical barriers which cannot be passed by large coils of polymer. One example is a configuration of posts that work to actually stretch a polymer and is shown in FIG. 15.

The obstacles can vary in cross-sectional shape and in cross-sectional area. The terms "cross-sectional shape" and "cross-sectional area," as used herein with reference to obstacles, and unless otherwise indicated, refer to the shape of the X-Y projection and the area of the X-Y plane of the obstacle, respectively, as shown in FIG. 16. In particular embodiments, the obstacles comprise square posts, round posts, elliptical posts or posts with a rectangular cross-section of any aspect ratio (including extremely long "bars"); in other embodiments, the obstacles comprise posts with a cross-section shaped as a regular or irregular non-quadrilateral polygon. In one preferred embodiment, the cross-sectional shape is triangular. In other preferred embodiments, these shapes are modified to have a concave edge on the edge that faces the direction from which the fluid is coming (such as a shallow U-shape). In still other embodiments, posts having a cross-sectional shape wherein one dimension is longer than the other preferably have an aspect ratio of 2 to 20, more preferably of 2 to 5.

Figure 17B:
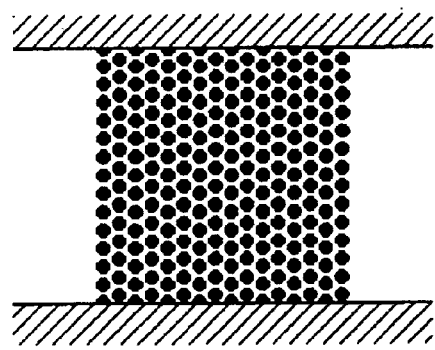

Each of these obstacles may be placed at any angle to the direction of flow. In preferred embodiments, the obstacles are aligned with either a flat surface perpendicular to the direction of the flow, or at a 45° angle to the flow, though if preferential positioning of the polymer molecules is desired, other angles which physically direct polymers toward a destination would be used. Preferably, obstacles wherein one dimension is longer than the other are placed with their longer dimension perpendicular to the flow direction. Another factor in the layout of the obstacles is the grid on which they are placed. If placed on a repeating square matrix (FIG. 17(a)), certain fluid flow lines are almost unaffected by the obstacles, and unstretched or poorly stretched polymers may be able to track along these flow lines and make it through the obstacle field without being stretched. To prevent this, each successive column is preferably offset to place the next obstacle where the gap in the previous column had been (FIG. 17(b)), forcing all flow lines to have curvature and inducing stretching on all passing molecules. The offset may also be less than the full 50% of the repetition unit so that every other column is not in the same alignment as shown in the figures; every fourth or sixth column may have an identical alignment, for example, or there may never be a repetition of alignment, as long as the flow lines at some point are forced to curve around an obstacle.

Besides alignment in the flow, there are two other parameters relevant for obstacles: the size of the passages between them, and the total Y-Z cross-sectional area of the posts relative to the Y-Z cross-sectional area of the channel (FIG. 16), both of which affect the preferred obstacle size. The width of the passages between obstacles should not be smaller than the diameter of the stretched polymer, and is preferably not less than approximately 50 times the diameter of the stretched polymer in order to increase the probability that the polymer will be able to pass through the channel without becoming stuck in the obstacle field. An example of inadequate passage width leading to polymers not getting through the obstacles is shown in FIG. 18. On the other hand, the passages are preferably not as wide as the diameter of the coiled polymer, in which case the coil could pass through the obstacle field without having to stretch at all. Hence, the preferred spacing of the obstacles is highly dependent on the polymer being analyzed. In the case of long DNA with a chain diameter of 2 nm and a coiled diameter varying upward from about 1 µm, the passage width is preferably between 100 nm and 800 nm, with a most preferred value equal to 500 nm. For polymers with a very small diameter, gels may be used in place of obstacle fields, giving pore sizes (equivalent to passage width in the fields) of 1 nm to 1000 nm.

The total Y-Z cross-sectional area occupied by the obstacles most directly impacts the velocity gradients that occur in between the obstacles, and which encourage stretching. Hence, it is preferable to have a larger ratio of obstacle Y-Z cross-sectional area to total channel Y-Z cross-sectional area (also known as the fill ratio, which when expressed as a percentage is given by 100 multiplied by the ratio of the total area of the posts to the total area of the channel) to maximize the velocity gradients. On the other hand, forcing too much material through a relatively small gap can lead to clogging if more than one polymer tries to enter a channel at the same time. Hence, to balance these competing considerations, the fill ratio is preferably between 33% and 95%. This is the ratio of occluded area to total area in a particular channel expressed as a percentage. For example, a post having a 1 µm² Y-Z cross-sectional area in a channel having a 3 µm² Y-Z cross-sectional area has a fill ratio of 33%, while a 20 µm² post in a 21 µm² channel has a fill ratio of 95%. The most preferred value for the fill ratio is between 50% and 80% for DNA. An example of obstacles too large, leading to clogging, is shown in FIG. 19.

In order to alleviate problems with polymers clogging small passages in the post field, differential passage widths are used in some embodiments of the invention. In some embodiments, this is accomplished by varying the size of the obstacles. In other embodiments, this is accomplished by varying the fill ratio. In still other embodiments, both obstacle size and fill ratio are varied. In such embodiments, polymers first encounter wide passages between obstacles and subsequently encounter passages of decreasing widths (FIG. 20), forcing them to gradually become more elongated in order to proceed down the smaller channels. In a preferred embodiment, passage widths are gradated from about 5 µm per passage to about 1 µm per passage in the flow direction. In another embodiment, post sizes are gradated from a cross-sectional area of about 10 µm² to about 1 µm² in the flow direction. In other embodiments, the obstacle cross-sectional area and passage width may be varied individually to achieve similar effects, i.e., the obstacle size may change and the passage size may remain constant, or the passage size may change and the obstacle size may remain constant. In a preferred embodiment, all obstacles have the same cross-sectional area, but the fill ratio increases in the flow direction. The cross-sectional area of the posts can vary from 0.1 µm² to 1 mm², preferably from 0.1 µm² to 10 µm², more preferably from 1 µm² to 100 µm², even more preferably from 1 µm² to 25 µm², depending on the size of the polymer being stretched and the size of the channel used. Such pre-alignment of polymers serves to decrease the possibility of entanglement and hence provides more predictable stretching.

Obstacles can also be fabricated into the depth or z-dimension of the structures, i.e., by introducing "steps" into the top and/or bottom of the channel to decrease the depth. Instead of having obstacles placed across a channel, as discussed above, the entire channel can change in depth, providing the same kind of barrier and shear forces around the barrier as obstacles placed along the width of the channel. Furthermore, changes in depth can be relatively inexpensive to implement, as controlling the depth of etching on the sub-micron scale is generally easier than trying to create feature sizes on the sub-micron scale using photolithography. Without being bound by any theory, a significant change in depth at a specific location in essence creates the same effect as a single row of posts, or as a funnel of infinitely short length, x. To approximate a funnel in a fashion that is easy to manufacture using standard microfabrication techniques, the height change can be designed to occur in several steps along the length of the channel, instead of in one step at a single location. In a preferred embodiment, a single-step configuration reduces the height of the channel by a factor of five. In other embodiments, a configuration having at least one step reduces the height of the channel from by about a factor of 2 to by about a factor of 100. In still other embodiments, the steps vary in height from about 0.1 µm to about 0.9 µm.

Combinations of Components

In further embodiments of the invention, the four general aspects of structures, i.e., tapered, branched channels, tortuous, and obstacle-filled, are used in combination. An elongational flow of constant strain rate in a tapered channel, for example, is good not only at stretching in itself, but in maintaining stretching in polymers that have already been stretched by obstacle fields. A channel with a tortuous contour can also shrink in width following a constant-shear pattern to capitalize on both effects. In preferred embodiments, a gradated obstacle field or alignment structure is used to pre-stretch the polymer, followed by a section of fine obstacles, tortuous patterns, or high strain rate area to complete the stretching, and a constant strain rate or increasing strain rate section to maintain the stretching until the detection point is reached.

Applicants have found that an especially effective structure is a combination of an obstacle field upstream of a tapered channel. The obstacle field serves to uncoil the DNA from its random coil configuration, presenting one end of the molecule preferentially to the downstream structure(s). It is advantageous for the obstacle field to be in a wide region of the channel where the flow velocity is relatively low such that the drag force applied to a molecule that becomes folded around or otherwise retained by one of the obstacles is not sufficient to break the molecule. As the molecule winds through the obstacle field, one end will tend to lead the rest of the molecule and enter the tapered channel first. The molecule will then be further stretched by the elongational force of the flow through the tapered channel. Without being bound by any theory, applicants have found that the partial uncoiling and end presentation effected by the obstacle field combined with the stretching in the tapered channel is especially effective in accomplishing DNA stretching. Comparison of experimental data from a tapered channel with an upstream post field to data from a tapered channel alone, shows that better stretching is achieved by the combination of the post field and tapered channel under similar conditions of flow and temperature. The experimental data shows that, while a tapered channel does stretch DNA, a structure that combines a tapered channel with a post field provides significantly greater stretching on average and stretches a greater proportion of the DNA.

In preferred embodiments, an obstacle field, step or alignment structure is used to pre-stretch and align the polymer, followed by a section comprising an elongational flow of constant or increasing strain rate to complete and maintain the stretching until the detection region is reached. Preferably, the obstacle field is matched with a tapered channel in a way that avoids contractile flow (i.e., decreasing velocity). Hence it is preferred that posts or steps are located in or terminate at a tapered portion of the channel.

In more preferred embodiments, the channel is a two-funnel structure, that is, it has two tandem regions with different degrees of tapering. An example of a two-funnel structure is shown in FIG. 21. In one embodiment, the two-funnel structure further comprises a post field in the first tapered region. In the two-funnel configuration, stretching of the polymer is completed in the second tapered region (right-most channel region in FIG. 21). Pressure driven flow is the preferred driving force because of its simplicity and ease of application.

In a most preferred embodiment, the structure has a first channel region with a constant width of about 10 µm and a height of about 1 µm in which is placed an obstacle field along the flow direction and leading into a second channel region that is a funnel whose width tapers as $1/x^2$, from a width of about 10 µm to about 1 µm, and whose height is reduced in a single step at the entrance to the funnel from about 1 µm to about 0.25 µm (FIG. 22). The ratio of the initial channel width to the final channel width is preferably greater than 10, and the length of the funnel portion is preferably less than one-half the initial width. The obstacle field preferably comprises at least between 12 and 15 rows of posts having a cross-sectional area substantially equal to 1 µm, wherein the rows have an increasing fill ratio in the flow direction. In one embodiment, six rows have an increasing fill ratio from 0% to 50% in the flow direction, and the subsequent 12–15 rows have a constant fill ratio of 50%, wherein the centers adjacent rows of the subsequent 12–15 rows are at a distance of about 2 µm (FIG. 22). In another embodiment, the rows have a continuously increasing fill ratio from 0% to 80% in the flow direction.

It will be apparent to one skilled in the art that any one or combination of the elongational structures described in this section can be used in conjunction with any methods and apparatuses described in Sections 5.2–5.4, supra.

5.5.2. Structures for Polymer Selection by Length

As described in the previous section, post fields can be used to produce non-random alignment of polymers and to effectively separate one end of the polymer chain from the random coil that is the equilibrium structure of the polymer in solution. If a post field is placed at a distance L from the mouth of a tapered channel, which can be of any shape desired to maintain or produce stretching, e.g., straight, constant strain rate, or higher order polynomial, the resulting structure can also be used to select molecules by length. This process is illustrated in FIG. 23.

FIG. 23 shows a schematic view of a post field constructed according to the methods described below (see Methods of fabricating structures), positioned before a funnel region of elongational flow. Because the posts fill a portion of the channel, fluid moving through the channel will experience a decrease in velocity as it moves from the post region into the post-free section of the channel. This decrease in velocity allows the polymer to re-coil. DNA molecules that travel along the channel and become hooked around a post will be stretched by the flow. If the molecule has a length equal to or longer than the distance L from the posts to the start of the tapered region, it will be released from the post field into the region of elongational flow, in effect spanning the region of decreased fluid velocity without recoiling, and will remain stretched, as shown schematically by DNA molecule 1 in FIG. 23. If the molecule is shorter than L, e.g., DNA molecule 2 in FIG. 23, then it will leave the posts while still in the post-free region before entering the tapered channel, where it will contract rapidly into an coil. Therefore, a molecule having a length greater than or equal to L will be stretched and a molecule having a length less than L will not be stretched. If a detector is positioned at the exit from the funnel, as shown in FIG. 23, the signals from coiled molecules (length less than L) and stretched molecules (length greater than or equal to L) will be distinguishable. For example if the detector were monitoring intercalator-stained DNA, contracted molecules would produce a short, intense burst of fluorescence signal, whereas fully-stretched molecules would produce a longer, less intense fluorescence signal. Thus it is possible to produce structures that separate mixed populations of polymers into two groups, i.e., those having lengths shorter than L and those having lengths equal to or longer than L, by simply setting L, the distance from the trailing end of the post field to the mouth of the tapered region, to a length that is substantially the same as the length of the molecules from which signal is to be detected.

In another embodiment, it may be desirable to stretch and uniformly detect signal from molecules of all lengths in a given population. This can be done by eliminating the region of post-free region between the post field and the tapered channel, by, e.g., extending the post field of FIG. 23 into the channel, as shown in FIG. 24. Since the detector is located at the entrance to the channel (as in FIG. 23), where the post field ends, all molecules will be stretched as they pass the detector, and therefore, signals from all molecules, regardless of their lengths, will be detected. In these embodiments, the flow remains constant because the area between the posts is matched to the channel area to which the post field extends.

5.5.3. Design Considerations

Stretching Considerations and Types of Structures to be Used

Different structures give rise to different types of DNA stretching and elongation. There is tethered stretching and uniform stretching. Tethered stretching entails creating an unequal force distribution on one end of the molecule to create full extension in a flow profile. Tethered stretching is straightforward to create using obstacles defining small gaps. Uniform stretching, on the other hand, is more complex and involves extensive modeling of polymer dynamics. Uniform stretching is defined as creating a uniform tension over each unit of the DNA molecule. Structures which are designed to create uniform stretching include those with constant elongational forces in the x-direction of the design such as funnels with non-linear increases in flow rates.

Polymer Size Considerations

The structural designs are such that they are scalable and some are universal. Structures can be increased in size, and the relative dimensions changed, in order to accommodate polymer molecules of different lengths. Sizes of interest range from several kilobases to at least megabases of DNA, although there is no upper limit on the length of polymer molecules that can be accommodated. One megabase of DNA has a contour length over 300 microns. Channel dimensions can be made up to several millimeters. In this manner, whole chromosomes (ranging in size from 50–250 megabases) can be handled and stretched.

Configurations of Channels on Overall Chip

The delivery channels leading to the regions of DNA elongation can include delivery channels which are parallel, radial, branched, interconnected, and closed loops. Delivery channels in the preferred embodiment are wide channels, i.e., 1–1000 microns, which lead to regions of DNA stretching and elongation.

Methods of Fabricating Structures

The preferred method to fabricate the designed structures is by lithography, such as e-beam lithography, deep-uv lithography, photolithography, LIGA (acronym of the German words "Lithographie," "Galvanoformung," and "Abformung," meaning lithography, electroplating, and molding), and elastomeric molding. Two and three dimensional structures are fabricated by these techniques. Further methods to create three dimensional defined channels include track-etching and molding techniques.

Other methods to create nano-sized obstacles include methods that involve chemical means such as photodeposition of colloids, self-assembly of localized polymers, and cross-linked networks of polymers. For example, a non-linear funnel with localized deposition of agarose gel in the funnel can create an environment of controlled stretching.

Delivery Mechanisms

Structures intended to stretch out the polymer are not the only ones which may be useful to place in a channel. Structures designed to position the polymer favorably in one part of a channel over another are useful in ensuring that the polymer is fed to a particular stretching structure or to a particular detection zone. Besides the adding of fluid to a single channel as mentioned above (see Branched channels) the positioning can also be accomplished by forcing flow lines closer together. Polymers driven by fluid flow (induced by any of the later-cited methods such as pressure differential and gravity) will principally follow the fluid flow lines (in electrophoresis for charged biopolymers, the polymer follows the field lines, which can be similarly modified). Random motion can cause portions of the chain to move to an adjacent flow line. If the flow lines encounter a constriction or obstacle, the flow lines become closer together around the obstacle, leading to a greater chance that the same lateral random motion will cause a change in flow lines. As the flow lines return to their original spacing on the other side of the structure (if the channel returns to its original width), velocity gradients between the flow lines tend to draw the polymer toward the faster flow lines. In this way, the formerly random distribution of polymer can be made to shift to something more regular. In one embodiment, for example, a large triangle in the middle of a channel with a side perpendicular to the channel facing downstream tends to orient polymers toward the center; this is because polymers formerly near the walls tend to be pulled toward the center by the fluid moving laterally on the downstream side of the triangle. In other embodiments, other shapes are used to help in positioning, such as cross-shaped obstacles, wedges, and obstacle fields with offsets that tend to direct larger channels at a particular side of the channel. While it might seem intuitive that a channel with a simple bend in it should have a positioning effect, the velocity gradients involved are actually quite small and the effect by itself is quite modest.

Methods to Improve Stretching in Structures

In further embodiments of the invention, the effectiveness of the elongational flow regimes is enhanced by increasing the viscosity of the solution. The actual force exerted on a polymer by fluid flow is proportional to the viscosity of the solution. In some embodiments, the viscosity of the solution is increased by the addition of one or more viscosity-modifying components. Glycerol (with a viscosity of nearly 900 cP at room temperature) can be added to an aqueous solution in concentrations as high as 70% (w/v) if it does not react chemically with the polymer. Sugars, such as sucrose, xylose, and sorbitol may also be added. Water-soluble polymers, such as polyethylene glycol, may also be added. In the case of DNA, high molecular weight polyacrylamide, polyethylene oxide or long-chain length polysaccharides (even at concentrations as low as 0.01% by weight) can increase the viscosity of aqueous solutions without modifying the structure of the DNA being characterized.

The viscosity may also be modified by adding an amount of the polymer being characterized, but which will not be detected by the detection zones of the structures. For example, if FRET is being performed on an extrinsically labeled DNA molecule, then additional DNA molecules that are not extrinsically labeled may be added to the labeled polymer solution in order to increase the viscosity. In this way, only labeled molecules are detected and the unlabeled DNA serves only to modify the viscosity of the solution, but does not interfere with signal generation from the labeled molecules.

In another embodiment, viscosity is increased by decreasing the temperature. For example, the viscosity of pure water nearly doubles as it approaches the freezing point. In addition to increasing the viscosity, a decrease in temperature is also helpful to minimize Brownian motion and to extend relaxation times. There is a substantial improvement in stretching when an aqueous buffer solution, such as 1X TE solution (10 mM TRIS, 1 mM EDTA), is changed from ambient temperature to 4° C.

Driving Forces

The driving force for moving the polymer through the structures can come from any means, including physical, electrical, thermal, or chemical forces. The simplest driving force is allowing flow to be driven by capillary action as the first contact is made between the sample solution and the device. While the surface energies involved can provide a high velocity in the channel, control of the flow in this approach is limited.

The use of chemical potential allows for indirect, and hence limited, control. One advantage of setting up a concentration gradient is to provide an extremely slow, steady flow rate. This is accomplished by creating a large excess of a species at one side of the structures and consuming the diffusing species after it induces fluid flow through the structures to the other side, with control based on the excess concentration. The polymer flows through the structures along with the fluid whose flow is induced by the migrating species.

In a preferred embodiment directly controlled fluid flows are used. In such an embodiment, a pressure head is established on the entrance side of the structures, encouraging the fluid to flow to the far side, opened to atmospheric pressure or maintained at reduced pressure. The pressure head may come from any device imposing a physical force, such as a syringe pump. Currently, syringe pumps dispense up to the 100 pL/s range, and desired flow rates in a device may be under 1 pL/s, meaning that it may be necessary to create a "bypass channel" with a large cross-sectional area, thus increasing the desired flow rate of the device and allowing control with off-the-shelf equipment, with the loss only of some volume of sample. In another embodiment of a pressure control system, in devices with a pressure drop, e.g., one end of the system is pulled with a vacuum, thereby sucking material to be stretched through the structures. The pressure drop required to induce flow at a desired velocity is a function of the channel geometry (especially the minimum cross-sectional dimension) and that velocity, but is typically within an order of magnitude of 10 psi for 100 micron per second flow in a millimeter-long, micron-deep channel which is otherwise quite wide through most of the device. In another embodiment, a combination of a pressure head at a first end of the channel and a pressure drop, e.g., vacuum at a second end of the channel are used to propel a polymer from the first end to the second end.

In yet a further embodiment, the polymer is controlled through the fluid flow by setting up a temperature gradient on each side of the stretching zone. Natural convection then creates a fluid flow through the stretching zone. Since it is much harder to create and control temperature gradients on the micron scale on which these devices operate, this method, like the chemical potential method, is preferably used for very low fluid flow.

In still another embodiment, the movement of the polymer is controlled, for charged polymers such as DNA, by setting up an electric field which acts on the charges on the polymer and not necessarily on the surrounding fluid at all (if it is uncharged). The electric field is preferably established by the presence of two oppositely-charged electrodes in solution, but entire arrays of electrodes can be used to create more complicated or uniform field patterns. The polymers then follow electric field lines instead of flow lines (in some instances an inconsequential change, depending on the physical layout of the chip and the charge density of the solution). This can be damaging to stretching if the surrounding solution contains oppositely-charged objects which flow in the opposite direction (electro-kinetic flow), or surface charges on the wall of the channels causing flow of ions along the walls (electro-osmotic flow), either of which can induce fluid flow in that opposite direction and impart viscous forces on the polymer. However, in a low conductivity solution with walls appropriately coated to avoid surface charge, opposing viscous forces have negligible impact on the electrophoretic driving force, allowing the polymer to proceed through the structures and become stretched. In addition, with an appropriately-charged wall surface, the electro-osmotic flow can be reversed to provide viscous forces which assist the electrophoretic stretching. A field strength of 1000 to 2000 V/m results in usable polymer velocities in the 100 micron per second range.

In cases of electrophoresis and pressure driving forces, the devices creating the driving force are generally physically separated from the stretching zone. The electrodes are located several millimeters to multiple centimeters away from the stretching zone, with the power supply located even further away. The syringe pump, while advantageous to be as close to the stretching zone as possible to minimize the needed pressure drop, will tend to be placed outside of the device because of its bulk. In fact, for the sake of structural flexibility, it is preferred to place only the stretching and detecting structures themselves on a small chip, preferably no larger than 2 cm on a side, and perhaps as small as 1 mm square, with a most preferred size (from the standpoint of human handling) of about 1.5 cm by 1 cm, with a thickness of 0.2 cm. On that substrate, a variety of fluid flow channels are located. In such a chip, anywhere between 1 and 160 channels may be comfortably placed on the substrate, with 30–40 striking a good balance between having redundancy in the case of channel blockage or substrate flaws and having only one channel in a detection field of view at one time (with a typical 60x objective).

Substrates

The substrate used is selected for compatibility with both the solutions and the conditions to be used in analysis, including but not limited to extremes of salt concentrations, acid or base concentration, temperature, electric fields, and transparence to wavelengths used for optical excitation or emission. The substrate material may include those associated with the semiconductor industry, such as fused silica, quartz, silicon, or gallium arsenide, or inert polymers such as polymethylmethacrylate, polydimethylsiloxane, polytetrafluoroethylene, polycarbonate, or polyvinylchloride. Because of its transmissive properties across a wide range of wavelengths, quartz is a preferred embodiment.

The use of quartz as a substrate with an aqueous solution means that the surface in contact with the solution has a positive charge. When working with charged molecules, especially under electrophoresis, it is desirable to have a neutral surface. In one embodiment, a coating is applied to the surface to eliminate the interactions which lead to the charge. The coating may be obtained commercially (capillary coatings by Supelco, Bellafonte Pa.), or it can be applied by the use of a silane with a functional group on one end. The silane end will bond effectively irreversibly with the glass, and the functional group can react further to make the desired coating. For DNA, a silane with polyethyleneoxide effectively prevents interaction between the polymer and the walls without further reaction, and a silane with an acrylamide group can participate in a polymerization reaction to create a polyacrylamide coating which not only does not interact with DNA, but also inhibits electro-osmotic flow during electrophoresis.

The channels may be constructed on the substrate by any number of techniques, many derived from the semiconductor industry, depending on the substrate selected. These techniques include, but are not limited to, photolithography, reactive ion etching, wet chemical etching, electron beam writing, laser or air ablation, LIGA, and injection molding. A variety of these techniques applied to polymer-handling chips have been discussed in the literature, including Harrison et al. (Analytical Chemistry 1992 (64) 1926–1932), Seiler et al. (Analytical Chemistry 1993 (65) 1481–1488), Woolley et al. (Proceedings of the National Academy of Sciences November 1994 (91) 11348–11352), and Jacobsen et al. (Analytical Chemistry 1995 (67) 2059–2063).

Additional Considerations

In preferred embodiments of the invention, the velocity in a given planar height of the channel is substantially uniform in a rectangular channel. This is true when the height is significantly less than the width of the channel, such that the no-slip condition at the wall results in a viscosity-induced parabolic velocity profile that is significant in the height axis, leaving only a small boundary region of slower flow in the width axis. An aspect (width/height) ratio of approximately 10 or greater is required for such embodiments, according to the lubrication theory approximation (Deen, Analysis of Transport Phenomena, New York: Oxford University Press, 1998. 275–278). Furthermore, a small height assists in detection when using a microscope objective in an optical system. Typical objectives may have a depth of focus of 500 nm to several microns, so while the depth of channel could be anywhere from 50 nm to 100 $\mu$m as long as the aspect ratio is kept above 10 to accommodate the polymer being analyzed, the preferred embodiments have channel depths of 200 nm to 1 $\mu$m such that all material passing by in a channel will be in focus and accurately observed.

The invention also encompasses embodiments where the channels are not planar, and are fabricated with three dimensional channel fabrication techniques. In such embodiments, constant shear is induced not only from side walls, but from a gradient in channel height. Similarly, in further embodiments, combinations of structures have one force acting on one axis and the other force acting in the other. In some such embodiments, an obstacle field spans the width of the channel as its height decreases in a tapered shape. In other embodiments, a tortuous, inward-spiral design in a single plane which also decreases in channel width is used to impart shear forces which feed at its center into a vertical exit from the device through a hole in the bottom of the material, with detection near the entrance to the hole. When structures exist in the vertical dimension, gravity is used in some embodiments to help create velocity differentials in the fluid. (Notably, gravity alone is not adequate to stretch a polymer or move it significantly with a flow since the force on a 100 kD polymer is barely more than $10^{18}$ N; any effect of gravity will be felt by the molecule through viscous forces.)

5.6. Computer Implementation

The methods of the present invention are preferably implemented using a computer system. Accordingly, such computer systems are also considered part of the present invention. The computer system include a processor interconnected with memory. For example, computer system can have an Intel Pentium®-based processor of 200 MHZ or greater clock rate and with 32 MB or more memory. In a preferred embodiment, the computer system has an Intel Pentium III processor of 833 MHz. The computer system can also include a mass storage, e.g., one or more hard disks. The computer system of the invention can further comprise other mass storage units including, for example, one or more floppy drives, one more CD-ROM drives, one or more DVD drives or one or more DAT drives. The computer system typically also includes a user interface device, e.g., a monitor, a keyboard and a "mouse." The computer system is also typically linked to a network link which can be, e.g., part of a local area network ("LAN") to other, local computer systems and/or part of a wide area network ("WAN"), such as the Internet, that is connected to other, remote computer systems. In one embodiment, the computer system of the invention is connected to a computer which controls experiments such that experimental data, e.g., signal amplitude profiles, can be downloaded for analysis.

One or more software components can be loaded into the memory during operation of such a computer system. The software components comprise both software components that are standard in the art and components that are special to the present invention. These software components are typically stored on mass storage such as the hard drive, but can be stored on other computer readable media as well including, for example, one or more floppy disks, one or more CD-ROMs, one or more DVDs or one or more DATs. Software components that can be loaded into the memory of the computer include an operating system which is responsible for managing the computer system and its network interconnections. The operating system can be, for example, of the Microsoft Windows™ family such as Windows 95, Window 98, Windows NT or Windows 2000. Alternatively, the operating software can be a Macintosh operating system, a UNIX operating system or the LINUX operating system. Software components also include programs that allow implementation of the methods of the present invention, e.g., determining velocities from signal amplitude profiles. Languages that can be used to program the methods of the invention include, for example, C and C++, FORTRAN, PERL, HTML, JAVA, and any of the UNIX or LINUX shell command languages such as C shell script language. The methods of the invention can also be programmed or modeled in mathematical software packages that allow symbolic entry of equations and high-level specification of processing, including specific algorithms to be used, thereby freeing a user of the need to procedurally program individual equations and algorithms. Such packages include, e.g., Matlab from Mathworks (Natick, Mass.), Mathematica from Wolfram Research (Champaign, Ill.).

In addition to the exemplary program structures and computer systems described herein, other, alternative program structures and computer systems will be readily apparent to the skilled artisan. Such alternative systems, which do not depart from the above described computer system and programs structures either in spirit or in scope, are therefore intended to be comprehended within the accompanying claims.

6. EXAMPLES

Elongation and Analysis of Phage Lambda DNA

The following examples are presented by way of illustration of the present invention, and is not intended to limit the present invention in any way. In particular, the examples presented herein below describe the analysis of the lambda DNA.

6.1 EXAMPLE 1

Fabrication of a Chip For Stretching DNA and its use in an Apparatus for Detecting Fluorescene Emission From Labeled DNA Experimental Apparatus A sensitive optical apparatus for detection is shown in FIG. 25. The apparatus utilizes confocal fluorescence illumination and detection. Confocal illumination allows a small optical volume (of the order of femtoliters) to be illuminated. Both Rayleigh and Raman scattering are minimized using a small probe volume. The beam from a 1 mW argon ion laser is passed through a laser line filter (514 nm), directed to a dichroic mirror, through a 100×1.2 NA oil immersion objective, and to the sample. The fluorescent tag on the DNA can be one of several dyes including Cy-3, tetramethylrhodamine, rhodamine 6G, and Alexa 546. In addition, intercalator dyes can be used such as TOTO-3 (Molecular Probes). The fluorescence emission from the sample is passed through a dichroic, a narrow bandpass (e.g. Omega Optical), focused onto a 100 μm pinhole, passed through an aspheric lens, and ultimately focused onto an avalanche photodiode in photon counting mode (EG&G Canada). The output signal is collected by a multichannel scalar (EG&G) and analyzed using a Pentium III type computer. The confocal apparatus is appropriate for quantitative applications involving time-of-flight. Such applications include measuring distances on the DNA, detecting tagged sequences, and determining degrees of stretching in the DNA. Single fluorescent molecules can be detected using the apparatus. For applications requiring imaging, an apparatus using an intensified CCD (ICCD, Princeton Instruments) mounted on a microscope is appropriate.

Fabrication of the Chip

A set of tapered channels with a design strain rate of 0.085/s preceded by two rows of 1.5 micron obstacles on a 2 micron pitch were created in a 0.090 inch thick quartz substrate by photolithography and e-beam methods. The substrate was first cleaned by placement in an RCA solution (5 parts deionized water to 1 part 30% ammonium hydroxide/30% hydrogen peroxide, the latter two from Sigma Chemical Co., St. Louis, Mo.) heated to 80° C. for twenty minutes, and dried under a nitrogen stream. Shipley S1813 photoresist diluted in a 2:1 ratio with type R thinner (Shipley, Newton, Mass.) was then spun onto the quartz surface at 3250 rpm for 45 seconds in a spin coater and cured at 90° C. in an oven for 0.5 hours. The coarse constant-shear pattern was then contact printed onto the surface by a 12 s exposure to a mercury lamp, e.g., in a contact aligner from Carl Zeiss, Germany, followed by a 30 s rinse under 351 developer (Shipley) diluted in a 5:1 ratio with deionized water, further rinses in deionized water, and drying under a nitrogen stream. After a 10 s UV-ozone cleaning, the substrate was exposed to a 40 minute etch by $CHF_3$ in a Reactive Ion Etch (RIE) machine. After another wash in RCA solution, a solution of polymethylmethacrylate (650 MW) diluted to 3% in chlorobenzene was spun onto the surface at 2000 rpm for 45 seconds in a spin coater. The coating was cured for one hour in an oven at 180° C., and a 60 A layer of chrome was added in an evaporator. An e-beam write was performed to make the fine structures, e.g., the rows of obstacles, followed by a chrome etch in the REI machine and a deionized water rinse. The substrate was then immersed for 90 seconds in a 2:1 v/v solution of isopropyl alcohol:methyl-isobutyl ketone heated to 21° C. for developing, followed by another UV-ozone cleaning. Another $CHF_3$ etch in the REI machine followed by a wash with RCA solution were then performed.

Cover slips (Fisher Scientific, Pittsburgh, Pa.) of dimensions 45 mm×50 mm×0.15 mm were rinsed with deionized water and dried under a nitrogen stream. A 10:1 w/w solution of RTV615A:RTV615B silicone (General Electric, Schenectady, N.Y.) was spun onto the cover slips for 60 seconds at 4000 rpm in a spin coater and was then cured at 80° C. for two hours. A slab of silicone with a hole where the chip is mounted was placed on a cover slip, which was then exposed to a 30 W plasma cleaner for 50 seconds in order to make the surface hydrophilic. The silicone slab was then removed and the cover slip was rinsed in deionized water and dried under nitrogen. The fully-prepared chip was then carefully mounted onto the cover slip.

Apparatus for Monitoring Object-dependent Impulses from Stretched DNA

As shown in FIG. 26, the delivery system consists of a polymer supply 151, which is driven by a syringe pump 150 through a chip 152 (see above) where the polymer is stretched out and excited by a laser beam from laser 154 which is detected by optical detector 153 and analyzed by computer 155 that also controls the pump 150 and detector 153.

Monitoring Fluorescence Emission in Stretched DNA

Coliphage T4 DNA (Sigma, St. Louis, Mo.) was labeled by the addition of 4040-1 at a 5:1 (base-pair:dye) ratio, incubation for one hour, and dilution by a factor of 50,000 in 0.5X TBE electrophoresis buffer (45 mM TRIS, 32.3 mM boric acid, and 1.25 mM EDTA at pH 8.3, all from Sigma, St. Louis, Mo.).

One microliter of sample was then pipetted onto the cover slip immediately next to the chip, where it was loaded into the channels by capillary action. The chip and cover slip were placed on the stage of a fluorescence microscope (Microphot series from Nikon) equipped with a 60×plano apo lens (from, e.g., Nikon or Carl Zeiss). Excitation was from a mercury arc lamp, with a Nikon 2A filter set ensuring adequate excitation near the 490 nm peak excitation of YOYO-1. Emission above 520 nm was passed through the B2A filter set and captured by a silicon-intensified camera (Hammamatsu's C2400-08) or by a CCD camera. The image from the camera was output to a computer through an image capture card (such as the PCI-1408 from National Instruments, Austin, Tex.) and analyzed with image processing software, which was a custom-written routine that identified the DNA on the screen based on its brightness against background and counted pixels to determine polymer length.

Various DNA molecules were observed in this apparatus (FIG. 27). A DNA molecule of approximately 190 kb (63 microns) is shown stretching out in the constant-shear section of the chip in FIG. 28(a–g). A DNA fully stretched out in the chip is shown in FIG. 29. This molecule was measured at 139 microns, or 535 kb.

Data

A small (half-microliter) sample of T4 DNA (Sigma) stained with YOYO-1 (Molecular Probes) was loaded into a chip with a rectangular funnel section incorporating posts and run under capillary action. The sample was excited with a 100 W Hg lamp and observed with a SIT camera (Hammatsu C2400-08). The video signal from the camera was fed to a video capture card in a Pentium-class computer running custom LabView software that determined the length of a piece of DNA in pixels based on its velocity and time spent in the region of interest. Lengths of less than 30 microns were considered to be fragments and were discarded automatically, which led to the obtaining of only ten data points in the approximately two minute run of sample. Using a known conversion for the level of magnification, the DNA were found to be 50.6 µm long, with a range between 42 and 62 µm. A histogram is shown in FIG. 30. The length is somewhat shorter than the expected value of 71.1 µm for a stained 164 kbp T4 DNA, implying the stretching in this design was not fully complete.

6.2 Example 2

Stretching of Phage Lambda DNA Using Apparatuses of the Invention

Figure 31A:
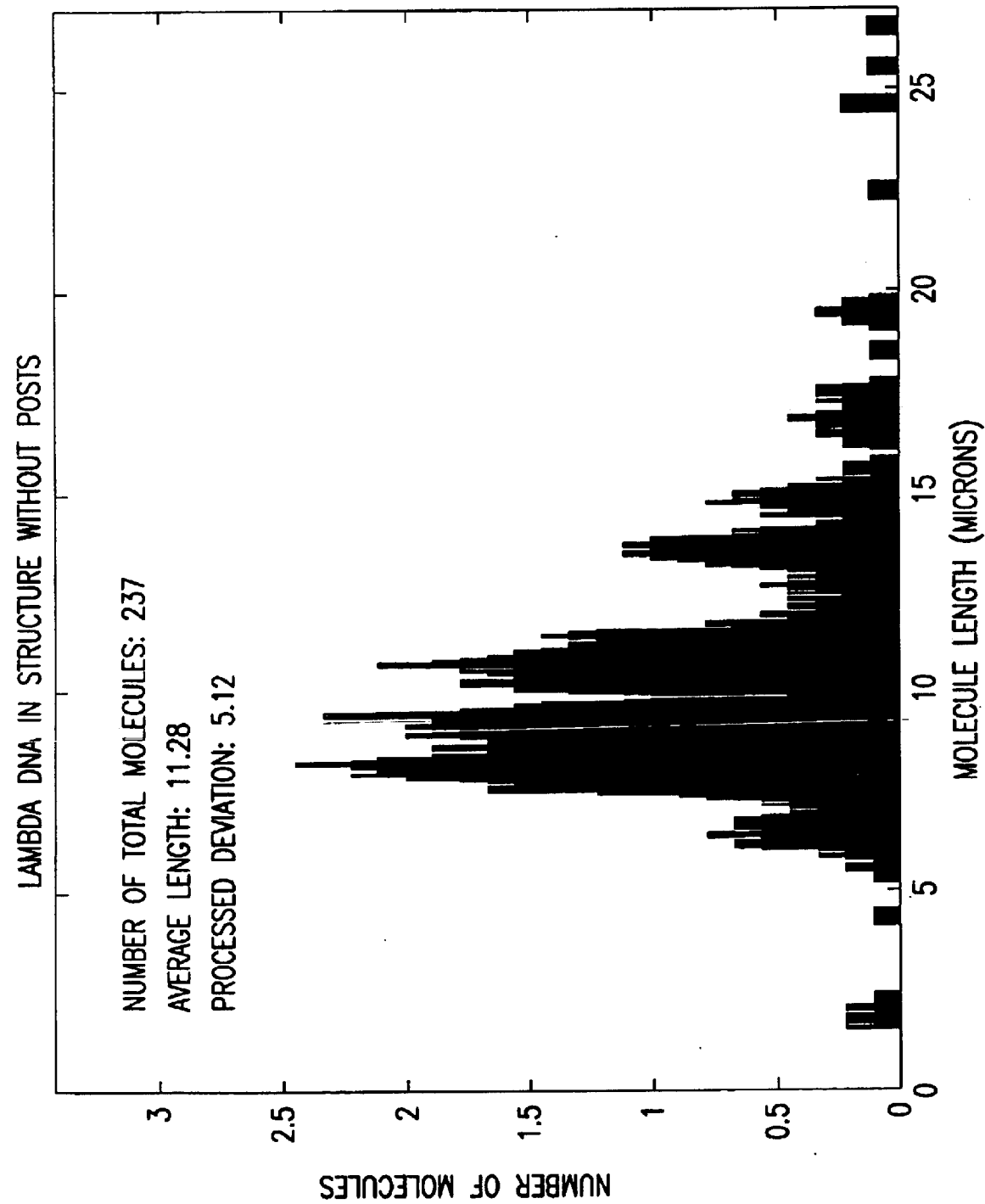

Two different apparatuses were used to obtain the data shown in FIG. 31(a) and 31 (b). The apparatus shown in FIG. 21 was used to obtain the data shown in FIG. 30(b).

Figure 31B:
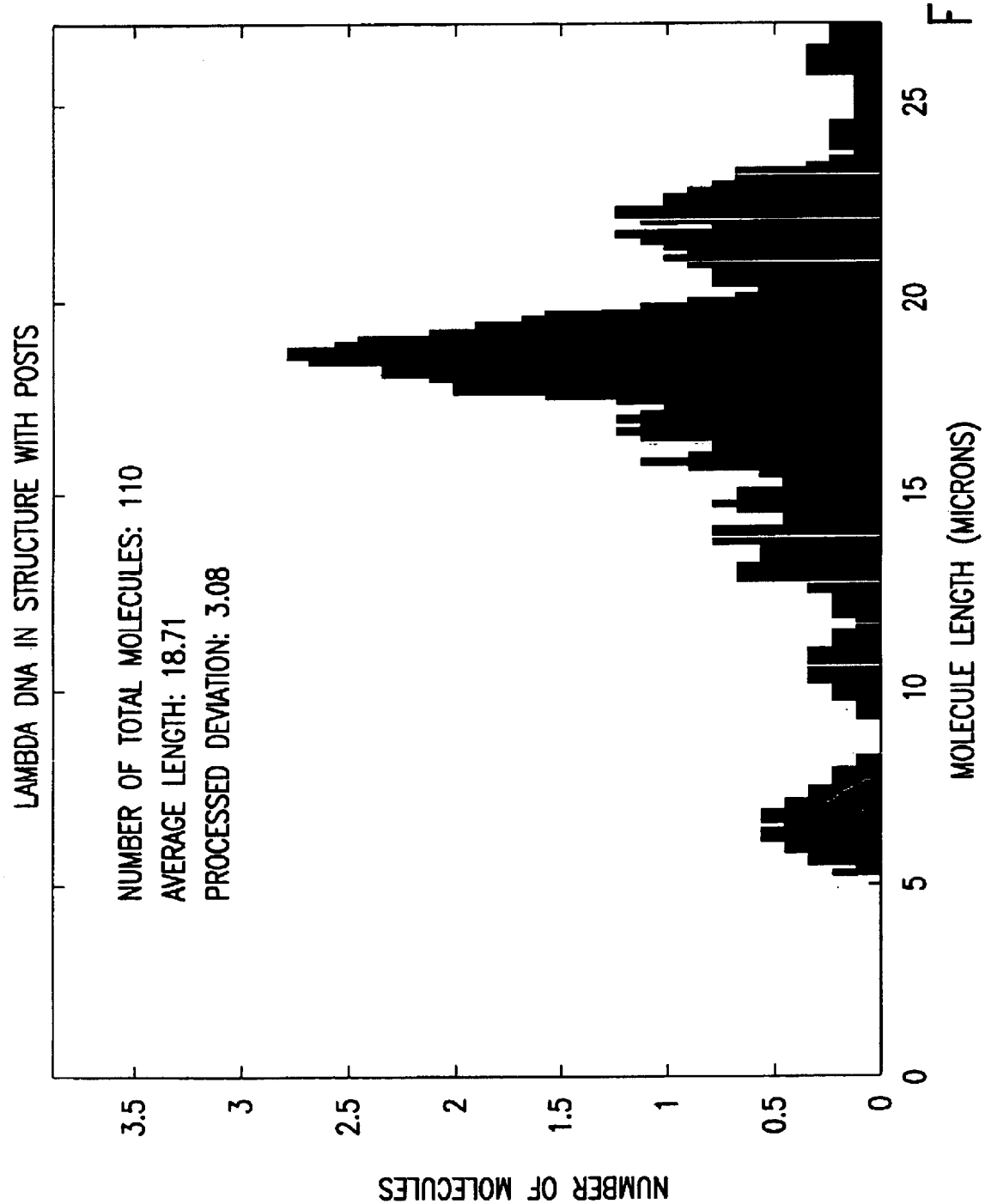

The apparatus used to obtain the data in FIG. 31(a) had the same channel boundaries as the apparatus used to obtain the data shown in FIG. 31(b) (i.e., the ratio of the sizes of the two tapered regions of the two-funnel apparatus were identical), except that there were no posts present in the structure.

A fused silica wafer (Hoya Corp., San Jose, Calif.) was etched with the pattern in FIG. 21 by a contractor using photolithographic methods described above. The wafer was diced into 1 cm by 2 cm chips using a dicing saw (e.g. from Disco Corp., Santa Clara, Calif.), and a fused silica cover slip (e.g. from Esco, Oak Ridge, N.J.) was attached by thermal bonding.

Double stranded lambda DNA (Promega, Madison, Wis.) having a uniform length of 48.5 kilobases (i.e., an anticipated stretched length of 16–17 microns), was labeled by addition of a like amount of 3 µM TOTO-3 iodide (Molecular Probes, Eugene Oreg.) intercalating dye and then diluted by a factor of approximately 50,000 in 1×TE buffer (10 mM TRIS, and 1 mM EDTA at pH 8.0, all from Sigma, St. Louis, Mo.). The anticipated stretch length of lambda DNA stained with an intercalating dye is 21 µm (approximately 30% longer than unstained DNA) for the double stranded 48.5 kilobase DNA sample used here.

The chip and cover slip were placed on the microscope stage of a fluorescence microscope (e.g., Microphot series from Nikon) equipped with a 100×piano apo lens (e.g., from Nikon, Carl Zeiss) and a filter set optimized for use with TOTO-3 (e.g., XF-47 from Omega Optical, Brattleboro, Vt.). Excitation was from a 633 nm HeNe laser (e.g., from Melles Griot) focused on two spots aligned on the same flow line within the microchannel. The sample was loaded at the entrance of the channels by capillary action and the flow sustained using a vacuum at the other end of the chip (created by a vacuum pump from, e.g., Welch Vaccum, Skokie, Ill.). As DNA molecules passed through the laser spots, emission above 650 mn was passed through the filter set and captured by a pair of confocal detectors aligned above the spot. Time of flight between the detectors was used to determine velocity, which was used along with residence time in a laser spot to calculate the lengths of the molecules.

The results of these experiments indicate that the two-funnel apparatus comprising posts stretches 48.5 kilobases of double-stranded, dye-stained lambda DNA to a length of approximately 19.5 µm (FIG. 31(b)), whereas the two-funnel apparatus without posts only stretches the DNA to a length of about 10 µm (FIG. 31(a)). Thus, although there is stretching of the DNA in the tapered channel without posts, on average, the DNA is stretched only to somewhat more than half of its full length and very few individual molecules are fully stretched, as is evidenced by the wide distribution of the histogram in FIG. 31(a). By contrast, in the structure having a post field combined with a downstream tapered channel, the molecules are, on average, stretched to close to full length and the majority of molecules are within 20% of their anticipated fully-stretched length. Therefore, the two-funnel apparatus with posts stretches DNA better than the same apparatus without posts. Furthermore, this apparatus stretches the polymers more uniformly and efficiently than the two-funnel structure without posts.

6.3 Example 3

Stretching of Phage Lambda DNA Using Apparatuses of the Invention

The data shown in FIGS. 37–39 were derived from a dual laser spot arrangement as illustrated in FIG. 36. The DNA was driven through a quartz chip with etched nanochannel of the following design: The depth of the quartz chip is 300 nm. The chip was fabricated using electron beam lithography that involved a series of steps known in the art, which include coating the quartz wafer with a resist, exposing the required areas using a resist using the electron beam, stripping the exposed resist, and etching using reactive ion etch to give straight wall profiles, and finally removing the resist. The laser used to excite dye molecules was a argon ion laser running at 488 nm. The laser delivers about 2 mW of laser power to each of the spots. The spots were diffraction limited, with a spot size of approximately 0.5 microns in diameter. The laser spots were separated 15 $\mu$m apart and located along the direction of the flow and thus direction of the DNA molecules movement so that the laminar flow lines of the fluid allowed the DNA to be delivered through the two detection zones, i.e., the two regions of laser excitation and detection. The DNA molecules measured were lambda DNA that has been intercalated with YOYO-1 at a final concentration of 1 YOYO-1 molecule/10 base-pairs. The solution containing the DNA contained 100 mM DTT in a 1×TBE solution. A fluid drive, delivering 50 psi, was used to drive the DNA through the channel. The chip has been sealed using typical sealing techniques involving chemical activation of the surfaces using a ammonium hydroxide:peroxide::water mixture, heated to 70° C. for treatment of both the quartz chip and also the quartz coverslip. The coverslip and the quartz chip were then pressed together under water and the clamped package was baked at high temperatures 300° C. to 1000° C. to allow evaporation of any solvent and chemical bonding of the two surfaces. The DNA sample mixture was then introduced into the chip by capillary forces. The signals measured from the two laser excitation spots, arranged 15 microns apart, were collected through a Nikon 1.4 NA 100×oil immersion objective. The resultant fluorescent signals were filtered and detected by two avalanche photodiodes. The signals from the two intercalator signals were then collected through a data capture board, a A/D converter, and stored on a computer. The computer allowed processing of the data and calculation of the lengths of the molecules. In this particular case, a constant velocity estimation was used to derive the velocity of the molecules moving through the system. The velocity was a COM to COM velocity estimation/calculation. The average length of the lambda molecules was measured to be around 18 microns, corresponding to an approximate 20% increase in the length of the DNA molecule from the intercalator staining. The data was processed using an algorithm written in MATLAB data processing language.

7. REFERENCES CITED

All references cited herein are incorporated herein by reference in their entirety and for all purposes to the same extent as if each individual publication or patent or patent application was specifically and individually indicated to be incorporated by reference in its entirety for all purposes.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. A method for determining velocity of a single elongated polymer said method comprising measuring a plurality of signal amplitude profiles of said elongated polymer, each signal amplitude profile comprising measurements taken at a different one of a plurality of detection zones, wherein said plurality of detection zones consists of a first and a second detection zone, as the elongated polymer moves along a path past the first and second detection zones and determining said velocity of said elongated polymer from said plurality of signal amplitude profiles, wherein said plurality of signal amplitude profiles consists of a first signal amplitude profile comprising measurements taken at said first detection zone and a second signal amplitude profile comprising measurements taken at said second detection zone, wherein each said signal amplitude profile comprises measurements in the first and second detection zones of a signal generated at said elongated polymer at a plurality of times, said plurality of times comprising times that are before, during, and after said elongated polymer is in said detection zones, wherein said plurality of detection zones are located in order along the path of said elongated polymer at predetermined distances, and wherein said plurality of signal amplitude profiles are measured in a time-correlated manner, wherein said velocity of said elongated polymer is a center-of-mass velocity and wherein said determining said velocity comprises (a) determining temporal location of a first center-of-mass in said first signal amplitude profile and temporal location of a second center-of-mass in said second signal amplitude profile; and
  (b) calculating said center-of-mass velocity by dividing distance between said first and second detection zones with difference between temporal locations of said first center-of-mass and said second center-of-mass.

2. A method for determining velocity of a single elongated polymer, said method comprising measuring a plurality of signal amplitude profiles of said elongated polymer, each signal amplitude profile comprising measurements taken at a different one of a plurality of detection zones, wherein said plurality of detection zones consists of a first and a second detection zone, as the elongated polymer moves along a path past the first and second detection zones and determining said velocity of said elongated polymer from said plurality of signal amplitude profiles, wherein said plurality of signal amplitude profiles consists of a first signal amplitude profile comprising measurements taken at said first detection zone and a second signal amplitude profile comprising measurements taken at said second detection zone, wherein each said signal amplitude profile comprises measurements in the first and second detection zones of a signal generated at said elongated polymer at a plurality of times, said plurality of times comprising times that are before, during, and after said elongated polymer is in said detection zones, wherein said plurality of detection zones are located in order alone the path of said elongated polymer at predetermined distances, and wherein said plurality of signal amplitude profiles are measured in a time-correlated manner, wherein said velocity of said elongated polymer is a center-to-center velocity and wherein said determining said velocity comprises (a) determining temporal location of a first center of polymer contour in said first signal amplitude profile and temporal location of a second center of polymer contour in said second signal amplitude profile; and
  (b) calculating said center-to-center velocity by dividing distance between said first and second detection zones with difference between temporal locations of said first center of polymer contour and said second center of polymer contour.

3. A method for determining velocity of a single elongated polymer, said method comprising measuring a plurality of signal amplitude profiles of said elongated polymer, each signal amplitude profile comprising measurements taken at a different one of a plurality of detection zones, wherein said plurality of detection zones consists of a first and a second detection zone, as the elongated polymer moves along a path past the first and second detection zones and determining said velocity of said elongated polymer from said plurality of signal amplitude profiles, wherein said plurality of signal amplitude profiles consists of a first signal amplitude profile comprising measurements taken at said first detection zone and a second signal amplitude profile comprising measurements taken at said second detection zone, wherein each said signal amplitude profile comprises measurements in the first and second detection zones of a signal generated at said elongated polymer at a plurality of times, said plurality of times comprising times that are before, during, and after said elongated polymer is in said detection zones, wherein said plurality of detection zones are located in order along the path of said elongated polymer at predetermined distances, and wherein said plurality of signal amplitude profiles are measured in a time-correlated manner, wherein said velocity of said elongated polymer is an end-to-end velocity and wherein said determining said velocity comprises (a) determining temporal location of a first leading end in said first signal amplitude profile and temporal location of a second leading end in said second signal amplitude profile; and (b) calculating said end-to-end velocity by dividing distance between said first and second detection zones with difference between temporal locations of said first leading end and said second leading end.

4. The method of claim 3, wherein said temporal location of said first leading end and said temporal location of said second leading end are identified as the times at half heights of the respective leading edges in said first and second signal amplitude profiles.

5. A method for determining velocity of a single elongated polymer, said method comprising measuring a plurality of signal amplitude profiles of said elongated polymer, each signal amplitude profile comprising measurements taken at a different one of a plurality of detection zones, wherein said plurality of detection zones consists of a first and a second detection zone, as the elongated polymer moves alone a path past the first and second detection zones and determining said velocity of said elongated polymer from said plurality of signal amplitude profiles, wherein said plurality of signal amplitude profiles consists of a first signal amplitude profile comprising measurements taken at said first detection zone and a second signal amplitude profile comprising measurements taken at said second detection zone, wherein each said signal amplitude profile comprises measurements in the first and second detection zones of a signal generated at said elongated polymer at a plurality of times, said plurality of times comprising times that are before, during, and after said elongated polymer is in said detection zones, wherein said plurality of detection zones are located in order along the path of said elongated polymer at predetermined distances, and wherein said plurality of signal amplitude profiles are measured in a time-correlated manner, wherein said velocity of said elongated polymer is a rise-time velocity and wherein said determining said velocity comprises (a) determining time interval of rising edge of said first or second signal amplitude profile measured in a respective detection zone; and (b) calculating said rise-time velocity by dividing dimension of said respective detection zone with said time interval of rising edge of said first or second signal amplitude profile.

6. A method for determining the length of a single elongated polymer, said method comprising:

(a) measuring a first signal amplitude profile of said single elongated polymer at a first detection zone as the single elongated polymer moves along a path past the first detection (b) measuring a second signal amplitude profile of said single elongated polymer at a second detection zone as the single elongated polymer moves alone the path past the second detection zone;

(c) determining a velocity of said single elongated polymer at said first and second detection zones from said first and/or second signal amplitude profiles; and (d) determining length of said single elongated polymer by multiplying time difference between leading and trailing edges of said first or said second signal amplitude profile with said velocity;

wherein each said signal amplitude profile comprises measurements in the respective detection zone of a signal generated at said single elongated polymer at a plurality of times, said plurality of times comprising times that are before, during and after said elongated polymer is in said detection zone, wherein said first and second detection zones are located in order along the path of said single elongated polymer at predetermined distances, and wherein said first and second signal amplitude profiles are measured in a time-correlated manner, wherein said velocity of said single elongated polymer is a center-of-mass velocity and wherein said determining a velocity comprises (a) determining temporal location of a first center-of-mass in said first signal amplitude profile and temporal location of a second center-of-mass in said second signal amplitude profile; and (b) calculating said center-of-mass velocity by dividing distance between said first and second detection zones with difference between temporal locations of said first center-of- mass and said second center-of-mass.

7. A method for determining the length of a single elongated polymer, said method comprising:

(a) measuring a first signal amplitude profile of said single elongated polymer at a first detection zone as the single elongated polymer moves along a path past the first detection zone;

(b) measuring a second signal amplitude profile of said single elongated polymer at a second detection zone as the single elongated polymer moves along the path past the second detection zone;

(c) determining a velocity of said single elongated polymer at said first and second detection zones from said first and/or second signal amplitude profiles; and (d) determining length of said single elongated polymer by multiplying time difference between leading and trailing edges of said first or said second signal amplitude profile with said velocity;

wherein each said signal amplitude profile comprises measurements in the respective detection zone of a signal generated at said single elongated polymer at a plurality of times, said plurality of times comprising times that are before, during and after said elongated polymer is in said detection zone, wherein said first and second detection zones are located in order along the path of said single elongated polymer at predetermined distances, and wherein said first and second signal amplitude profiles are measured in a time-correlated manner, wherein said velocity of said single elongated polymer is a center-to-center velocity and wherein said determining a velocity comprises (a) determining temporal location of a first center of polymer contour in said first signal amplitude profile and temporal location of a second center of polymer contour in said second signal amplitude profile; and (b) calculating said center-to-center velocity by dividing distance between said first and second detection zones with difference between temporal locations of said first center of polymer contour and said second center of polymer contour.

8. A method for determining the length of a single elongated polymer, said method comprising:

(a) measuring a first signal amplitude profile of said single elongated polymer at a first detection zone as the single elongated polymer moves along a path past the first detection zone;

(b) measuring a second signal amplitude profile of said single elongated polymer at a second detection zone as the single elongated polymer moves along the path past the second detection zone;

(c) determining a velocity of said single elongated polymer at said first and second detection zones from said first and/or second signal amplitude profiles; and (d) determining length of said single elongated polymer by multiplying time difference between leading and trailing edges of said first or said second signal amplitude profile with said velocity;

wherein each said signal amplitude profile comprises measurements in the respective detection zone of a signal generated at said single elongated polymer at a plurality of times, said plurality of times comprising times that are before, during and after said elongated polymer is in said detection zone, wherein said first and second detection zones are located in order along the path of said single elongated polymer at predetermined distances, and wherein said first and second signal applitude profiles are measured in a time-correlated manner, wherein said velocity of said single elongated polymer is an end-to-end velocity and wherein said determining a velocity comprises (a) determining temporal location of a first leading end in said first signal amplitude profile and temporal location of a second leading end in said second signal amplitude profile; and (b) calculating said end-to-end velocity by dividing distance between said first and second detection zones with difference between temporal locations of said first leading end and said second leading end.

9. The method of claim 8, wherein said temporal location of said first leading end and said temporal location of said second leading end are identified as the times at half heights of the respective leading edges in said first and second signal amplitude profiles.

* * * * *